(12) United States Patent
Moon et al.

(10) Patent No.: US 12,269,884 B2
(45) Date of Patent: Apr. 8, 2025

(54) ANTIBODY SPECIFICALLY BINDING TO ICAM-1 AND USE THEREOF

(71) Applicant: Kumho HT, Inc., Gwangju (KR)

(72) Inventors: Yoo Ri Moon, Seoul (KR); Gil Yong Ji, Seoul (KR); Sangsoon Yoon, Seoul (KR); Jung Sik Kim, Seoul (KR)

(73) Assignee: KUMHO HT, INC., Gwangju (KR)

( * ) Notice: Subject to any disclaimer, the term of this patent is extended or adjusted under 35 U.S.C. 154(b) by 138 days.

(21) Appl. No.: 17/312,083

(22) PCT Filed: Dec. 31, 2019

(86) PCT No.: PCT/KR2019/018822
§ 371 (c)(1),
(2) Date: Jun. 9, 2021

(87) PCT Pub. No.: WO2020/141869
PCT Pub. Date: Jul. 9, 2020

(65) Prior Publication Data
US 2024/0287188 A1    Aug. 29, 2024

(30) Foreign Application Priority Data
Dec. 31, 2018 (KR) ........................ 10-2018-0173725

(51) Int. Cl.
| | | |
|---|---|---|
| *A61K 39/395* | (2006.01) | |
| *A61K 39/00* | (2006.01) | |
| *A61P 19/02* | (2006.01) | |
| *A61P 37/06* | (2006.01) | |
| *C07H 21/04* | (2006.01) | |
| *C07K 16/00* | (2006.01) | |
| *C07K 16/28* | (2006.01) | |
| *C07K 16/46* | (2006.01) | |
| *C12N 5/20* | (2006.01) | |
| *C12N 15/00* | (2006.01) | |
| *C12P 21/06* | (2006.01) | |
| *G01N 33/53* | (2006.01) | |
| *G01N 33/68* | (2006.01) | |

(52) U.S. Cl.
CPC .......... *C07K 16/2821* (2013.01); *A61P 19/02* (2018.01); *A61P 37/06* (2018.01); *G01N 33/6854* (2013.01); *A61K 2039/505* (2013.01); *C07K 2317/24* (2013.01); *C07K 2317/73* (2013.01); *C07K 2317/92* (2013.01); *C07K 2317/94* (2013.01); *G01N 2333/70525* (2013.01)

(58) Field of Classification Search
None
See application file for complete search history.

(56) References Cited

U.S. PATENT DOCUMENTS

| 8,900,586 B2* | 12/2014 | Park .................. C07K 16/00 |
| | | 530/387.3 |
| 9,815,900 B2 | 11/2017 | Kim et al. |
| 2009/0068637 A1 | 3/2009 | Xia et al. |
| 2014/0079691 A1 | 3/2014 | McConnell et al. |
| 2015/0252111 A1 | 9/2015 | Park et al. |
| 2015/0307945 A1* | 10/2015 | Nakanishi ............. C07K 14/71 |
| | | 424/139.1 |
| 2018/0221482 A1 | 8/2018 | Frendéus et al. |

FOREIGN PATENT DOCUMENTS

| JP | 2009-524434 | 7/2009 |
| KR | 10-2008-0090532 | 10/2008 |
| KR | 10-2011-0023897 | 3/2011 |
| KR | 10-2014-0026567 | 3/2014 |
| KR | 10-1434029 | 8/2014 |
| TW | 201811366 | 4/2018 |
| WO | 91-16927 | 11/1991 |
| WO | 2004-060919 | 7/2004 |
| WO | 2005-086568 | 9/2005 |
| WO | 2007-014992 | 2/2007 |
| WO | 2007-091719 | 8/2007 |
| WO | 2008-007648 | 1/2008 |
| WO | 2010-016652 | 2/2010 |
| WO | WO-2014152006 A2 * | 9/2014 ......... A61K 39/3955 |
| WO | WO-2019056023 A2 * | 3/2019 ......... A61K 31/7088 |

OTHER PUBLICATIONS

Salemela et al. Randomized multicenter Trial of the anti-ICAM-1 monoclonal antibody (Enlimomab) for the prevention of acute rejection and Delayed onset of Graft function in cadaveric rental transplantation. Transplantation 67(5):p. 729-736, Mar. 15, 1999. (Year: 1999).*
NCT06400771. Safety of DNP007 in Healthy Subjects. pp. 1-15, Jun. 13, 2024, (Year: 2024).*
Ding Guo-shan et al., "CTLA-4 Ig combined with ICAM-1 mAb promotes immune tolerance induced by donor-derived immature dendritic cells in recipient mice", Acad J Sec Mil Med Univ, 2006, 27(3): 253-257.
SIPO, Office Action of CN 201980087502.3 dated Oct. 19, 2023.
Juha Vuorte et al., "Anti-ICAM-1 Monoclonal Antibody R6.5 (Enlimomab) Promotes Activation of Neutrophils in Whole Blood", J Immunol, Feb. 15, 1999, 162 (4) 2353-2357.
EPO, Search Report of EP 19907470.9 dated Aug. 18, 2022.
Kipo, A PCT Search Report & Written Opinion of PCT/KR2019/018822 dated Apr. 21, 2020.

(Continued)

*Primary Examiner* — Maher M Haddad
(74) *Attorney, Agent, or Firm* — LEX IP MEISTER, PLLC

(57) ABSTRACT

The present invention relates to an anti-ICAM-1 antibody or an antigen-binding fragment thereof that specifically binds to ICAM-1, and the use thereof. Specifically, provided are an anti-ICAM-1 antibody or an antigen-binding fragment thereof, a pharmaceutical composition for regulating differentiation and/or function of dendritic cell, and a pharmaceutical composition for preventing and/or treating immune cell-mediated disease, the composition comprising the antibody or the antigen-binding fragment as an active ingredient.

10 Claims, 39 Drawing Sheets
Specification includes a Sequence Listing.

(56) References Cited

OTHER PUBLICATIONS

Andrew W. Boyd et al., "Intercellular adhesion molecule 1 (ICAM-1) has a central role in cell-cell contact-mediated immune mechanisms". Proc Natl Acad Sci USA., vol. 85, pp. 3095-3099, May 1988.
A. Benedict Cosimi et al., "In Vivo Effects of Monoclonal Antibody to ICAM-1 (CD54) in Nonhuman Primates With Renal Allografts", J Immunol., vol. 144, 4604-4612, No. 12, Jun. 15, 1990.
Arthur F. Kavanaugh et al., "Treatment of Refractory Rheumatoid Arthritis With a Monoclonal Antibody to Intercellular Adhesion Molecule 1", Arthritis Rheum., vol. 37, No. 7, Jul. 1994, pp. 992-999.
Arthur F. Kavanaugh et al., "A Phase I/II Open Label Study of the Safety and Efficacy of an Anti-ICAM-1 (Intercelluar Adhesion Molecule-1; CD54) Monoclonal Antibody in Early Rheumatoid Arthritis", J Rheumatol. 1996, 23:1338-1344.
Juha Vuorte et al., "Anti-ICAM-1 Monoclonal Antibody R6.5 (Enlimomab) Promotes Activation of Neutrophils in Whole Blood", J Immunol. 1999, 162:2352-2357.
Russian Patent Office, Office Action of RU 2021118997 dated Mar. 3, 2022.
Kyeong Cheon Jung et al., "In situ induction of dendritic cell-based T cell tolerance in humanized mice and nonhuman primates", J. Exp. Med., vol. 208, No. 12, 2477-2488, Oct. 24, 2011.

\* cited by examiner

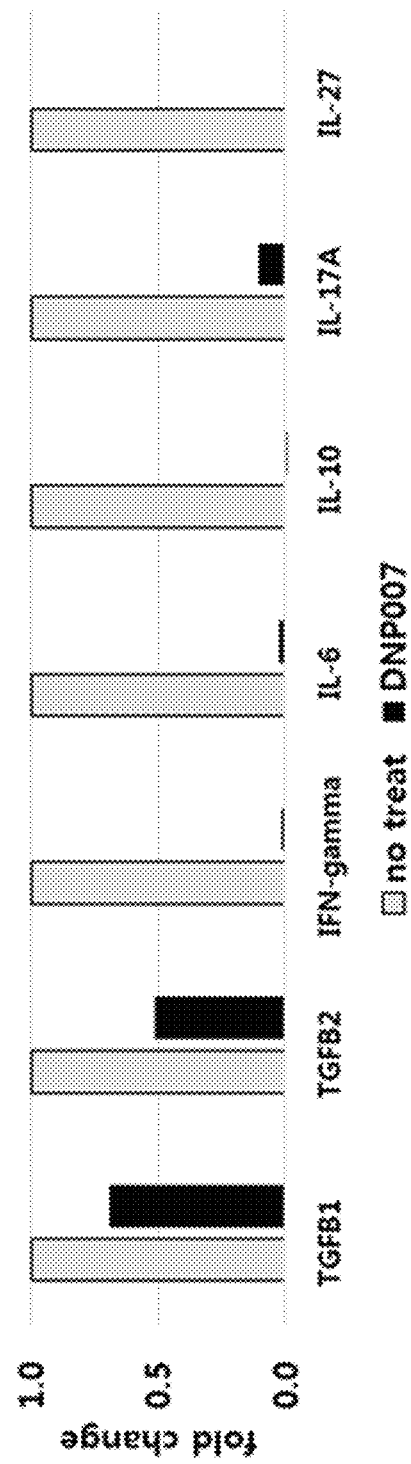
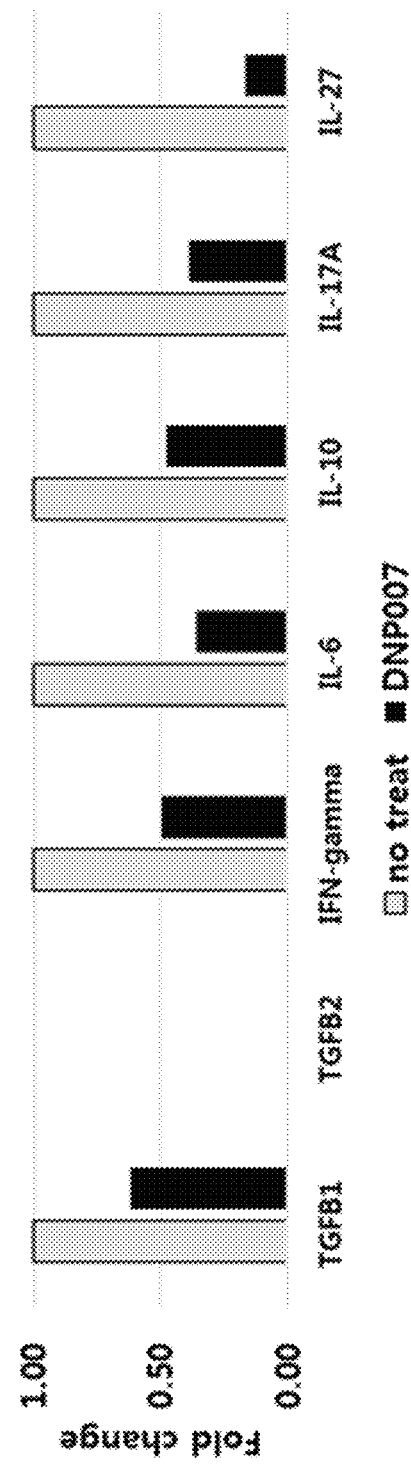
FIG.14

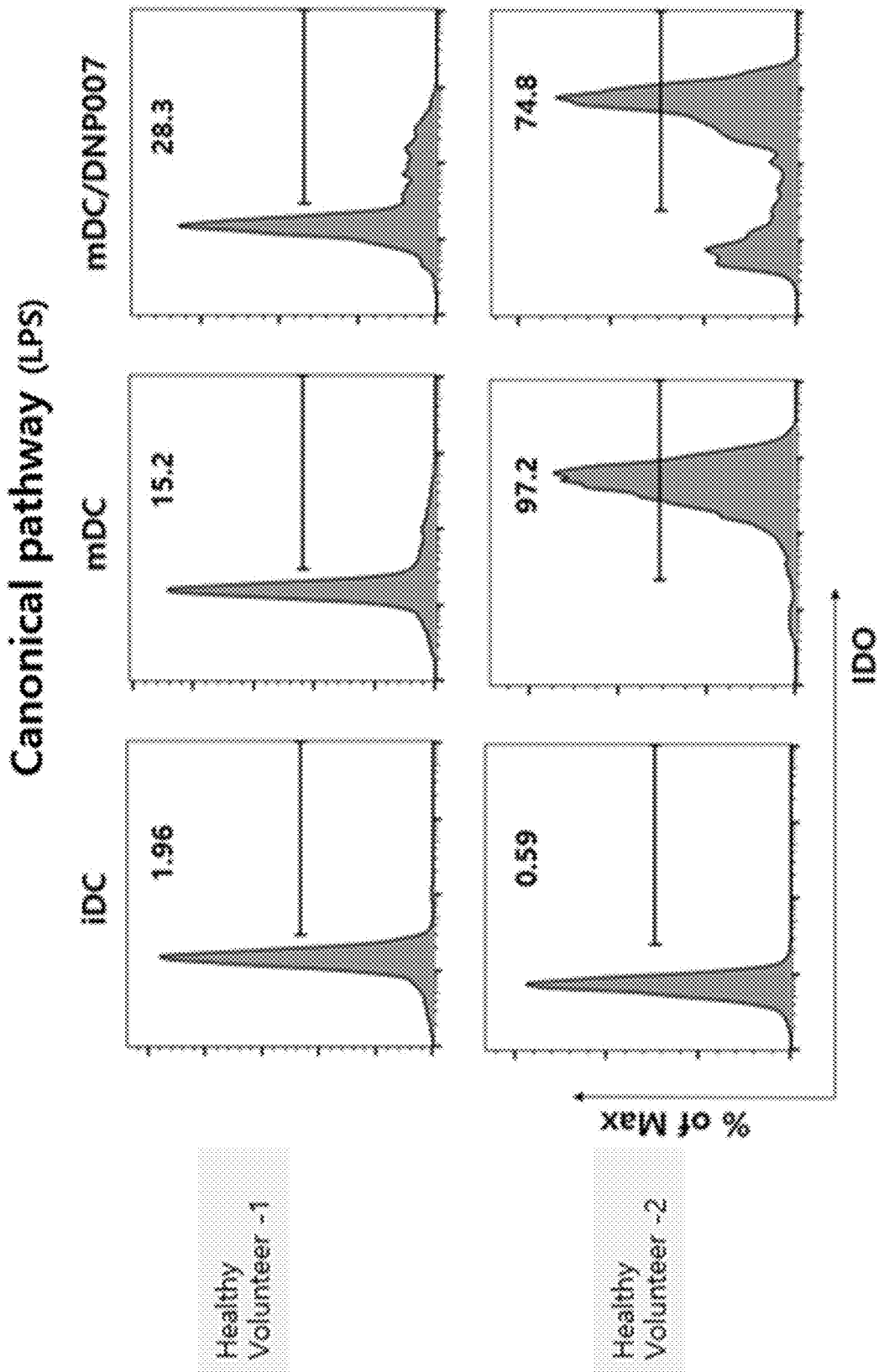

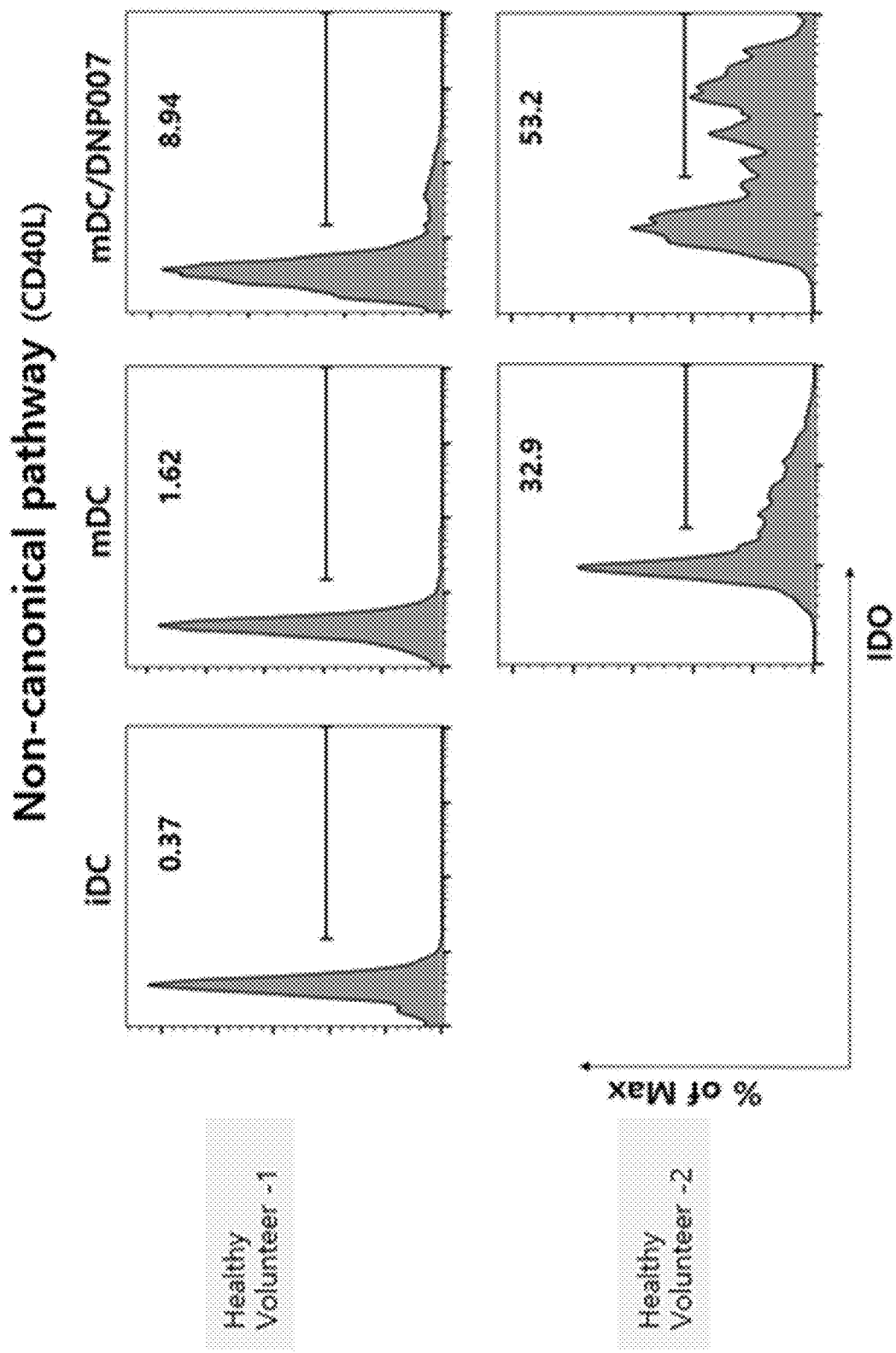

ANTIBODY SPECIFICALLY BINDING TO ICAM-1 AND USE THEREOF

TECHNICAL FIELD

The present disclosure pertains to an anti-ICAM-1 antibody binding specifically to ICAM-1 or an antigen-binding fragment thereof, and use thereof, more particularly, to an anti-ICAM-1 antibody or an antigen-binding fragment thereof, and a pharmaceutical composition for prevention and/or treatment of a immune cell mediated disease and a pharmaceutical composition for regulating the function and/or the differentiation of dendritic cells comprising the antibody or the antigen-binding fragment.

BACKGROUND ART

Dendritic cells (DC) are highly characterized antigen presenting cells that integrate a variety of immune responses, and include a heterogeneous family of antigen presenting cells that are involved in the initiation of immunity and immune tolerance. To date, immature dendritic cells induce T cells into an anergy state, and dendritic cells transformed into mature dendritic cells by active stimulants such as lipopolysaccharide (LPS) induce primary T cell responses. In addition, semi-mature dendritic cells with unique cytokine production profiles can confer immunotolerant functions.

ICAM-1 (Intercellular Adhesion Molecule 1) is named domain 1 to domain 5, and a 90 kDa type I cell surface glycoprotein consisting of five extracellular immunoglobulin superfamily domains numbered from N-terminus to C-terminus, transmembrane region, and intracellular region.

ICAM-1 mediates leukocyte/leukocyte interactions, such as interactions between T cells and antigen presenting cells. It also mediates the outflow of leukocytes into tissues during the inflammatory process. According to the in vitro study, it has been suggested that antibodies that interfere with the interaction of ICAM-1/leukocyte function-related antigen-1 (LFA-1) can interfere with the adhesion of T cells to endothelial cells, and it has been suggested that T cell activation by these antibodies can also be significantly reduced in mixed lymphocytes (Proc Natl Acad Sci USA. 1988, 85:3095-3099). In a monkey study using R6-5-D6 (enlimomab), a mouse monoclonal antibody that binds to the domain of human ICAM-1, the survival rate of renal allografts increased and T cell penetration into the graft decreased compared to the control group (J Immunol. 1990, 144:4604-4612). In addition, it has been demonstrated that enlimomab has an effect of inhibiting disease activity in patients with rheumatoid arthritis (Arthritis Rheum. 1994, 37:992-999; J Rheumatol. 1996, 23:1338-1344). However, enlimomab-induced treatment after kidney transplantation is not very effective in reducing the rate of acute rejection or the risk of delayed graft function. In addition, Enrimomab functions to block the adhesion of neutrophils as well as T cells to vascular endothelial cells, and thus it has been reported that interfering with the migration of neutrophils potentially increases susceptibility to infection (J Immunol. 1999, 162:2352-2357). There is a need to develop a substance that specifically binds to ICAM-1 to regulate the differentiation and function of dendritic cells, thereby controlling the immune response more effectively.

DETAILED DESCRIPTION OF THE INVENTION

Technical Problem

One example provides an anti-ICAM-1 antibody or an antigen-binding fragment thereof that specifically recognizes ICAM-1.

The anti-ICAM-1 antibody or the antigen-binding fragment thereof, may comprise
heavy-chain complementarity determining regions (CDRs) comprising a polypeptide (CDR-H1) comprising the amino acid sequence of SEQ ID NO: 1 (GYTFTDYA), a polypeptide (CDR-H2) comprising the amino acid sequence of SEQ ID NO: 2 (ISTYSGNT), and a polypeptide (CDR-H3) comprising the amino acid sequence of SEQ ID NO: 3 (ARSLYFGSSGFDY) or a heavy-chain variable region comprising the heavy-chain complementarity determining region described above; and
light-chain complementarity determining regions comprising a polypeptide (CDR-L1) comprising the amino acid sequence of SEQ ID NO: 4 (QTLVYRNGNTY), a polypeptide (CDR-L2) comprising the amino acid sequence of SEQ ID NO: 5 (KVS), and a polypeptide (CDR-L3) comprising the amino acid sequence of SEQ ID NO: 6 (SQNTHFPYT) or a light-chain variable region comprising the light-chain complementarity determining region described above.

In one embodiment, the heavy-chain variable region may comprise an amino acid sequence selected from the group consisting of SEQ ID NOs: 7 and 11 to 34, and the light-chain variable region may comprise an amino acid sequence selected from the group consisting of SEQ ID NOs: 8 and 35 to 38.

Another example provides a nucleic acid molecule encoding a heavy chain complementarity determining region, a heavy chain variable region, or a heavy chain of an anti-ICAM-1 antibody.

Another example provides a nucleic acid molecule encoding a light chain complementarity determining region, a light chain variable region, or a light chain of an anti-ICAM-1 antibody.

Another example provides a recombinant vector comprising a nucleic acid molecule encoding a heavy-chain complementarity determining region, a heavy-chain variable region or a heavy-chain of the anti-ICAM-1 antibody and a nucleic acid molecule encoding a light-chain complementarity determining region, a light-chain variable region or a light-chain of the anti-ICAM-1 antibody in a single vector or each in separate vectors.

Another example may provide a recombinant cell comprising the recombinant vector.

Another example may provide a pharmaceutical composition for prevention and/or treatment of a disease comprising the anti-ICAM-1 antibody or the antigen-binding fragment thereof as an active ingredient. The disease may be an immune cell mediated disease. Another example provide a method for preventing and/or treating an immune cell mediated disease, the method comprising a step of administering a pharmaceutically effective amount of the anti-ICAM-1 antibody and/or the antigen-binding fragment to a subject in need of prevention and/or treatment of an immune cell mediated disease. The method may further comprise the step of identifying a subject in need of prevention and/or treatment of an immune cell mediated disease prior to the administering step. Another example provides a use of the anti-ICAM-1 antibody or the antigen-binding fragment thereof in preventing and/or treating immune cell mediated disease or a use of the anti-ICAM-1 antibody or the antigen-binding fragment thereof in the manufacture of a medicament for prevention or treatment of immune cell mediated disease. In the pharmaceutical composition, method, and use, the immune cell-mediated disease may be selected from transplant rejection, graft-versus-host disease, asthma, autoimmune disease, and the like.

Another example provides a pharmaceutical composition for regulating the function and/or differentiation of a dendritic cell comprising the anti-ICAM-1 antibody or the antigen-binding fragment thereof as an active ingredient. Another example provides a method for regulating the function and/or differentiation of a dendritic cell, comprising a step of administering a pharmaceutically effective amount of an anti-ICAM-1 antibody or an antigen-binding fragment thereof to a subject in need of regulating the function and/or differentiation of a dendritic cell. Another example provides a use of an anti-ICAM-1 antibody or an antigen-binding fragment thereof in the manufacture of a medicament for regulating the function and/or differentiation of an immune cell mediated disease.

Technical Solution

In the present specification, provided are an anti-ICAM-1 antibody or an antigen-binding fragment thereof that specifically recognizes ICAM-1 and a use thereof.

The anti-ICAM-1 antibody or the antigen-binding fragment thereof is characterized in that it specifically recognizes and/or binds to a domain 2 among the domains of ICAM-1. The anti-ICAM-1 antibody or the antigen-binding fragment thereof may be an antagonist having inhibitory activity against ICAM-1. However, the antibody does not inhibit ICAM-1/LFA-1 binding itself by binding to a domain 2 rather than a domain 1 of ICAM-1, which is a binding site for LFA-1, a ligand of ICAM-1 which is an antigen. This may be confirmed by the fact that the antibody does not inhibit the transmigration of T cells. The antibody may potentially affect the activation of the spatial function of immune synapses for transmission of T cell activity and the binding and reorganization between related proteins, in that it suppresses the immune activity of T cells in co-culture with dendritic cells and T cells and functionally induces immune suppression by inducing differentiation into tolerogenic dendritic cells. In this respect, the antibody may be an antagonist that functionally inhibits ICAM-1 activity rather than physically inhibiting receptor-ligand binding. In addition, the antibody may induce a result of suppressing the immune activity of T cells comprising the ligand as a result of the above-described activity. In other words, the anti-ICAM-1 antibody or the antigen-binding fragment thereof provided herein may inhibit the function and/or differentiation of a dendritic cell, and may have a preventive and/or therapeutic effect on an immune cell-mediated disease by binding to a domain 2 of ICAM-1 (e.g., human ICAM-1) and inducing antigen-specific T-cell tolerance.

ICAM-1 (Intercellular Adhesion Molecule 1), also called CD54 (Cluster of Differentiation 54), is a cell surface glycoprotein expressed on an endothelial cell or an immune system cell.

ICAM-1 acting as an antigen of the antibody provided herein may be of mammalian origin, for example, human ICAM-1 (e.g., NCBI accession numbers NP_000192.2, etc.), monkey ICAM-1 (e.g., NCBI accession numbers NP_001266532, etc.). In one example, the antibody may exhibit cross-reactivity to human ICAM-1 and monkey ICAM-1.

In the present specification, the term "antibody" refers to a substance produced by stimulation of an antigen in the immune system or a protein that specifically binds to a specific antigen, and it is used as a concept to include a protein produced recombinantly or synthetically based on the substance or the protein. The antibody may be non-naturally produced, for example, recombinantly or synthetically produced. The antibody may be an animal antibody (e.g., a mouse antibody, etc.), a chimeric antibody (e.g., a mouse-human chimeric antibody), a humanized antibody, or a human antibody. The antibody may be a monoclonal antibody or a polyclonal antibody.

In addition, in the present specification, the antibody may be understood to include all fragments of an antibody having antigen-binding ability unless otherwise specified. In the present specification, the term "complementarity-determining regions (CDRs)" refers to a region that confers antigen-binding specificity among variable regions of an antibody. The antigen-binding fragment of the antibody described above may be an antibody fragment comprising one or more of the complementarity determining region.

One example provides an anti-ICAM-1 antibody or an antigen-binding fragment thereof that specifically recognizes ICAM-1 or specifically binds to ICAM-1.

The anti-ICAM-1 antibody or the antigen-binding fragment thereof, may comprise heavy-chain complementarity determining regions (CDRs) comprising a polypeptide (CDR-H1) comprising the amino acid sequence of SEQ ID NO: 1 (GYTFTDYA), a polypeptide (CDR-H2) comprising the amino acid sequence of SEQ ID NO: 2 (ISTYSGNT), and a polypeptide (CDR-H3) comprising the amino acid sequence of SEQ ID NO: 3 (ARSLYFGSSGFDY) or a heavy-chain variable region comprising the heavy-chain complementarity determining region described above; and light-chain complementarity determining regions comprising a polypeptide (CDR-L1) comprising the amino acid sequence of SEQ ID NO: 4 (QTLVYRNGNTY), a polypeptide (CDR-L2) comprising the amino acid sequence of SEQ ID NO: 5 (KVS), and a polypeptide (CDR-L3) comprising the amino acid sequence of SEQ ID NO: 6 (SQNTHFPYT) or a light-chain variable region comprising the light-chain complementarity determining region described above.

In the heavy-chain variable region, heavy-chain framework 1 (VH-FR1; N-terminal adjacent region of CDRH1) may comprise an amino acid sequence of SEQ ID NO: 97 (QVQLX1QSGAEX2X3X4PGX5SVKX6SCKX7S; X1 is Q or V, X2 is L or V, X3 is V or K, X4 is R or K, X5 is V or A, X6 is I or V, X7 is G or A) or SEQ ID NO: 98 (QVQLX8QSGAEVX9KPGASVKX10SCKX11S; X8 is V or Q, X9 is K or V, X10 is I or V, X11 is G o A), for example, an amino acid sequence selected from SEQ ID NOs: 39, 40, 41, 42, 43, 44, 45, 46, 47, and 48, heavy-chain framework 2 (VH-FR2; the region between the C-terminus of CDRH1 and the N-terminus of CDRH2) may comprise an amino acid sequence of SEQ ID NO: 99 (LHWVX12QX13X14X15X16X17LEWX18GV; X12 is K or R, X13 is S or A, X14 is H or P, X15 is A or G, X16 is K or Q, X17 is S or R, X18 is I or M) or SEQID NO: 100 (LHWV X19QAPGQX20LEWX21GV; X19 i R or K, X20 is R or S, X21 is I or M), for example, an amino acid sequence selected from SEQ ID NOs: 49, 50, 51, 52, 53, 54, and 55, heavy-chain framework 3 (VH-FR3; the region between the C-terminus of CDRH2 and the N-terminus of CDRH3) may comprise an amino acid sequence of SEQ ID NO: 101 (X22YX23QKFX24GX25X26TX27TX28DX29SX30X31TAYX32ELX33X34LX35SEDX36A X37X38YC; X22 is D or K, X23 is N or S, X24 is R or Q, X25 is K or R, X26 is A or V, X27 is M or I, X28 is V or R, X29 is K or T, X30 is S or A, X31 is T or S, X32 is L or M, X33 is A or S, X34 is R or S, X35 is T or R, X36 is S or T, X37 is I or V, X38 isH or Y) or SEQ ID NO: 102 (X39YX40QKFX41GX42X43TX44TX45RX46SAX47TAYX48ELSSLRSEDTAX49X50YC; X39 is D or K, X40 is N or S, X41 is R or Q, X42 is R or K, X43 is A or V, X44 is I or M, X45 is R or V, X46 is T or K, X47 is S or T, X48 is M or L, X49 is V or I, X50 is Y or H)), for example, an amino acid sequence selected from SEQ ID NOs: 56, 57, 58, 59, 60, 61, 62, 63, 64, 65, 66, 67, 68, 69, 70, 71, 72, 73, 74, 75, 76, 77, 78, 79, and 80, and/or heavy-chain framework 4 (VH-FR4; a region adjacent to the C-terminus of CDRH3) may comprise an amino acid sequence of SEQ ID NO: 81.

In the light-chain variable region, light-chain framework 1 (VL-FR1; N-terminal adjacent region of CDRL1) may comprise an amino acid sequence of SEQ ID NO: 103 (DVVLTQX51PLSX52PVX53LGX54X55ASISCRSS; X51 is T or S, X52 is L or S, X53 is N or T, X54 is D or Q, X55 is Q or P) or SEQ ID NO: 104 (DVVLTQX56PLSX57PVTLGQPASISCRSS; X56 is S or T, X57 is L or S) for example, an amino acid sequence selected from SEQ ID NOs: 82, 83, and 84, light-chain framework 2 (VL-FR2; the region between the C-terminus of CDRL1 and the N-terminus of CDRL2) may comprise an amino acid sequence of SEQ ID NO: 105 (LHWYX58QX59X60GQX61PX62LLIX63; X58 is L or Q, X59 is K or R, X60 is A or P, X61 is S or P, X62 is K or R, X63 is Y or absent), for example, an amino acid sequence selected from SEQ ID NOs: 85, 86, 87, 88, and 89, light-chain framework 3 (VL-FR3; the region between the C-terminus of CDRL2 and the N-terminus of CDRL3) may comprise an amino acid sequence of SEQ ID NO: 106 (NRFSGVPDRFSGSGX64GTDFTLKISRVEAEDX65GVYFC; X64 is S or A, X65 is L or V), for example, an amino acid sequence selected from SEQ ID NOs: 90, 91, and 93, and/or light-chain framework 4 (VL-FR4; a region adjacent to the C-terminus of CDRL3) may comprise an amino acid sequence of SEQ ID NO: 107 (FGGGTKX66X67X68X69X70; X66 is I or L, X67 is K or E, X68 is R or I, X69 is Q or K, X70 is R or absent), for example, an amino acid sequence of SEQ ID NO: 93 or 94.

In the anti-ICAM-1 antibody or the antigen-binding fragment thereof, the heavy chain variable region may comprise VH-FR1 comprising an amino acid sequence of SEQ ID NO: 97 or 98 (e.g., SEQ ID NO: 39, 40, 41, 42, 43, 44, 45, 46, 47, or 48), CDRH1 comprising an amino acid sequence of SEQ ID NO: 1, VH-FR2 comprising an amino acid sequence of SEQ ID NO: 99 or 100 (e.g., SEQ ID NO: 49, 50, 51, 52, 53, 54, or 55), CDRH2 comprising an amino acid sequence of SEQ ID NO: 2, VH-FR3 comprising an amino acid sequence of SEQ ID NO: 101 or 102 (e.g., SEQ ID NO: 56, 57, 58, 59, 60, 61, 62, 63, 64, 65, 66, 67, 68, 69, 70, 71, 72, 73, 74, 75, 76, 77, 78, 79, or 80), CDRH3 comprising an amino acid sequence of SEQ ID NO: 3, and VH-FR4 comprising an amino acid sequence of SEQ ID NO: 81; and the light-chain variable region may comprise VL-FR1 comprising an amino acid sequence of SEQ ID NO: 103 or 104 (e.g., SEQ ID NO: 82, 83, or 84), CDRL1 comprising an amino acid sequence of SEQ ID NO: 4, VL-FR2 comprising an amino acid sequence of SEQ ID NO: 105 (e.g., SEQ ID NO: 85, 86, 87, 88, or 89), CDRL2 comprising an amino acid sequence of SEQ ID NO: 5, VL-FR3 comprising an amino acid sequence of SEQ ID NO: 106 (e.g., SEQ ID NO: 90, 91, or 93), CDRL3 comprising an amino acid sequence of SEQ ID NO: 6, and VL-FR4 comprising an amino acid sequence of SEQ ID NO: 107 (e.g., SEQ ID NO: 93 or 94).

In one embodiment, the heavy-chain variable region may comprise an amino acid sequence selected from the group consisting of SEQ ID NOs: 7 and 11 to 34, and the light-chain variable region may comprise an amino acid sequence selected from the group consisting of SEQ ID NOs: 8 and 35 to 38.

Animal-derived antibodies produced by immunizing a desired antigen to an immunized animal may generally cause an immune rejection reaction when administered to humans for a therapeutic purpose, and a chimeric antibody has been developed to suppress this immune rejection reaction. Chimeric antibodies are those obtained by substituting a constant region of an animal-derived antibody that causes an anti-isotype response with a constant region of a human antibody using genetic engineering methods. Chimeric antibodies have been significantly improved in anti-isotype response compared to animal-derived antibodies, but animal-derived amino acids are still present in the variable region, which has side effects for a potential anti-idiotypic response. A humanized antibody was developed to improve these side effects. This is produced by grafting a CDR (complementarity determining regions) region that plays an important role in antigen binding among the variable regions of a chimeric antibody into a human antibody framework.

The most important thing in CDR grafting technology for producing a humanized antibody is to select an optimized human antibody that can best accept the CDR regions of an animal-derived antibody, to this end, the use of antibody databases, crystal structure analysis, molecular modeling technology, and the like may be used.

According to one embodiment, the antibody may be an animal antibody (e.g., a mouse antibody), a chimeric antibody (e.g., a mouse-human chimeric antibody) or a humanized antibody.

In the antibody or the antigen-binding fragment, the heavy-chain framework and/or heavy-chain constant region except for the heavy-chain CDRs of SEQ ID NOs: 1 to 3 may be a heavy-chain framework and/or a heavy-chain constant region derived from an immunoglobulin (IgG (IgG1, IgG2, IgG3, IgG4, etc.), IgM, IgA, IgD, or IgE), for example, an human immunoglobulin (IgG (IgG1, IgG2, IgG3, IgG4, etc.), IgM, IgA, IgD, or IgE), and the light-chain framework and/or the light-chain constant region except for the light-chain CDRs of SEQ ID NOs: 4 to 6 may be a light-chain framework and/or a light-chain constant region of a kappa (κ) or lambda (λ) type.

A complete antibody has two full-length light chains and two full-length heavy chains, in which each light chain is linked to a heavy chain via a disulfide bond. The constant region of an antibody is divided into a heavy chain constant region and a light chain constant region, and the heavy chain constant region has a gamma (γ), mu (μ), alpha (α), delta (δ) and epsilon (ε) type, and has gamma 1 (γ1), gamma 2 (γ2), gamma 3 (γ3), gamma 4 (γ4), alpha 1 (α1) and alpha 2 (α2) as its subclass. The constant region of the light-chain has a kappa (κ) and lambda (λ) type.

The term "heavy chain" is intended to encompass a full-length heavy chains and fragments thereof, the full-length heavy chain comprising a variable region domain $V_H$ inclusive of amino acid sequences sufficient to provide specificity to antigens, three constant regions, $C_{H1}$, $C_{H2}$, and $C_{H3}$, and a hinge. In addition, the term "light chain" is intended to encompass full-length light chains and fragments thereof, the full-length light chain comprising a variable region domain $V_L$ inclusive of amino acid sequences sufficient to provide specificity to antigens, and a constant region $C_L$.

The term "complementarity determining region (CDR)" refers to an amino acid sequence found in a hypervariable region of a heavy chain or a light chain of immunoglobulin. The heavy and light chains may respectively comprise three CDRs (CDRH1, CDRH2, and CDRH3; and CDRL1, CDRL2, and CDRL3). The CDR may provide a contact residue that plays an important role in the binding of antibodies to antigens or epitopes. On the other hand, in the present specification, the terms "specifically binding" and "specifically recognizing" have the same general meaning as known to one of ordinary skill in the art, and indicate that an antibody and an antigen specifically interact with each other to lead to an immunological reaction.

The term "antigen-binding fragment" refers to fragments of an intact immunoglobulin comprising a portion of a polypeptide accounting for an antigen-binding site, for example, a part of an antibody comprising CDRs. For example, antigen-binding fragment may be scFv, (scFv)$_2$, scFvFc, Fab, Fab', or F(ab')$_2$.

Fab is a structure having a variable region of a light chain and heavy chain, a constant region of a light chain, and a first constant region (CH1) of a heavy chain, and has one antigen-binding site. Fab' is different from Fab in that Fab' includes a hinge region with at least one cysteine residue at the C-terminal of $C_{H1}$. An F(ab')2 antibody is formed through disulfide bridging of the cysteine residues in the hinge region of Fab'. Fv is a minimal antibody fragment composed of only a heavy chain variable region and a light chain variable region.

Recombination techniques of generating an Fv fragment are widely known in the art. Two-chain Fv includes a heavy chain variable region and a light chain region which are linked to each other by a non-covalent bond. Single-chain Fv generally includes a heavy-chain variable region and a light-chain variable region which are linked to each other by a covalent bond via a peptide linker or linked at the C-terminals to have a dimer structure like the two-chain Fv.

The antigen-binding fragments may be obtained using protease (for example, Fab may be obtained by restrictively cleaving a whole antibody with papain, and an F(ab')2 fragment may be obtained by cleavage with pepsin), or may be prepared by using a genetic recombination technique.

The term "hinge region," as used herein, refers to a region between CH1 and CH2 domains within the heavy chain of an antibody, which functions to provide flexibility for the antigen-binding site.

The anti-ICAM-1 antibody may be a monoclonal antibody. A monoclonal antibody may be prepared using a method widely known in the art, for example, using a phage display technique. Alternatively, the anti-ICAM-1 antibody may be constructed in the form of a animal (e.g., mouse)-derived monoclonal antibody by a conventional method.

Meanwhile, individual monoclonal antibodies may be screened based on the binding ability to ICAM-1 using a typical ELISA (Enzyme-Linked ImmunoSorbent Assay) format. Inhibitory activity may be assayed through functional assays such as cell-based assay or functional assays such as competitive ELISA (Competitive ELISA) to assay molecular interactions for conjugates. The respective affinity (Kd values) for ICAM-1 may then be assayed for selected monoclonal antibody members based on strong inhibitory activity.

Another example provides a pharmaceutical composition for prevention and/or treatment of disease, the composition comprising the anti-ICAM-1 antibody or the antigen-binding fragment thereof as an active ingredient. The disease may be an immune cell mediated disease. Another example provides a method for prevention and/or treatment of immune cell mediated disease, the method comprising a step of administering a pharmaceutically effective amount of the anti-ICAM-1 antibody or the antigen-binding fragment thereof to a subject in need of prevention and/or treatment of immune cell mediated disease. The method may further comprise a step of identifying a patient in need of prevention and/or treatment of immune cell mediated disease prior to the administering step. Another example provides a use of the anti-ICAM-1 antibody or the antigen-binding fragment thereof in preventing and/or treating an immune cell mediated disease or a use of the anti-ICAM-1 antibody or the antigen-binding fragment thereof in the manufacture of a medicament for prevention or treatment of an immune cell mediated disease.

In the pharmaceutical composition, the method, and the use, the immune cell mediated disease may be selected from all diseases related to immune cell. The immune cell may be at least one selected from the group consisting of T cell, B cell, dendritic cell, macrophage, monocyte, and the like. In one example, the immune cell mediated disease may be selected from transplant rejection (e.g., rejection that occurs during allogeneic cell transplantation, allogeneic organ transplantation, xenogeneic cell transplantation, xenogeneic organ transplantation), graft versus host disease (e.g., graft versus host disease that occurs during allogeneic bone marrow transplantation), asthma, obesity, type 2 diabetes, autoimmune disease (e.g., encephalomyelitis (e.g., allergic encephalomyelitis), rheumatoid arthritis, systemic lupus erythematosus (lupus), atopic dermatitis, multiple sclerosis, type 1 diabetes, chronic inflammatory disease (e.g., inflammatory bowel disease (e.g., Crohn's disease, ulcerative colitis)), Behcet's disease, Sjogren's syndrome, myasthenia gravis, scleroderma, polyarteritis nodosa, Kikuchi disease, collagen disease, Hashimoko thyroiditis, psoriasis Vitiligo, hyperthyroidism, fibromyalgia, alopecia areata, allergy, etc.), immune cell (e.g., T cell, B cell, dendritic cell, macrophage, monocyte, etc.) mediated inflammation (e.g., macrophage-mediated inflammation, etc.), inflammatory disease caused by the immune cell mediated inflammation, and the like.

Another example provides a pharmaceutical composition for regulating differentiation and/or function of dendritic cell, the composition comprising the anti-ICAM-1 antibody or the antigen-binding fragment thereof as an active ingredient. Another example is a method for regulating differentiation and/or function of dendritic cell, the method comprising a step of administering a pharmaceutically effective amount of the anti-ICAM-1 antibody or the antigen-binding fragment thereof to a subject in need of regulation of dendritic cell differentiation and function. Another example provides a use of the anti-ICAM-1 antibody or the antigen-binding fragment thereof in regulating differentiation and/or function of dendritic cell or a use of the anti-ICAM-1 antibody or the antigen-binding fragment thereof in the manufacture of a medicament for regulating differentiation and/or function of dendritic cell.

The pharmaceutical composition may further comprise a pharmaceutically acceptable carrier.

The pharmaceutically acceptable carrier may be commonly used in the formulation of drugs and one or more selected from the group consisting of lactose, dextrose, sucrose, trehalose, arginine, histidine, sorbitol, mannitol, starch, gum acacia, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate, mineral oil, etc., but is not limited thereto. The pharmaceutical composition may further comprise one or more selected from the group consisting of diluent, excipients, lubricant, wetting agent, sweetening agent, flavoring agent, emulsifying agent, suspending agent, preservative, and the like, which is commonly used in the manufacture of pharmaceutical composition.

The pharmaceutical composition or an effective amount of the antibody or the antigen-binding fragment thereof may be administered orally or parenterally. For parenteral administration, intravenous injection, subcutaneous injection, intramuscular injection, intraperitoneal injection, endothelial administration, intranasal administration, intrapulmonary administration, intrarectal administration, or topical administration to the lesion area may be administered. Since oral administration leads to digestion of proteins or peptides, an active ingredient in the compositions for oral administration may be coated or formulated to prevent digestion in the stomach. In addition, the composition may be administered using an optional device that enables an active ingredient to be delivered to target cell.

As described herein, the "pharmaceutically effective amount" may mean the amount or dosage of the active ingredient (ie, anti-ICAM-1 antibody or antigen-binding fragment thereof) and may be determined in a variety of ways by factors such as formulation method, mode of administration, patient's age, weight, sex, pathological condition, food, administration time, administration interval, route of administration, rate of excretion, and response sensitivity.

The content of the anti-ICAM-1 antibody or the antigen-binding fragment thereof or the dosage of the anti-ICAM-1 antibody or the antigen-binding fragment thereof in the pharmaceutical composition may be prescribed in various ways, depending on factors such as formulation method, mode of administration, patient's age, weight, sex, pathological condition, food, administration time, administration interval, route of administration, excretion rate and response sensitivity. For example, a daily dosage of the anti-ICAM-1 antibody or the antigen-binding fragment thereof may be within the range of 0.001 to 1000 mg/kg, particularly 0.01 to 100 mg/kg, more particularly 0.1 to 50 mg/kg, and even more particularly 0.1 to 20 mg/kg, but is not limited thereto. The daily dosage may be formulated into a single formulation in a unit dosage form or formulated in suitably divided dosage forms, or it may be manufactured to be contained in a multiple dosage container.

The pharmaceutical composition may be administered in combination with other medications such as other anticancer agents, and proper prescriptions may be made on the dose, the administration method, and kinds of the other medications, depending on patients' states.

The pharmaceutical composition may be formulated into a form of a solution in oil or an aqueous medium, a suspension, syrup, an emulsion, an extract, powder, granules, a tablet, or a capsule, and may further comprise a dispersing or a stabilizing agent for formulation.

Patient subject to administration of the pharmaceutical composition may be a mammal, comprising a primate comprising a human and a monkey.

Meanwhile, since the anti-ICAM-1 antibody or the antigen-binding fragment thereof specifically binds to ICAM-1, ICAM-1 may be detected or confirmed using thereof. Accordingly, another example of the present invention provides a composition for detection of ICAM-1, the composition comprising the anti-ICAM-1 antibody or the antigen-binding fragment thereof. Another example provides a method of detecting ICAM-1, the method comprising a step of treating a biological sample with the anti-ICAM-1 antibody or the antigen-binding fragment thereof; and a step of identifying whether the antigen-antibody reaction. If an antigen-antibody reaction detected, it may be determined (decided) that ICAM-1 is present in the biological sample. Therefore, the detection method may further comprise a step of determining that ICAM-1 is present in the biological sample when the antigen-antibody reaction is detected after the step of determining whether the antigen-antibody reaction. The biological sample may be selected from the group consisting of cells, tissues, and body fluids obtained (isolated) from mammals, such as humans (e.g., patients to be transplanted or ha ve received a transplant, patients with autoimmune diseases, etc.), and cultures thereof.

The step of identifying whether the antigen-antibody reaction may be carried out using various methods known in the art. For example, it may be measured through a conventional enzymatic reaction, fluorescence, luminescence, and/or radiation detection, and specifically may be measured by a method selected from the group consisting of immunochromatography, immunohistochemistry, enzyme linked immunosorbent assay (ELISA), radioimmunoassay (RIA), enzyme immunoassay (EIA), Fluorescence immunoassay (FIA), luminescence immunoassay (LIA), Western blotting, microarray, etc., but is not limited thereto.

In another example, a polypeptide molecule is provided, the polypeptide molecule comprising a heavy chain complementarity determining region, a light chain complementarity determining region, or a combination thereof of the anti-ICAM-1 antibody described above; or a heavy chain variable region, a light chain variable region, or a combination thereof. The polypeptide molecule may be used for antibody production as a precursor of an antibody, and may be comprised as a constituent of a protein scaffold (for example a peptibody), a bispecific antibody, or a multispecific antibody having a structure similar to that of the antibody.

Another example provides a nucleic acid molecule encoding a heavy chain complementarity determining region, a heavy chain variable region, or a heavy chain of an anti-ICAM-1 antibody.

Another example provides a nucleic acid molecule encoding a light chain complementarity determining region, a light chain variable region, or a light chain of an anti-ICAM-1 antibody.

Another example provides a recombinant vector comprising a nucleic acid molecule encoding a heavy chain complementarity determining region, a heavy chain variable region, or a heavy chain of the anti-ICAM-1 antibody, and a nucleic acid molecule encoding a light chain complementarity determining region, a light chain variable region or a light chain of the anti-ICAM-1 antibody, in a single vector or in separate vectors carrying each of the polynucleotides.

The term "vector" refers to a means for expressing a target gene in a host cell, as exemplified by a plasmid vector, a cosmid vector, and a viral vector such as a bacteriophage vector, an adenovirus vector, a retrovirus vector, and an adeno-associated virus vector. The recombinant vector may be constructed from plasmids frequently used in the art (for example, pSC101, pGV1106, pACYC177, ColE1, pKT230, pME290, pBR322, pUC8/9, pUC6, pBD9, pHC79, pIJ61, pLAFR1, pHV14, pGEX series, pET series, and pUC19), phages (for example, λgt4λB, λ-Charon, λΔz1, and M13) or by manipulating viruses (for example, SV40, etc.).

In the recombinant vector, the polynucleotide may be operatively linked to a promoter. The term "operatively linked" is intended to pertain to a functional linkage between a nucleotide sequence of interest and an expression regulatory sequence (for example, a promoter sequence). When being "operatively linked", the regulatory element may control the transcription and/or translation of the other nucleotide sequences.

The recombinant vector may be constructed typically as a cloning vector or an expression vector. For recombinant expression vectors, a vector generally available in the art for expressing a foreign protein in plant, animal, or microbial cells may be employed. Various methods well known in the art may be used for the construction of recombinant vectors.

For use in hosts, such as prokaryotic or eukaryotic cells, the recombinant vector may be constructed accordingly. For example, when a vector is constructed as an expression vector for use in a prokaryotic host, the vector typically includes a strong promoter for transcription (e.g., a pLκλ, promoter, a CMV promoter, a trp promoter, a lac promoter, a tac promoter, a T7 promoter, etc.), a ribosomal binding site for initiating translation, and transcriptional/translational termination sequences. On the other hand, an expression vector for use in a eukaryotic host comprises an origin of replication operable in a eukaryotic cell, such as an f1 origin of replication, an SV40 origin of replication, a pMB1 origin of replication, an adeno origin of replication, an AAV origin of replication, and a BBV origin of replication, but is not limited thereto. In addition, the expression vector typically includes a promoter derived from genomes of mammalian cells (for example, metallothionein promoter) or from mammalian viruses (for example, adenovirus late promoter, vaccinia virus 7.5K promoter, SV40 promoter, cytomegalovirus promoter, and tk promoter of HSV), and a polyadenylation sequence as a transcription termination sequence.

Another example provides a recombinant cell comprising the recombinant vector.

The recombinant cell may be prepared by introducing the recombinant vector into a suitable host cell. As long as it allows the sequential cloning and expression of the recombinant vector in a stable manner, any host cell known in the art may be employed in the present disclosure. Examples of the prokaryotic host cell available for the present disclosure include *E. coli, E. coli* JM109, *E. coli* BL21, *E. coli* RR1, *E. coli* LE392, *E. coli* B, *E. coli* X 1776, *E. coli* W3110, *Bacillus* spp. such as *Bacillus subtilis* and *Bacillus thuringiensis*, and enterobacteriaceae strains such as *Salmonella typhimurium, Serratia marcescens* and various *Pseudomonas* species. Eukaryotic host cells that may be used for transformation may include, but are not limited to, *Saccharomyces cerevisiae*, insect cells, and animal cells, such as Sp2/0, CHO (Chinese hamster ovary) K1, CHO DG44, CHO-S, PER.C6, W138, BHK, COS-7, 293, HepG2, Huh7, 3T3, RIN, MDCK, HEK293 cell line, etc., but is not limited thereto.

The nucleic acid molecule or a recombinant vector carrying the same may be introduced (transfected) into a host cell using a method well known in the art. This transfection may be carried out using a $CaCl_2$ or electroporation method when the host cell is prokaryotic. For eukaryotic host cells, the genetic introduction may be achieved using, but not limited to, microinjection, calcium phosphate precipitation, electroporation, liposome-mediated transfection, and particle bombardment, etc., but is not limited thereto.

The method of selecting the transformed host cell may be easily carried out according to a method well known in the art using a phenotype expressed by a selection marker. For example, when the selection marker is a gene conferring resistance to a certain antibiotic, the transformant may be easily selected by culturing the transformant in a medium containing the antibiotic.

Another example provides a method for production of an anti-ICAM-1 antibody or an antigen-binding fragment thereof, the method comprising a step of expressing the polynucleotide or the recombinant vector comprising the same in a host cell. The production method may comprise a step of culturing a recombinant cell comprising the recombinant vector, and optionally may further comprise a step of isolating and/or purifying the antibody from the culture medium.

Advantageous Effects

The anti-ICAM-1 antibody or the antigen-binding fragment thereof provided herein binds to domain 2 of human ICAM-1, and has a property of inducing antigen-specific T-cell resistance, thereby it can be usefully used for the regulation of the differentiation and/or function of dendritic cells and/or for prevention and/or treatment of immune cell mediated disease.

BRIEF DESCRIPTION OF THE DRAWINGS

FIG. 14 is a graph showing changes in cytokines obtained by administration of the humanized antibody DNP007 obtained according to one example under conditions of co-culture with dendritic cells and their own T cells by analyzing the changed increase and decrease in the protein level.

FIGS. 19a and 19b are graphs showing the expression level of IDO (Indoleamine 2,3-Dioxygenase) in dendritic cells treated with the humanized antibody DNP007 obtained according to one example, FIG. 19a is a Canonical pathway result, FIG. 19b is a non-canonical pathway result. Show each.

FIGS. 22a and 22b show arthritis scores before and after antibody administration, and FIG. 22c shows anti-collagen antibody levels, respectively.

FIG. 23a shows the survival rate, and FIG. 23b shows the degree of T cell re-establishment, respectively.

MODE FOR CARRYING OUT THE INVENTION

Figure 1:
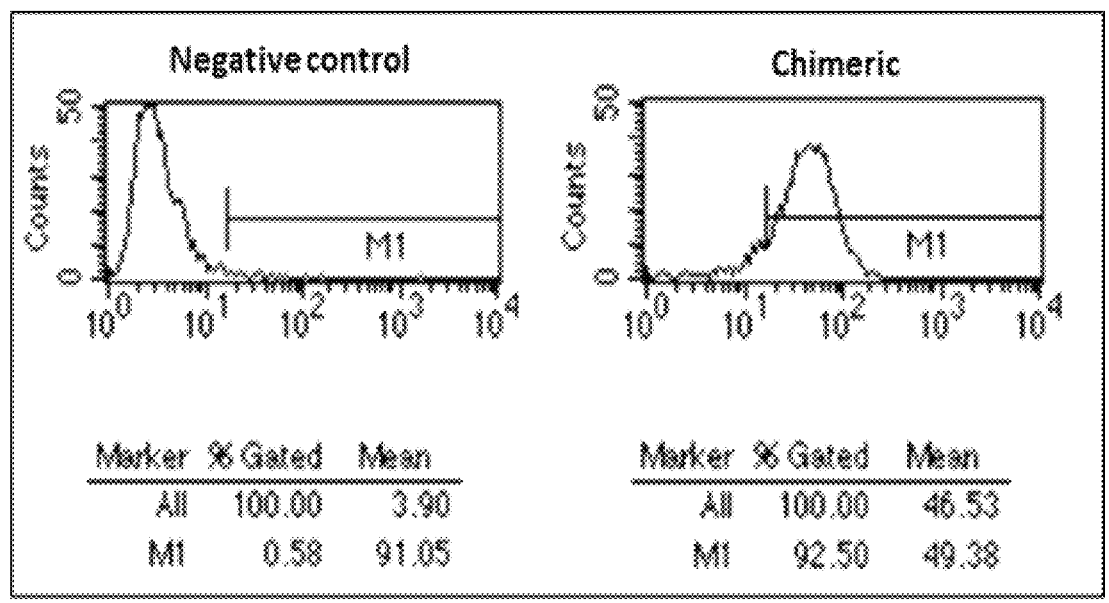
FIG. 1 is a result of confirming the binding of the chimeric antibody SI9 prepared in one example to Du145 cells, the ICAM-1 expressing cell line, by flow cytometry.
Figure 2A:
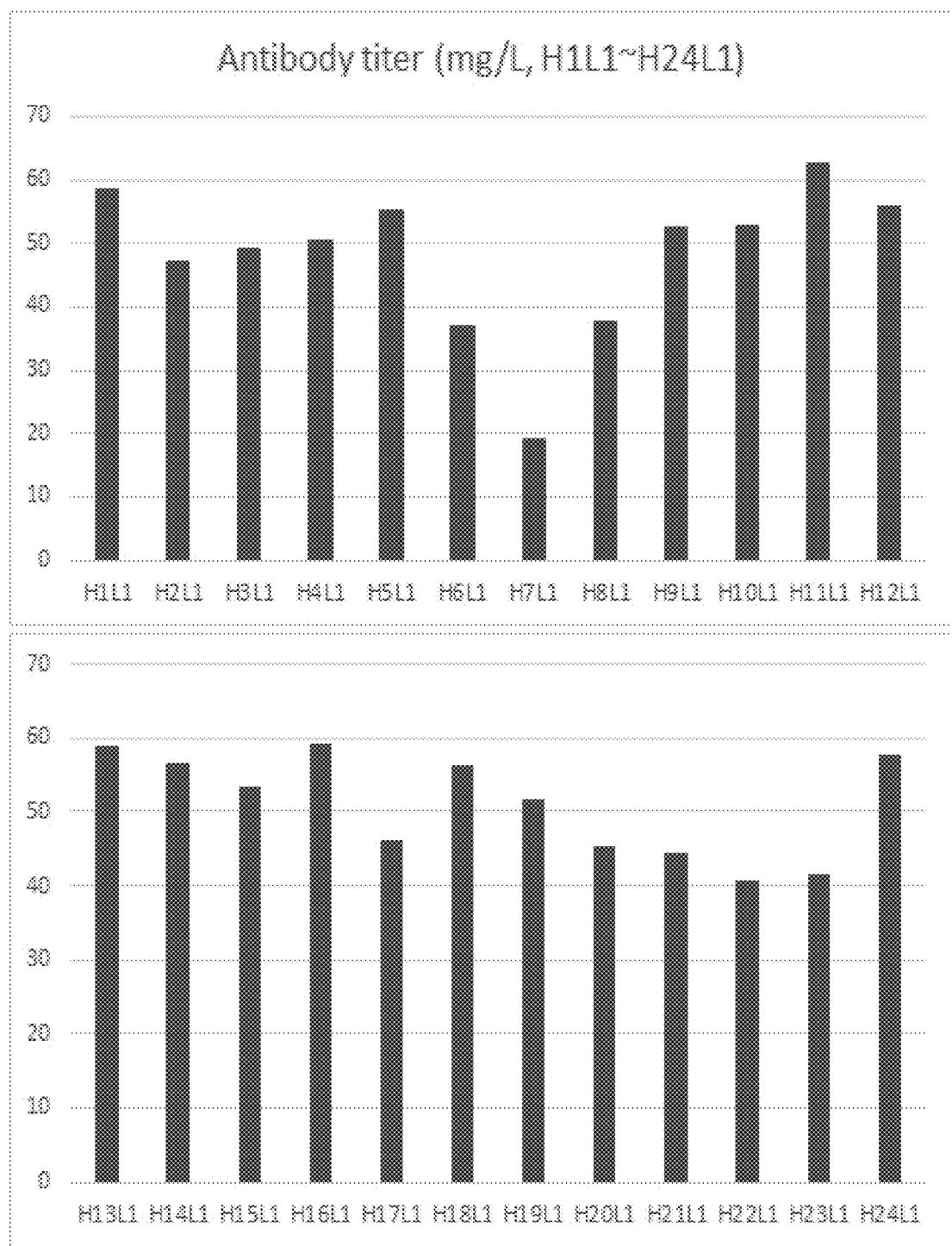
FIG. 2a to 2d are graphs showing results of quantifying purified antibodies by measuring OD (optical density) at 280 nm in one example.
Figure 2B:
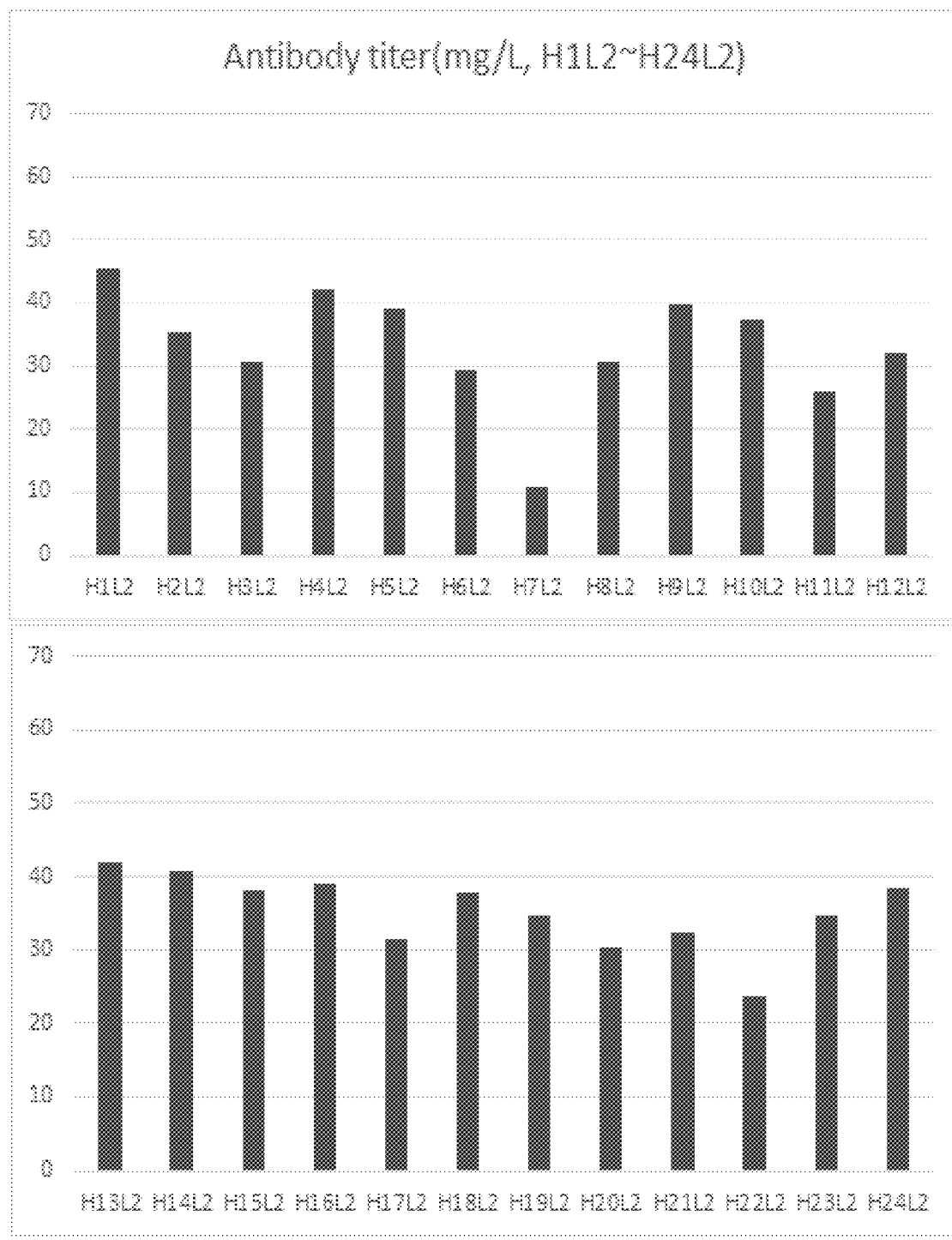
Figure 2C:
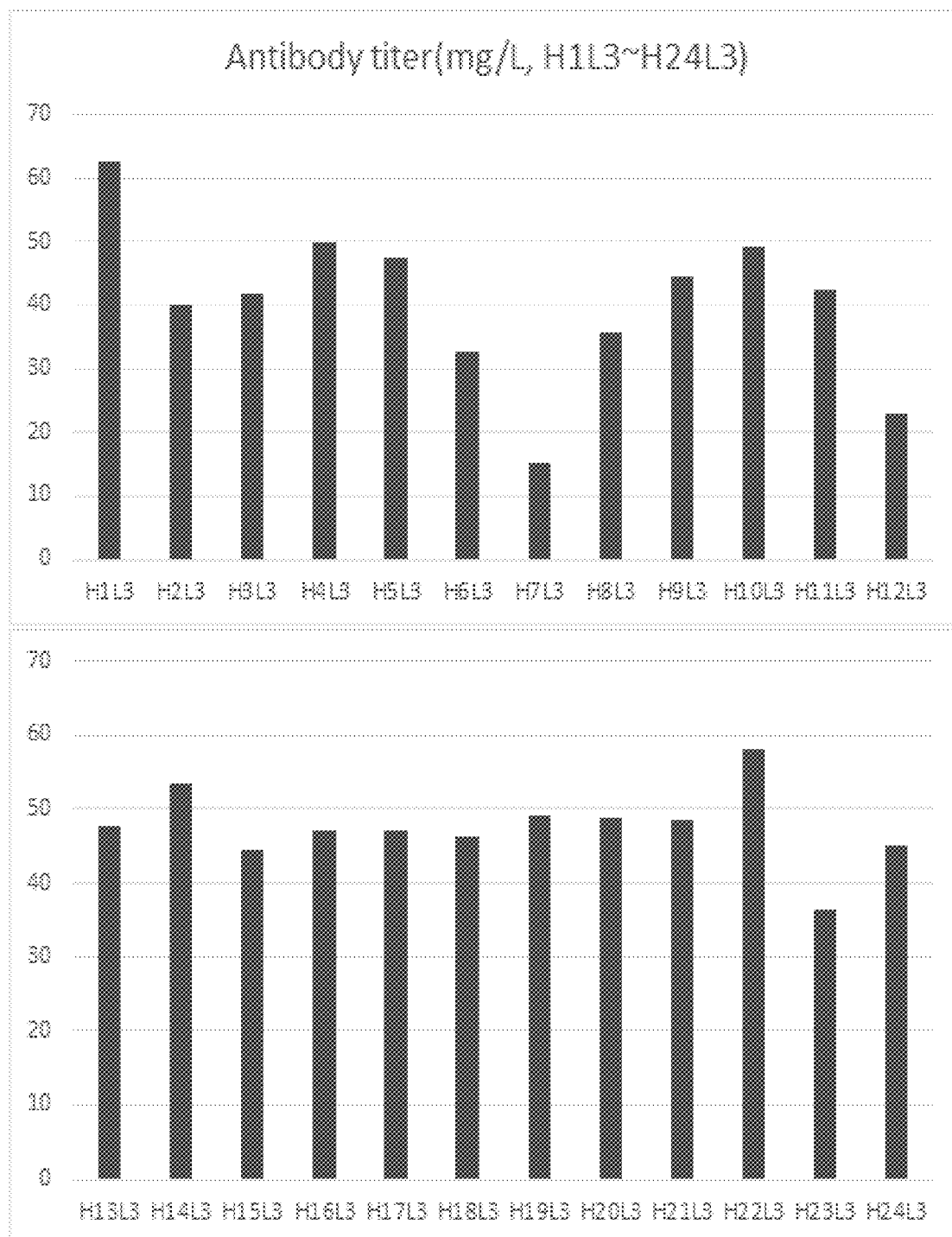
Figure 2D:
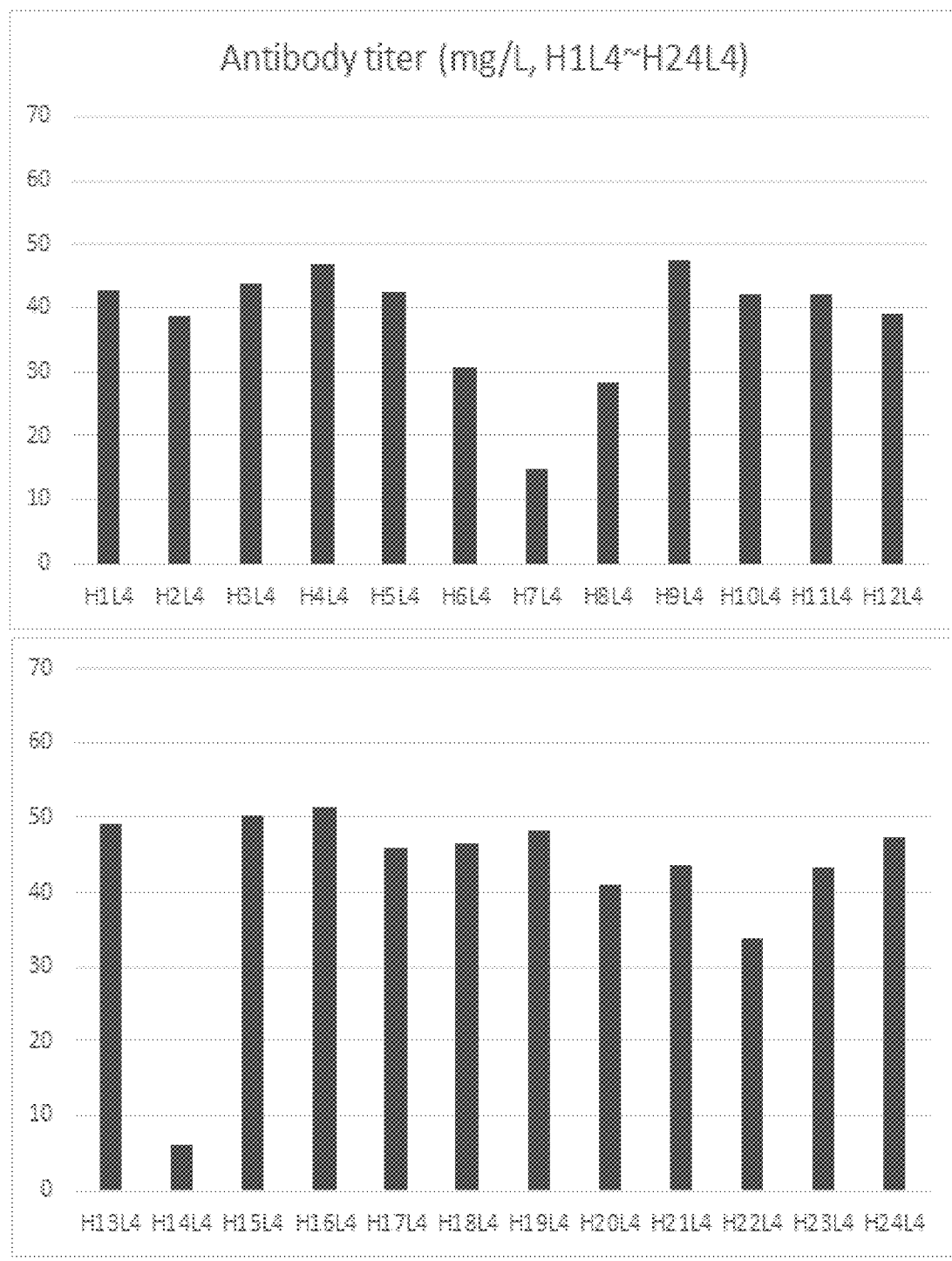
Figure 3A:
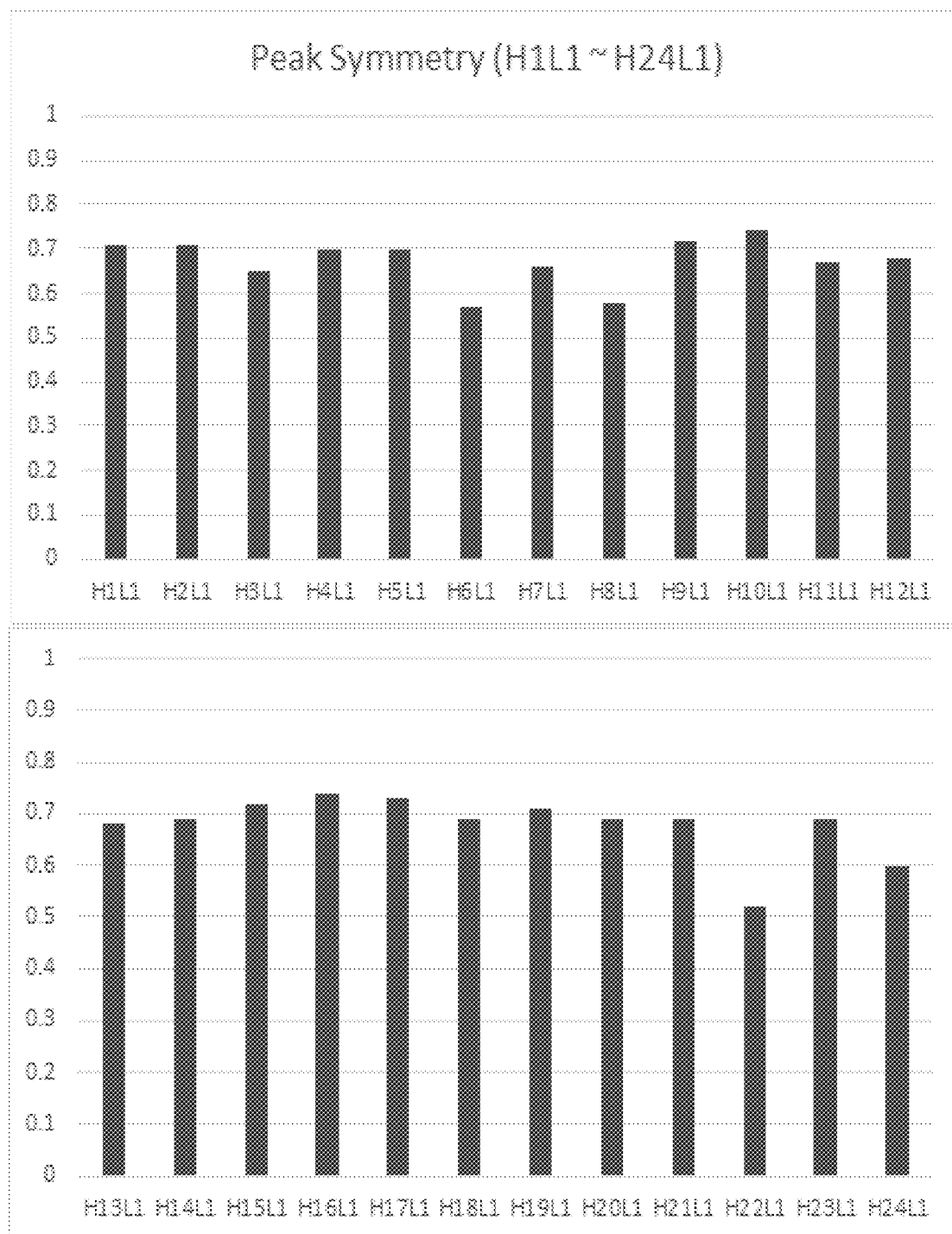
FIG. 3a to 3d are graphs showing the results of measuring the peak symmetry factor by performing size exclusion HPLC (hereinafter, SE-HPLC) analysis on the anti-ICAM-1 antibody obtained according to one example.
Figure 3B:
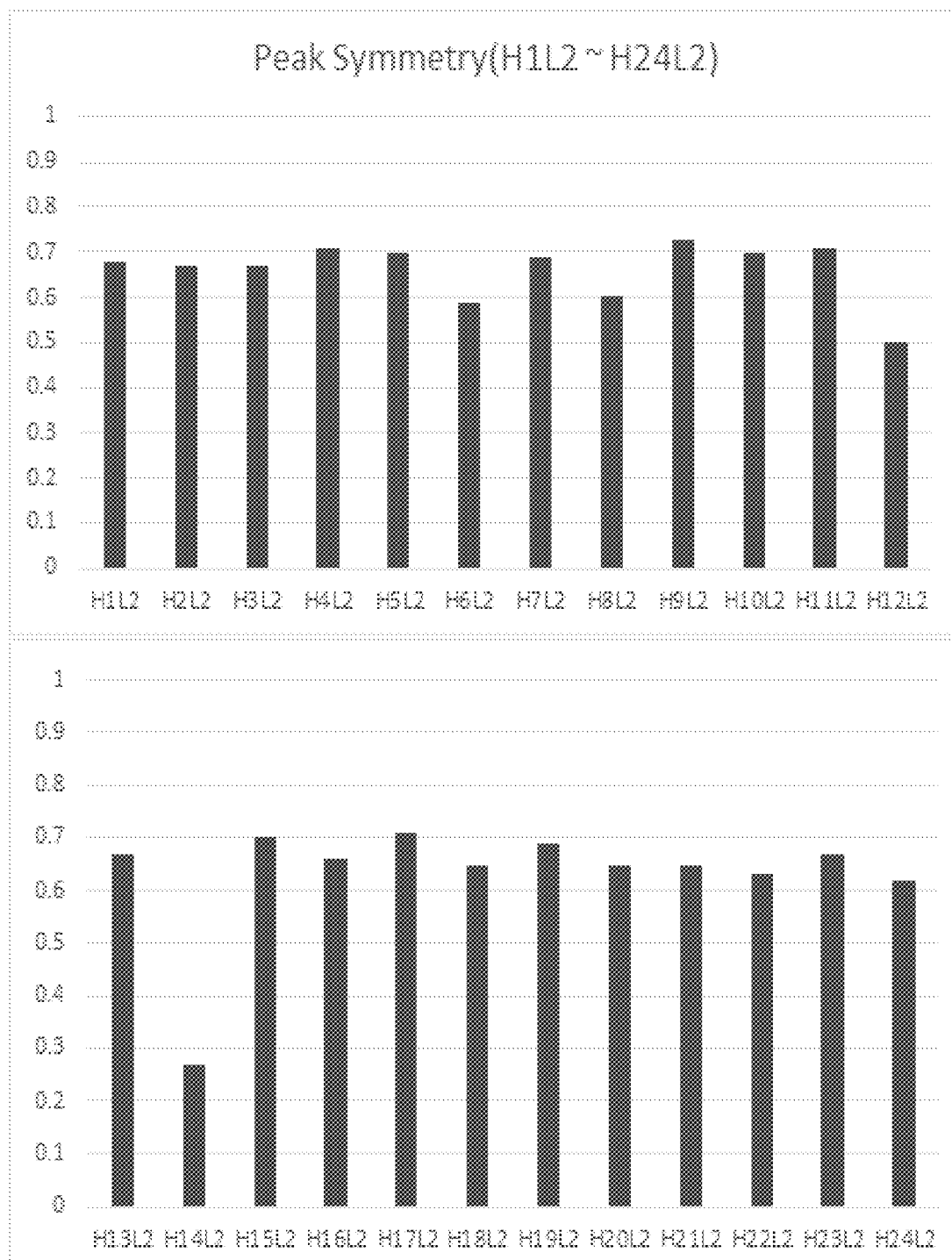
Figure 3C:
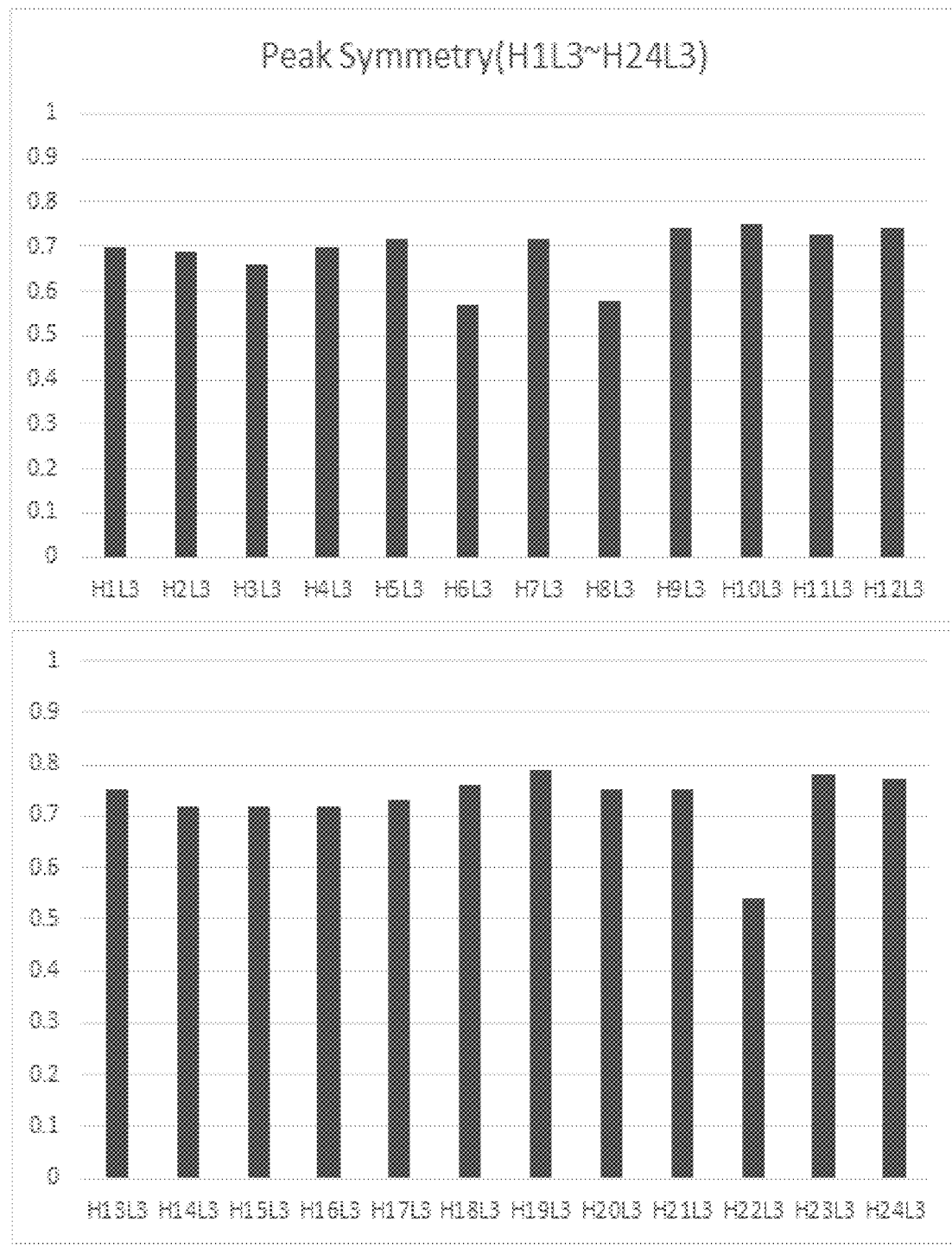
Figure 3D:
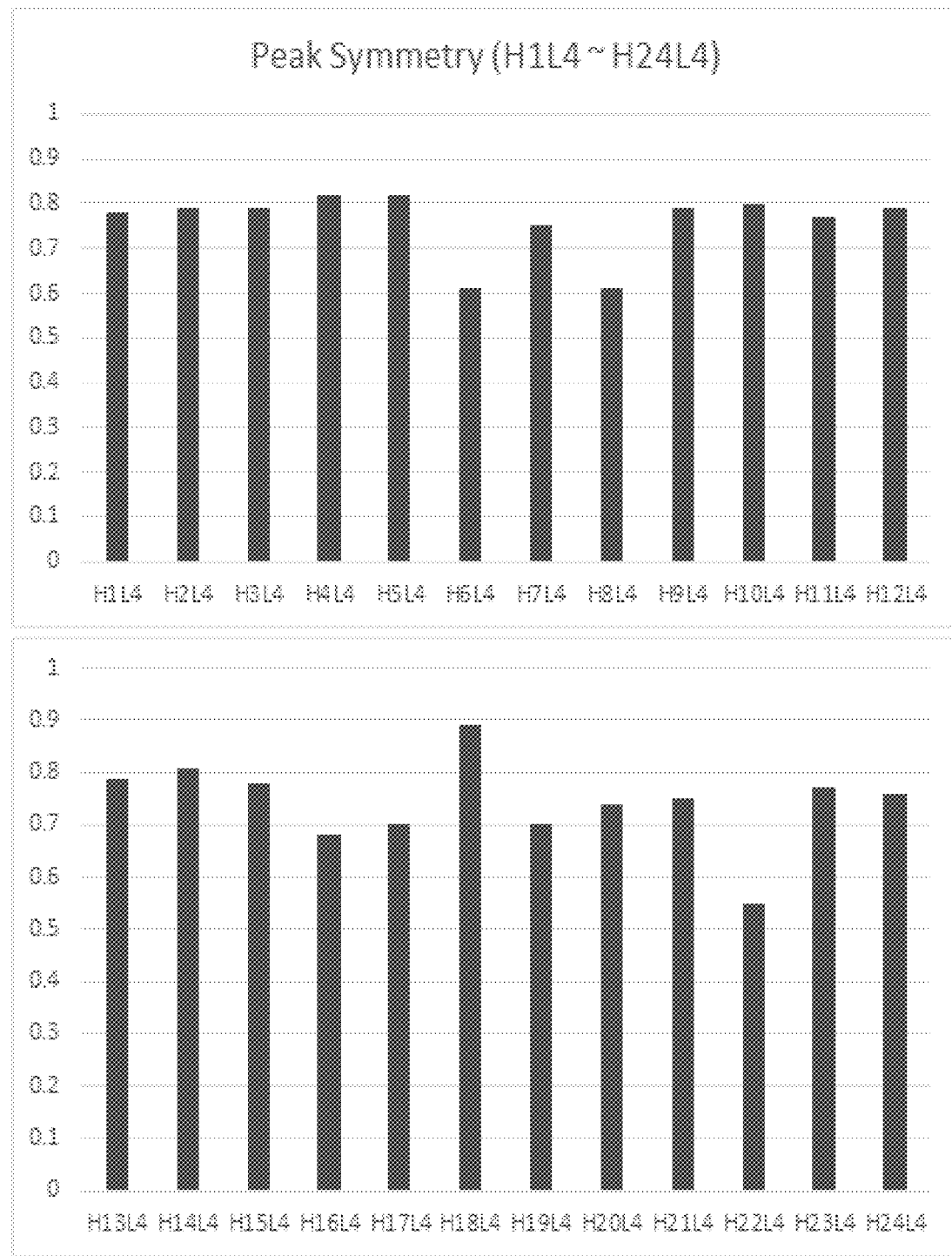
Figure 4A:
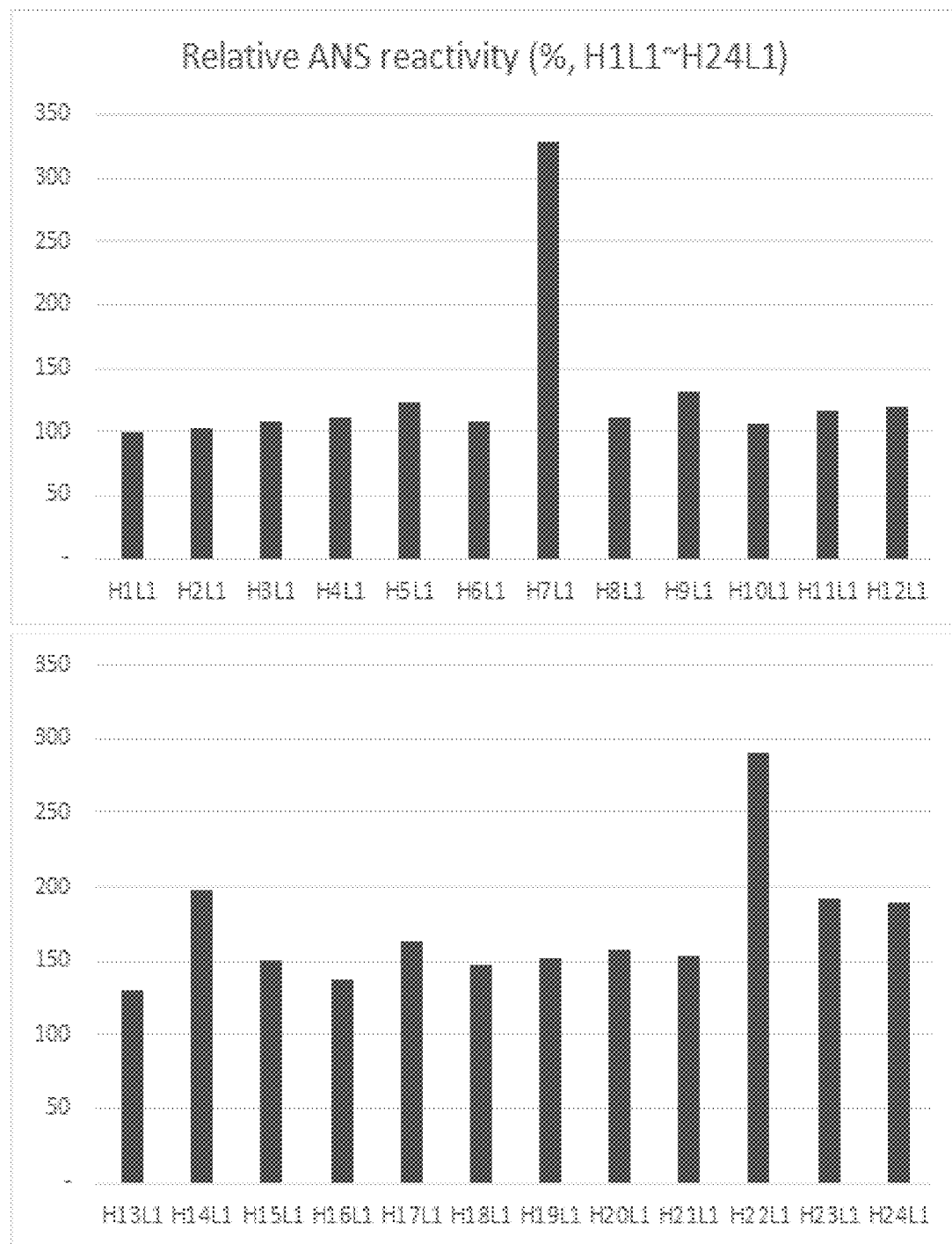
FIG. 4a to 4d are graphs showing the results of measuring the fluorescence change by the ANS reagent while leaving the anti-ICAM-1 antibody obtained according to one example at 61° C. for 1 hour.
Figure 4B:
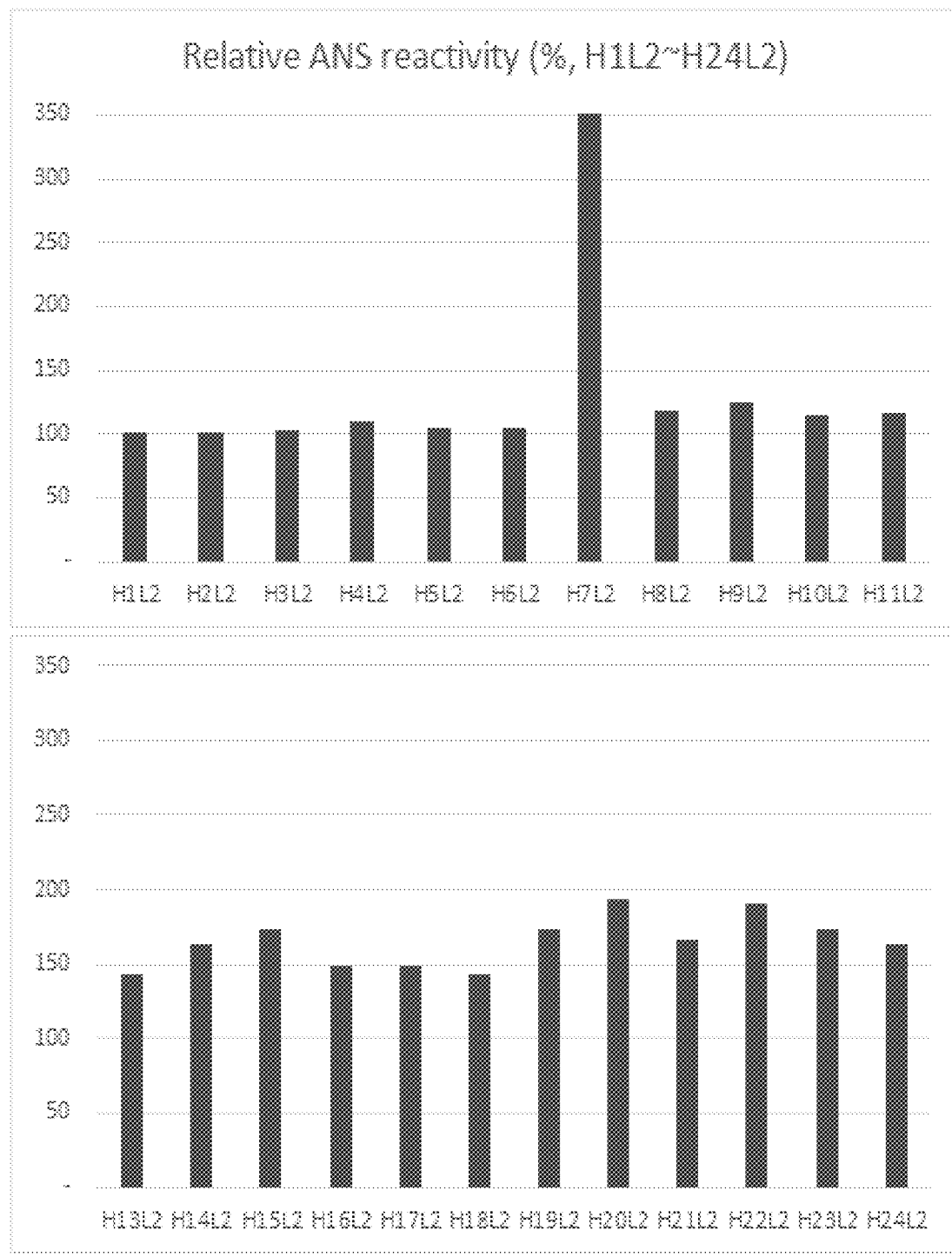
Figure 4C:
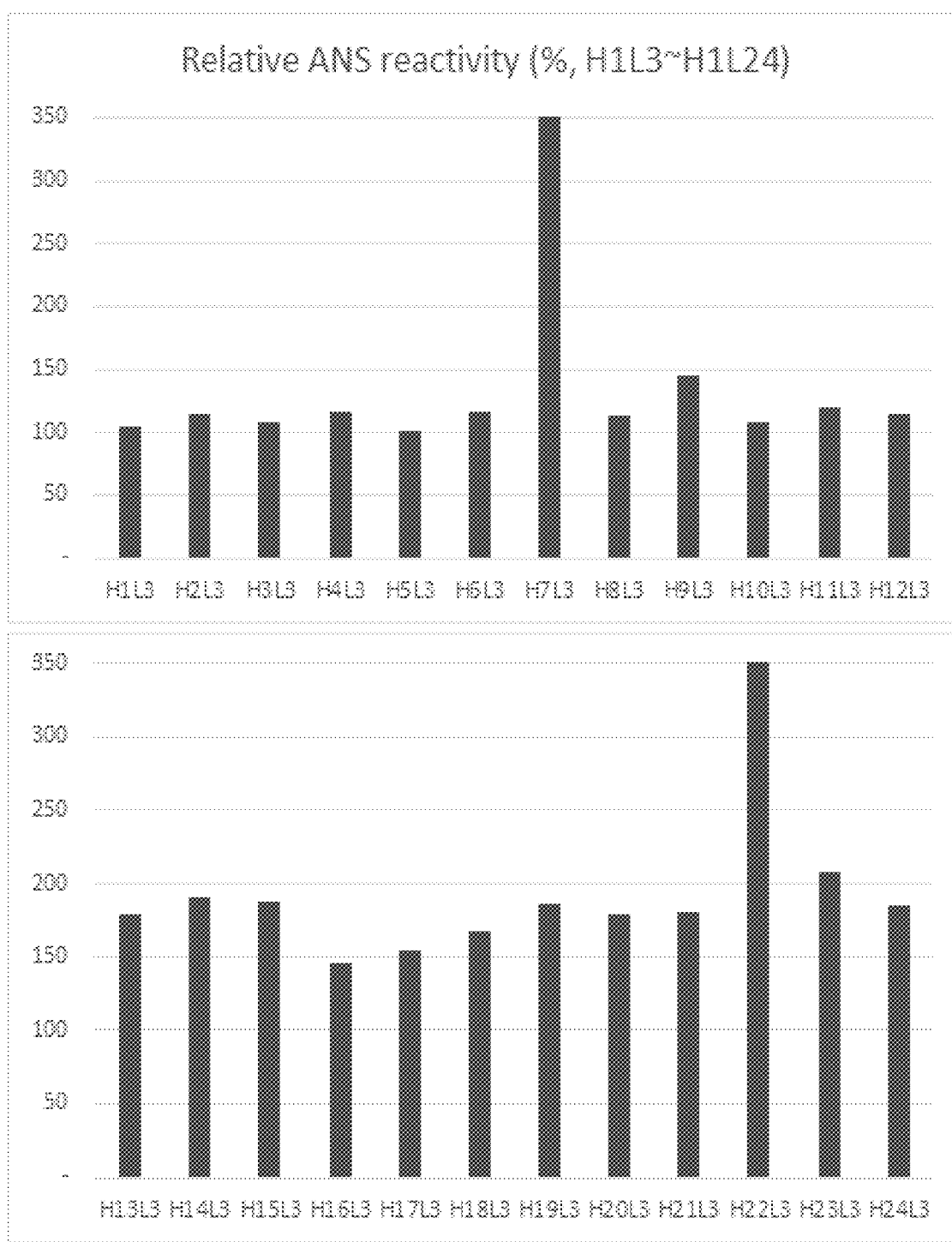
Figure 4D:
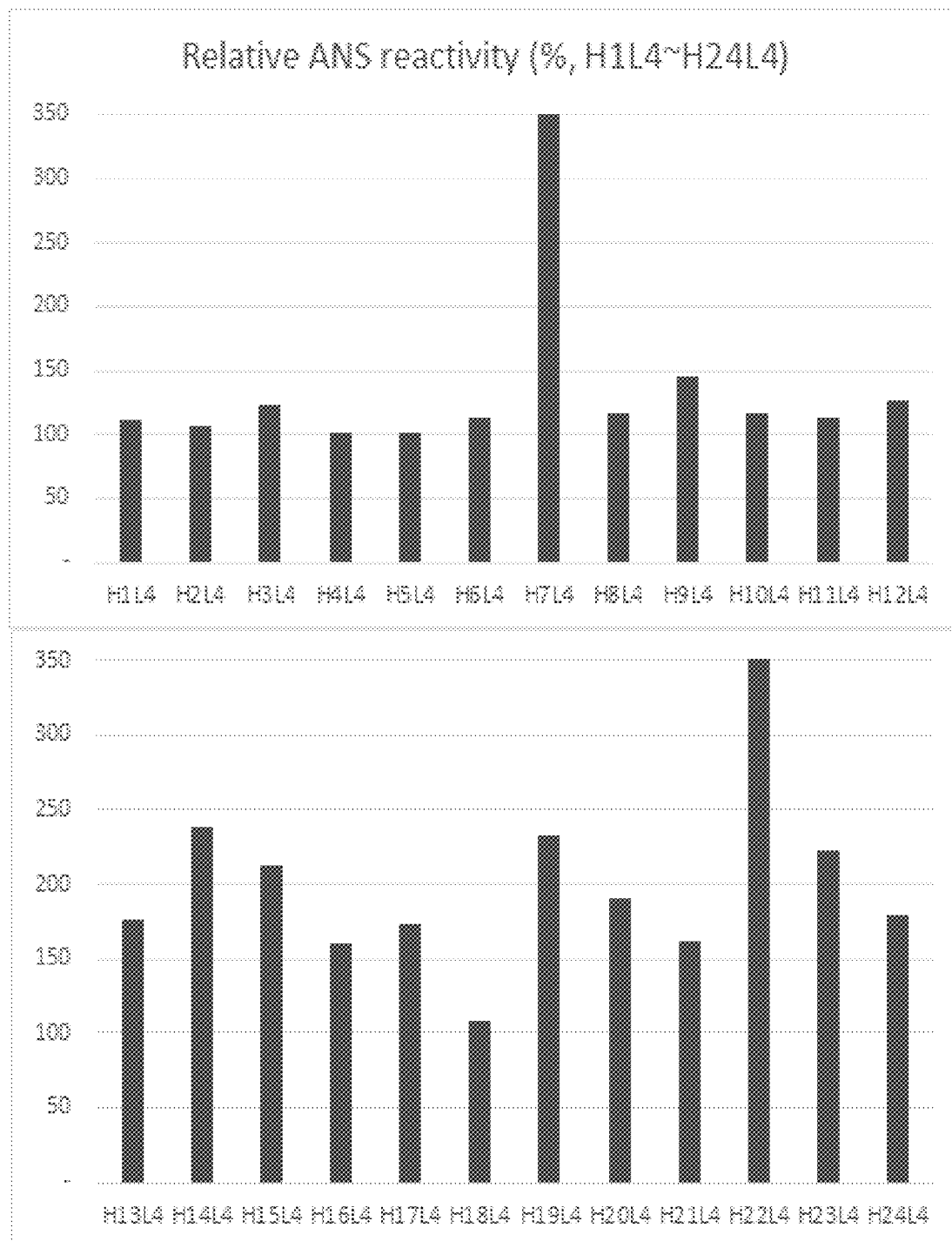

Hereinafter, the present invention will be described in more detail by way of examples, but this is only illustrative and is not intended to limit the scope of the present invention.

<Example 1> Preparation of Mouse Anti-ICAM-1 Monoclonal Antibody

In order to develop an antibody specific for ICAM-1, the following experiment was performed.

1-1: Mouse Immunity

Recombinant human ICAM-1 protein (0.5 mg/ml; NCBI accession number NP_000192.2) was mixed with an equal volume of adjuvant (Invivogen, #vac-adx-10) to prepare an immune substance. A 6-week-old Balb/c female mouse intraperitoneal cavity (IP) was injected with 200 uL of the prepared immune substance three times at intervals of 3 weeks.

1-2: Preparation of Mouse Anti ICAM-1 Monoclonal Antibody

The spleen of the immunized mouse as described above was excised to obtain a single cell suspension. The obtained cells were washed twice with RPMI (GIBCO, #21875034), and then mixed with 0.4% (w/v) trypan blue (sigma) at 1:1 (v/v), and then then the number of cells was counted by staining with trypan blue (Sigma-aldrich, #T8154). The X63 mouse myeloma cell line (ATCC CRL-1580) was washed, counted, and used as a cell fusion partner.

The myeloma cells and splenocytes were mixed at a ratio of 1:5, and the supernatant was removed after centrifugation. 1 ml of 50% (w/v) PEG (polyethylene glycol) 1500 preheated to 37° C. was slowly added over 1 minute. After holding for about 1 minute, RPMI medium was slowly added and diluted stepwise. After centrifugation, it was suspended in RPMI (20% FBS, hypoxanthine-aminopterin-thymidine; Gibco) containing 1×HAT (hypoxanthine, aminopterin, thymidine), dispensed into a 96-well plate at 150 uL/well, and then cultured in a 37° C. 5% $CO_2$ incubator.

After the fusion, HAT feeding was performed for a certain period of time, and when a well formed colony was observed, 150 uL of HT medium (hypoxanthine, thymidine) was added and cultured in a 37° C. 5% $CO_2$ incubator for 48 hours.

100 uL of the cultured medium was taken from a hybridoma culture 96-well plate to confirm whether or not ICAM-1 was reactive. ICAM-1 (R&D system, #ADP4-050) was diluted in PBS at a concentration of 1.0 ug (microgram)/ml, then dispensed into Nunc-immunoplate (Thermo, #439454) at 100 uL/well, stored in a 37° C. incubator for 1 hour, and coated. After completely removing the coating solution, 1× casein blocking solution (sigma-aldrich, #B6429) was dispensed at 200 uL/well and stored in a 37° C. incubator for 1 hour to perform blocking. After completely removing the blocking solution, the hybridoma cultured solution was dispensed at 100 uL/well and stored in a 37° C. incubator for 1 hour to induce an antigen/antibody reaction. After completely removing the cultured solution, it was washed three times with a washing solution (0.02% Tween 20 in PBS). The secondary antibody Goat anti-mouse IgG-HRP (Jackson, #) was diluted in a blocking solution at a ratio of 1:10,000 (v/v), dispensed at 100 uL/well, and stored in a 37° C. incubator for 30 minutes to induce a secondary antibody reaction. After washing three times, TMB (Thermo, #) was dispensed at 80 uL/well to induce color development and then 1.0 N sulfuric acid ($H_2SO_4$) was added to terminate the reaction. Flow cytometry was additionally performed to confirm whether the obtained anti-ICAM-1 antibody recognized ICAM-1 expressed on the cell surface. To the prostate cancer cell line Du145 (ATCC, #HTB-81) $1 \times 10^6$ cells expressing ICAM-1, 100 uL of the cultured solution was added and allowed to stand at room temperature for 15 minutes to induce antibody binding. After washing by adding PBS, 100 ul of the secondary antibody Goat anti-Mouse IgG-FITC (Jackson, #) diluted in PBS at a ratio of 1:100 (v/v) was added and reacted at room temperature for 10 minutes. After washing was performed to remove the unreacted secondary antibody, reactivity was confirmed by flow cytometry. As in the above-described test method, a positive antibody that binds to the ICAM-1 antigen was first selected, and a monoclonal antibody capable of fluorescent staining in the Du145 cell line was additionally selected. The selected monoclonal antibody (named SI9) exhibited high reactivity to the ICAM-1 protein antigen and the property of effectively binding to the surface of the Du145 cell line.

<Example 2> Preparation of Chimeric Anti-ICAM-1 Monoclonal Antibody 2-1. Anti-ICAM-1 Antibody Gene Sequence Cloning The gene of the mouse monoclonal antibody SI9 selected in Example 1 was cloned using Mouse Ig-Primer Set (Millipore, Cat. #: 69831). The monoclonal antibody SI9-producing hybridoma developed in Example 1 was cultured, and total RNA was extracted from the fusion cell line. PCR was performed using the RNA extracted using Mouse Ig-Primer Set as a template, and after inserting it into the pGem-T vector (Promega, Cat. #: A3600), the DNA sequence was confirmed through sequencing, and the mouse antibody gene was identified through the IMGT site (www.imgt.org). The heavy and light chain variable region amino acid sequences and coding nucleic acid sequences of the analyzed SI9 antibody are summarized in Table 1:

TABLE 1

| name | Sequence | SEQ ID NO |
|---|---|---|
| SI9 Chimeric $V_H$-CDR1 | GYTFTDYA | 1 |
| SI9 Chimeric $V_H$-CDR2 | ISTYSGNT | 2 |
| SI9 Chimeric $V_H$-CDR3 | ARSLYFGSSGFDY | 3 |
| SI9 Chimeric $V_L$-CDR1 | QTLVYRNGNTY | 4 |
| SI9 Chimeric $V_L$-CDR2 | KVS | 5 |
| SI9 Chimeric $V_L$-CDR3 | SQNTHFPYT | 6 |
| SI9 Chimeric $V_H$ (amino acid sequence) | QVQLQQSGAELVRPGVSVKISCKGSGYTFTDYALHW VKQSHAKSLEWIGVISTYSGNTDYNQKFRGKATMTV DKSSTTAYLELARLTSEDSAIHYCARSLYFGSSGFDY WGQGTALTVSS | 7 |
| SI9 Chimeric $V_L$ (amino acid sequence) | DVVLTQTPLSLPVNLGDQASISCRSSQTLVYRNGNTY LHWYLQKAGQSPKLLIYKVSNRFSGVPDRFSGSGSGT DFTLKISRVEAEDLGVYFCSQNTHFPYTFGGGTKIKR | 8 |
| SI9 Chimeric $V_H$ (coding nucleic acid sequence) | caggtgcagctgcagcagagcggcgcggaactggtgcgcccgggcgtgagcgtg aaaattagctgcaaaggcagcggctataccttaccgattatgcgctgcattgggtga aacagagccatgcgaaaagcctggaatggattggcgtgattagcacctatagcggc aacaccgattataaccagaaatttcgcggcaaagcgaccatgaccgtggataaag cagcaccaccgcgtatctggaactggcgcgcctgaccagcgaagatagcgcgattc attattgcgcgcgcagcctgtattttggcagcagcggctttgattattggggccaggg caccgcgctgaccgtgagcagctaa | 9 |

TABLE 1-continued

| name | Sequence | SEQ ID NO |
|---|---|---|
| SI9 Chimeric V_L (coding nucleic acid sequence) | gatgtggtgctgacccagaccccgctgagcctgccggtgaacctgggcgatcagg cgagcattagctgccgcagcagccagacectggtgtatcgcaacggcaacacctat ctgcattggtatctgcagaaagcgggccagagcccgaaactgctgatttataaagtg agcaaccgctttagcggcgtgccggatcgctttagcggcagcggcagcggcaccg attttaccctgaaaattagccgcgtggaagcggaagatctgggcgtgtattttgcagc cagaacacccattttccgtatacctttggcggcggcaccaaaattaaacgc | 10 |

2-2. Preparation of Chimeric Antibody

Based on the amino acid sequence of the prepared anti-ICAM-1 mouse antibody SI9 above, an anti-ICAM-1 chimeric antibody was prepared.

2-2-1. Plasmid Construction

For expression of the anti-ICAM-1 chimeric antibody, a plasmid for heavy chain expression and a plasmid for light chain expression were prepared, respectively. The plasmid for light chain expression was prepared using the pOptiVEC (Invitrogen) vector, and the plasmid for heavy chain expression was prepared using the pcDNA3.3 (Invitrogen) vector.

In order to express each variable region coding cDNA and constant region coding cDNA of the antibody as a continuous amino acid sequence without additional amino acid insertion, each of the genes obtained by linking the cloned variable region coding nucleic acid sequence (see Table 1) with the known human IgG4 constant region (heavy chain; GenBank_AIC59040.1) coding nucleic acid sequence or the kappa constant region (light chain; GenBank_AAA58989.1) coding nucleic acid sequence was synthesized (Bioneer). The "CPSCP" sequence of the middle hinge region of the light chain constant region was further modified to "CPPCP" like the IgG1 isotype to prevent antibody shuffling. The heavy and light chain expression genes synthesized as described above were cut with restriction enzymes Xho I and Sal I, and then the light chain expression gene was ligated to the pOptiVec vector, and the heavy chain expression gene was ligated to the pcDNA3.3 vector, respectively, thereby constructing a plasmid for complete antibody expression. (pcDNA3.3-anti-ICAM-1 heavy chain expression plasmid and pOptiVEC-anti-ICAM-1 light chain expression plasmid).

2-2-2. Transformation

The prepared pcDNA3.3-anti-ICAM-1 heavy chain expression plasmid and pOptiVEC-anti-ICAM-1 light chain expression plasmid were transfected into DG44 cells (Invitrogen) derived from CHO cells to perform a transformation process.

First, 3 days before transfection, suspended DG44 cells were cultured in MEMa medium containing 5% FBS to induce adherent cells. Transformation was performed in a 6 well plate using ViaFect transfection regent (Promega, Cat. #: E4981). One day before transformation, DG44 cells adapted to adherent state were prepared by subculture at a concentration of 1×10⁵ cells/well. And the amount of DNA used for transformation was used in a combination of 1:2 ratio of pcDNA3.3-anti-ICAM-1 heavy chain expression plasmid and pOptiVEC-anti-ICAM-1 light chain expression plasmid, respectively, 1.0 μg and 2.0 μg. Transformation was carried out for 48 hours. The transformed cell population was analyzed using a flow cytometer, and the results are shown in FIG. 1. As shown in FIG. 1, it is possible to confirm the binding phenomenon of the chimeric antibody obtained by inserting the variable region coding gene of the mouse SI9 antibody into the constant region coding gene of the human antibody, to the ICAM-1 expressing cell line.

<Example 3> Preparation of Humanized Anti-ICAM-1 Antibody

3.1 Recombinant Antibody Sequence Selection by in Silico Humanization

The humanized antibody sequence obtained by recombining the germline framework region encoding the human antibody gene while maintaining the amino acid sequence of each of the heavy and light chain CDRs (CDRH1: GYTFTDYA (SEQ ID NO: 1), CDRH2: ISTYSGNT (SEQ ID NO: 2), CDRH3: ARSLYFGSSGFDY (SEQ ID NO: 3), CDRL1: QTLVYRNGNTY (SEQ ID NO: 4), CDRL2: KVS (SEQ ID NO: 5), CDRL3: SQNTHFPYT (SEQ ID NO: 6) of the chimeric ICAM-1 antibody (SI9) was selected in silico method.

As a result, as humanized DNP007 antibody sequences, 24 kinds of heavy chain variable regions and 4 kinds of light chain variable regions were selected, respectively. The amino acid sequences of the heavy chain variable region, light chain variable region, CDR, and framework of the selected humanized antibody are shown in Tables 2, 3, 4, and 5 below. In Tables 2 and 3 below, the regions in bold underlined are the amino acid sequences of the CDRs (CDR1, CDR2, and CDR3 in order).

TABLE 2

Heavy chain variable region sequence of humanized DNP007 antibody

| classification | name | Amino aicd sequence | SEQ ID NO |
|---|---|---|---|
| | VH1 | QVQLVQSGAEVKKPGASVKISCKGSGYTFTDYA HWVRQAPGQRLEWIGVISTYSGNTDYNQKFRGRA TITRDTSASTAYMELSSLRSEDTAVYYCARSLYFG SSGFDYWGQGTALTVSS | 11 |

TABLE 2-continued

Heavy chain variable region sequence of humanized DNP007 antibody

| classification name | Amino acid sequence | SEQ ID NO |
|---|---|---|
| VH2 | QVQLVQSGAEVKKPGASVKVSCKGSGYTFTDYALHWVRQAPGQRLEWMGVISTYSGNTDYNQKFRGRVTMTVDTSASTAYMELSSLRSEDTAVHYCARSLYFGSSGFDYWGQGTALTVSS | 12 |
| VH3 | QVQLVQSGAEVKKPGASVKVSCKASGYTFTDYALHWVRQAPGQRLEWMGVISTYSGNTDYNQKFRGRATITRDKSASTAYLELSSLRSEDTAVHYCARSLYFGSSGFDYWGQGTALTVSS | 13 |
| VH4 | QVQLVQSGAEVKKPGASVKVSCKASGYTFTDYALHWVRQAPGQRLEWIGVISTYSGNTDYNQKFRGRVTMTRDTSATTAYLELSSLRSEDTAVYYCARSLYFGSSGFDYWGQGTALTVSS | 14 |
| VH5 | QVQLVQSGAEVKKPGASVKISCKASGYTFTDYALHWVRQAPGQRLEWMGVISTYSGNTDYNQKFRGRVTITVDKSATTAYMELSSLRSEDTAVYYCARSLYFGSSGFDYWGQGTALTVSS | 15 |
| VH6 | QVQLVQSGAEVVKPGASVKVSCKGSGYTFTDYALHWVRQAPGQRLEWIGVISTYSGNTKYSQKFQGKATITRDKSASTAYLELSSLRSEDTAVYYCARSLYFGSSGFDYWGQGTALTVSS | 16 |
| VH7 | QVQLVQSGAEVKKPGASVKVSCKGSGYTFTDYALHWVKQAPGQRLEWMGVISTYSGNTKYSQKFQGRATMTRDTSATTAYMELSSLRSEDTAIHYCARSLYFGSSGFDYWGQGTALTVSS | 17 |
| VH8 | QVQLQQSGAEVKKPGASVKISCKGSGYTFTDYALHWVRQAPGQSLEWMGVISTYSGNTKYSQKFQGRATMTRDKSASTAYMELSSLRSEDTAVYYCARSLYFGSSGFDYWGQGTALTVSS | 18 |
| VH9 | QVQLQQSGAEVVKPGASVKVSCKASGYTFTDYALHWVRQAPGQSLEWMGVISTYSGNTKYSQKFQGKVTITVDKSATTAYMELSSLRSEDTAVHYCARSLYFGSSGFDYWGQGTALTVSS | 19 |
| VH10 | QVQLQQSGAEVVKPGASVKISCKASGYTFTDYALHWVKQAPGQSLEWMGVISTYSGNTKYSQKFQGRVTITVDTSATTAYLELSSLRSEDTAIYYCARSLYFGSSGFDYWGQGTALTVSS | 20 |
| VH11 | QVQLQQSGAEVKKPGASVKISCKASGYTFTDYALHWVRQAPGQRLEWIGVISTYSGNTKYSQKFQGKVTITRDTSASTAYLELSSLRSEDTAIHYCARSLYFGSSGFDYWGQGTALTVSS | 21 |
| VH12 | QVQLQQSGAEVKKPGASVKVSCKASGYTFTDYALHWVKQAPGQRLEWIGVISTYSGNTKYSQKFQGRVTMTVDKSATTAYMELSSLRSEDTAVYYCARSLYFGSSGFDYWGQGTALTVSS | 22 |
| VH13 | QVQLVQSGAEVKKPGASVKISCKGSGYTFTDYALHWVRQAPGQRLEWMGVISTYSGNTDYNQKFRGRVTITRDKSASTAYLELSSLRSEDTAVYYCARSLYFGSSGFDYWGQGTALTVSS | 23 |
| VH14 | QVQLVQSGAEVKKPGASVKVSCKGSGYTFTDYALHWVRQAPGQRLEWMGVISTYSGNTDYNQKFRGRVTITVDTSATTAYMELSSLRSEDTAVHYCARSLYFGSSGFDYWGQGTALTVSS | 24 |
| VH15 | QVQLVQSGAEVKKPGASVKVSCKGSGYTFTDYALHWVRQAPGQRLEWIGVISTYSGNTDYNQKFRGRVTMTRDTSASTAYMELSSLRSEDTAVHYCARSLYFGSSGFDYWGQGTALTVSS | 25 |
| VH16 | QVQLVQSGAEVKKPGASVKVSCKGSGYTFTDYALHWVRQAPGQRLEWMGVISTYSGNTDYNQKFRGRATMTRDTSASTAYLELSSLRSEDTAVYYCARSLYFGSSGFDYWGQGTALTVSS | 26 |
| VH17 | QVQLVQSGAEVKKPGASVKISCKGSGYTFTDYALHWVRQAPGQRLEWMGVISTYSGNTDYNQKFRGRATITVDTSASTAYMELSSLRSEDTAVYYCARSLYFGSSGFDYWGQGTALTVSS | 27 |
| VH18 | QVQLVQSGAEVKKPGASVKVSCKGSGYTFTDYALHWVRQAPGQRLEWIGVISTYSGNTDYNQKFRGRVTITRDKSATTAYMELSSLRSEDTAVYYCARSLYFGSSGFDYWGQGTALTVSS | 28 |

TABLE 2-continued

Heavy chain variable region sequence of humanized DNP007 antibody

| classification | name | Amino aicd sequence | SEQ ID NO |
|---|---|---|---|
| | VH19 | QVQLVQSGAEVKKPGASVKISCKGSGYTFTDYALHWVRQAPGQRLEWIGVISTYSGNTKYSQKFQGRATITVDTSATTAYLELSSLRSEDTAVYYCARSLYFGSSGFDYWGQGTALTVSS | 29 |
| | VH20 | QVQLVQSGAEVKKPGASVKISCKGSGYTFTDYALHWVRQAPGQRLEWIGVISTYSGNTKYSQKFQGRATMTRDTSASTAYLELSSLRSEDTAVHYCARSLYFGSSGFDYWGQGTALTVSS | 30 |
| | VH21 | QVQLVQSGAEVKKPGASVKVSCKGSGYTFTDYALHWVRQAPGQRLEWIGVISTYSGNTKYSQKFQGRVTMTVDKSATTAYLELSSLRSEDTAVYYCARSLYFGSSGFDYWGQGTALTVSS | 31 |
| | VH22 | QVQLVQSGAEVKKPGASVKISCKGSGYTFTDYALHWVRQAPGQRLEWMGVISTYSGNTKYSQKFQGRATMTRDKSATTAYMELSSLRSEDTAVHYCARSLYFGSSGFDYWGQGTALTVSS | 32 |
| | VH23 | QVQLVQSGAEVKKPGASVKVSCKGSGYTFTDYALHWVRQAPGQRLEWMGVISTYSGNTKYSQKFQGRATMTVDKSASTAYLELSSLRSEDTAVHYCARSLYFGSSGFDYWGQGTALTVSS | 33 |
| | VH24 | QVQLVQSGAEVKKPGASVKISCKGSGYTFTDYALHWVRQAPGQRLEWIGVISTYSGNTKYSQKFQGRVTITVDKSATTAYMELSSLRSEDTAVHYCARSLYFGSSGFDYWGQGTALTVSS | 34 |

TABLE 3

Light chain variable region sequence of humanized DNP007 antibody

| classification | name | Amino aicd sequence | SEQ ID NO |
|---|---|---|---|
| VL | VL1 | DVVLTQSPLSLPVTLGQPASISCRSSQTLVYRNGNTYLHWYQQRPGQSPRLLIYKVSNRFSGVPDRFSGSGSGTDFTLKISRVEAEDVGVYFCSQNTHFPYTFGGGTKLEIK | 35 |
| | VL2 | DVVLTQSPLSLPVTLGQPASISCRSSQTLVYRNGNTYLHWYQQRAGQSPRLLIYKVSNRFSGVPDRFSGSGSGTDFTLKISRVEAEDVGVYFCSQNTHFPYTFGGGTKLEIK | 36 |
| | VL3 | DVVLTQTPLSSPVTLGQPASISCRSSQTLVYRNGNTYLHWYLQRAGQPPRLLIYKVSNRFSGVPDRFSGSGAGTDFTLKISRVEAEDVGVYFCSQNTHFPYTFGGGTKLEIK | 37 |
| | VL4 | DVVLTQTPLSSPVTLGQPASISCRSSQTLVYRNGNTYLHWYQQRPGQPPRLLIYKVSNRFSGVPDRESGSGAGTDFTLKISRVEAEDVGVYFCSQNTHFPYTFGGGTKLEIK | 38 |

TABLE 4

Framework sequence of humanized DNP007 antibody heavy chain variable region

| classification | Sequence | SEQ ID NO | VH number applied |
|---|---|---|---|
| VH-FR1 | QVQLQQSGAELVRPGVSVKISCKGS | 39 | Chimeric |
| | QVQLVQSGAEVKKPGASVKISCKGS | 40 | VH1, VH13, VH17, VH19, VH20, VH22, VH24 |
| | QVQLVQSGAEVKKPGASVKVSCKAS | 41 | VH3, VH4 |
| | QVQLVQSGAEVKKPGASVKISCKAS | 42 | VH5 |
| | QVQLVQSGAEVVKPGASVKVSCKGS | 43 | VH6 |
| | QVQLVQSGAEVKKPGASVKISCKGS | 44 | VH8 |
| | QVQLQQSGAEVVKPGASVKVSCKAS | 45 | VH9 |
| | QVQLVQSGAEVVKPGASVKISCKAS | 46 | VH10 |
| | QVQLQQSGAEVKKPGASVKISCKAS | 47 | VH11 |
| | QVQLQQSGAEVKKPGASVKVSCKAS | 48 | VH12 |

TABLE 4-continued

Framework sequence of humanized DNP007 antibody heavy chain variable region

| classification | Sequence | SEQ ID NO | VH number applied |
| --- | --- | --- | --- |
| VH-FR2 | LHWVKQSHAKSLEWIGV | 49 | Chimeric |
| | LHWVRQAPGQRLEWIGV | 50 | VH1, VH4, VH6, VH11, VH15, VH18, VH19, VH20, VH21, VH24 |
| | LHWVRQAPGQRLEWMGV | 51 | VH2, VH3, VH5, VH13, VH14, VH16, VH17, VH22, VH23 |
| | LHWVKQAPGQRLEWMGV | 52 | VH7 |
| | LHWVRQAPGQSLEWMGV | 53 | VH8, VH9 |
| | LHWVKQAPGQSLEWMGV | 54 | VH10 |
| | LHWVKQAPGQRLEWIGV | 55 | VH12 |
| VH-FR3 | DYNQKFRGKATMTVDKSSTTAYLELARLTSEDSAIHYC | 56 | Chimeric |
| | DYNQKFRGRATITRDTSASTAYMELSSLRSEDTAVYYC | 57 | VH1 |
| | DYNQKFRGRVTMTVDTSASTAYMELSSLRSEDTAVHYC | 58 | VH2 |
| | DYNQKFRGRATITRDKSASTAYLELSSLRSEDTAVHYC | 59 | VH3 |
| | DYNQKFRGRVTMTRDTSATTAYLELSSLRSEDTAVYYC | 60 | VH4 |
| | DYNQKFRGRVTITVDKSATTAYMELSSLRSEDTAVYYC | 61 | VH5 |
| | KYSQKFQGKATITRDKSASTAYLELSSLRSEDTAVYYC | 62 | VH6 |
| | KYSQKFQGRATMTRDTSATTAYMELSSLRSEDTAIHYC | 63 | VH7 |
| | KYSQKFQGRATMTRDKSASTAYMELSSLRSEDTAVYYC | 64 | VH8 |
| | KYSQKFQGKVTITVDTSATTAYMELSSLRSEDTAVHYC | 65 | VH9 |
| | KYSQKFQGRVTITVDTSASTAYLELSSLRSEDTAIYYC | 66 | VH10 |
| | KYSQKFQGKVTITRDTSASTAYLELSSLRSEDTAIHYC | 67 | VH11 |
| | KYSQKFQGKVTITRDTSASTAYLELSSLRSEDTAIHYC | 68 | VH12 |
| | DYNQKFRGRVTITRDKSASTAYLELSSLRSEDTAVYYC | 69 | VH13 |
| | DYNQKFRGRVTITVDTSATTAYMELSSLRSEDTAVHYC | 70 | VH14 |
| | DYNQKFRGRVTMTRDTSASTAYMELSSLRSEDTAVHYC | 71 | VH15 |
| | DYNQKFRGRATMTRDTSASTAYLELSSLRSEDTAVYYC | 72 | VH16 |
| | DYNQKFRGRATITVDTSASTAYMELSSLRSEDTAVYYC | 73 | VH17 |
| | DYNQKFRGRVTITRDKSATTAYMELSSLRSEDTAVYYC | 74 | VH18 |
| | KYSQKFQGRATITVDTSATTAYLELSSLRSEDTAVYYC | 75 | VH19 |
| | KYSQKFQGRATMTRDTSASTAYLELSSLRSEDTAVHYC | 76 | VH20 |
| | KYSQKFQGRVTMTVDKSATTAYLELSSLRSEDTAVYYC | 77 | VH21 |
| | KYSQKFQGRATMTRDKSATTAYMELSSLRSEDTAVHYC | 78 | VH22 |
| | KYSQKFQGRATMTVDKSASTAYLELSSLRSEDTAVHYC | 79 | VH23 |
| | KYSQKFQGRVTITVDKSATTAYMELSSLRSEDTAVHYC | 80 | VH24 |

TABLE 4-continued

Framework sequence of humanized DNP007 antibody heavy chain variable region

| classification | Sequence | SEQ ID NO | VH number applied |
| --- | --- | --- | --- |
| VH-FR4 | WGQGTALTVSS | 81 | Chimeric, VH1, VH2, VH3, VH4, VH5, VH6, VH7, VH8, VH9, VH10, VH11, VH12, VH13, VH14, VH15, VH16, VH17, VH18, VH19, VH20, VH21, VH22, VH23, VH24 |

TABLE 5

Framework sequence of humanized DNP007 antibody light chain variable region

| classification | Sequence | SEQ ID NO | VL number applied |
| --- | --- | --- | --- |
| VL-FR1 | DVVLTQTPLSLPVNLGDQASISCRSS | 82 | Chimeric |
|  | DVVLTQSPLSLPVTLGQPASISCRSS | 83 | VL1, VL2 |
|  | DVVLTQTPLSSPVTLGQPASISCRSS | 84 | VL3, VL4 |
| VL-FR2 | LHWYLQKAGQSPKLLIY | 85 | Chimeric |
|  | LHWYLQKAGQSPKLLI | 86 | VL1 |
|  | LHWYQQRAGQSPRLLIY | 87 | VL2 |
|  | LHWYLQRAGQPPRLLIY | 88 | VL3 |
|  | LHWYQQRPGQPPRLLIY | 89 | VL4 |
| VL-FR3 | NRFSGVPDRFSGSGSGTDFTLKISR VEAEDLGVYFC | 90 | Chimeric, VL1 |
|  | NRFSGVPDRFSGSGSGTDFTLKISR VEAEDVGVYFC | 91 | VL2 |
|  | NRFSGVPDRFSGSGAGTDFTLKISR VEAEDVGVYFC | 92 | VL3, VL4 |
| VL-FR4 | FGGGTKIKRQ | 93 | Chimeric |
|  | FGGGTKLEIKR | 94 | VL1, VL2, VL3, VL4 |

3.2 Expression and Analysis of Humanized Recombinant Antibody

The selected antibody sequences were ligated to human IgG4 heavy chain constant region and kappa light chain constant region, respectively, and expressed in HEK293 cells (ATCC CRL-1573) in the form of human IgG4.

TABLE 6

Humanized DNP007 antibody constant region sequence

| classification | Amino ancid sequence | SEQ ID NO |
| --- | --- | --- |
| CH | ASTKGPSVFPLAPCSRSTSESTAALGCLVKDYFPEPVTV SWNSGALTSGVHTFPAVLQSSGLYSLSSVVTVPSSSLGT KTYTCNVDHKPSNTKVDKRVESKYGPPCPPCPAPEFLG GPSVFLFPPKPKDTLMISRTPEVTCVVVDVSQEDPEVQF NWYVDGVEVHNAKTKPREEQFNSTYRVVSVLTVLHQ DWLNGKEYKCKVSNKGLPSSIEKTISKAKGQPREPQVY TLPPSQEEMTKNQVSLTCLVKGFYPSDIAVEWESNGQP ENNYKTTPPVLDSDGSFFLYSRLTVDKSRWQEGNVFSC SVMHEALHNHYTQKSLSLSLGK | 95 |

TABLE 6-continued

Humanized DNP007 antibody constant region sequence

| classification | Amino ancid sequence | SEQ ID NO |
|---|---|---|
| CL | TVAAPSVFIFPPSDEQLKSGTASVVCLLNNFYPREAKVQ WKVDNALQSGNSQESVTEQDSKDSTYSLSSTLTLSKAD YEKHKVYACEVTHQGLSSPVTKSFNRGEC | 96 |

After 7 days of transfection, the humanized recombinant antibody was purified from the cultured solution using KanCap A resin (Kaneca).

The purified antibody was quantified by measuring OD (optical density) at 280 nm, and the results are shown in FIGS. 2a to 2d. As shown in FIGS. 2a to 2d, most of the antibodies produced regardless of the type of heavy and light chains to be combined showed relatively high productivity.

In order to analyze the purity of the purified antibody, a size exclusion HPLC (hereinafter, SE-HPLC) analysis was performed using a Sepax Zenix-C SEC-300 size exclusion column (Sepax technologies) to measure the peak symmetry factor. The obtained results are shown in FIGS. 3a to 3d. When the high-purity antibody is analyzed by SE-HPLC, one symmetric peak is observed, but when heterogeneous substances such as macromolecule/small molecule are included, two or more peaks are observed or the symmetric peak factor is observed to be low. As shown in FIGS. 3a to 3d, in most cases, the anti-ICAM-1 humanized antibody exhibited a relatively high symmetric peak factor.

3-3. Humanized Antibody Selection According to Physicochemical/Biological Properties

3-3-1. High Stability Humanized Antibody Screening

3-3-1-1. Primary Screening of High-Stability Humanized Antibodies

In order to preferentially select antibodies with high stability, humanized antibodies showing resistance to heat denaturation were selected by leaving the antibodies under severe conditions of high temperature and observing changes in their physical properties.

The measurement of heat denaturation was confirmed through a binding experiment using 8-anilino-1-naphthalenesulfonic acid (hereinafter ANS; Sigma). ANS is a compound that can confirm the presence or absence of protein denaturation because it binds to the hydrophobic site exposed during protein denaturation and emits light with a wavelength of 470 nm.

96 kinds of humanized recombinant antibodies prepared in Example 2-1 were constantly diluted to a concentration of 0.2 mg/ml using PBS (phosphate buffered saline), and left at a high temperature (61° C.) for an appropriate time (1 hour). 20 uL of a 0.2 mg/ml ANS solution was added to 200 uL of the antibody sample, mixed, reacted for 15 minutes, and analyzed under 360 nm excitation and 460 nm emission conditions. The 460 nm wavelength emitted by the ANS reaction was measured with a fluorometer (BioTek, SynergyHT), and relative evaluation based on the H1L1 antibody (100%) was shown in FIGS. 4a to 4d. In the case of heavy chains VH7 and VH22, irrespective of the light chain to be combined, 470 nm fluorescence emission by ANS appeared to increase rapidly, and it was confirmed that it was slightly denatured by heat, but other antibodies showed relatively stability against heat.

3-3-1-2. Secondary Screening of Highly Stable Humanized Antibodies

Figure 5:
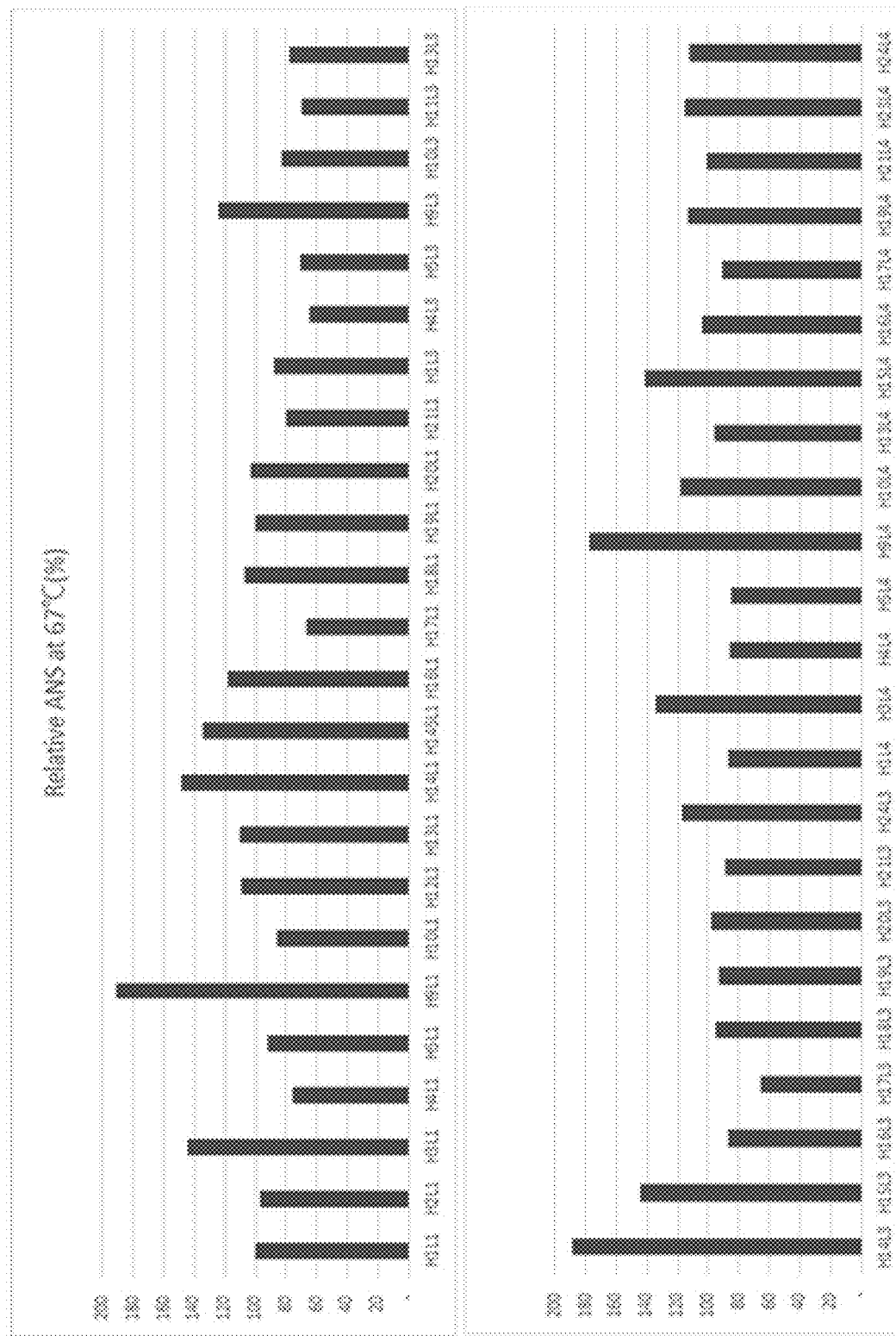
FIG. 5 is a graph showing the results of measuring ANS reactivity after leaving the anti-ICAM-1 antibody obtained according to one example at 67° C. for 1 hour.

A total of 47 kinds of humanized antibodies showing relatively high antibody productivity, relatively high peak symmetry factor, and/or relatively high thermal stability under high temperature (61° C.) conditions in FIGS. 2a-2d, 3a-3d, and 4a-4d, were selected primarily (see FIG. 5).

For more stringent stability evaluation, the 47 kinds of humanized antibodies were constantly diluted to a concentration of 0.2 mg/ml, left at 67° C. for 1 hour, and the ANS reactivity was measured, and the relative reactivity based on the H1L1 antibody was shown in FIG. 5. Compared with the ANS reactivity at 61° C. (4a to 4d), the ANS reactivity at 67° C. tended to be slightly higher, but 6 types of humanized antibodies of the combination of H17L1, H4L3, H5L3, H11L3, H17L3, and H17L4 (See Table 7) showed relatively low ANS reactivity, and were evaluated as antibodies having high resistance to heat denaturation.

TABLE 7

| Antibody name | HC & LC combination |
|---|---|
| H17L1 | VH17 + VL1 |
| H4L3 | VH4 + VL3 |
| H5L3 | VH5 + VL3 |
| H11L3 | VH11 + VL3 |

TABLE 7-continued

| Antibody name | HC & LC combination |
|---|---|
| H17L3 | VH17 + VL3 |
| H17L4 | VH17 + VL4 |

3-3-2. Antigen Binding Assay

As a stability test evaluation, as shown in Table 7, humanized antibodies of 6 leading antibodies were selected, and the binding ability of 5 antibodies excluding H11L3 was compared with the parent antibody (chimeric antibody; see Example 1.3).

The antigen ICAM-1 (ICAM-1; R&D System) was coated on a 96 well plate at 100 ng per well, followed by blocking. The amount of the primary antibody was serially diluted twice from 80 ng/ml and bound for 1 hour at 37° C. and a secondary antibody diluted 1:10000 with goat anti-Human Ig-HRP conjugate (Jackson ImmunoResearch) was combined at 37° C. for 30 minutes. Each step was washed three times and reacted with TMB (3,3',5,5'-Tetramethylbenzidine). After the reaction was stopped by treatment with 1N $H_2SO_4$ solution in the same amount (100 ul) as the TMB solution, the OD value was measured at 450 nm.

Figure 6:
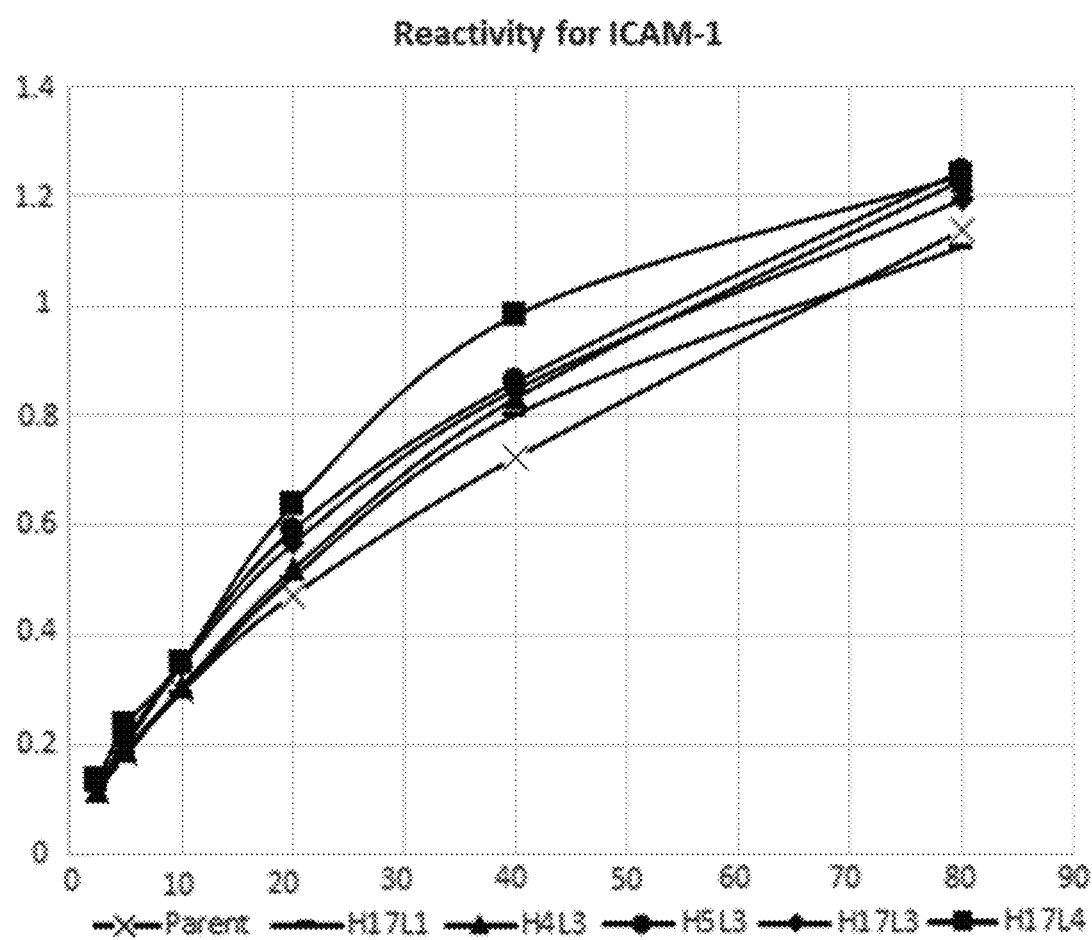
FIG. 6 is a graph comparing the binding power of the anti-ICAM-1 antibody to the ICAM-1 antigen obtained according to one example by ELISA test (y-axis: 450 nm OD value; x-axis: antibody concentration (ng/ml)).

The binding ability of the parent antibody and the five humanized recombinant antibodies obtained as described above to the ICAM-1 antigen is shown in FIG. 6 and Table 8.

TABLE 8

| Antibody concentration (ng/ml) | Chimeric | H17L1 | H4L3 | H5L3 | H17L3 | H17L4 |
|---|---|---|---|---|---|---|
| 80 | 1.138 | 1.108 | 1.229 | 1.246 | 1.197 | 1.238 |
| 40 | 0.724 | 0.802 | 0.832 | 0.862 | 0.848 | 0.983 |
| 20 | 0.473 | 0.506 | 0.520 | 0.592 | 0.567 | 0.637 |
| 10 | 0.298 | 0.297 | 0.305 | 0.35 | 0.344 | 0.349 |
| 5 | 0.182 | 0.186 | 0.189 | 0.208 | 0.201 | 0.236 |
| 2.5 | 0.118 | 0.119 | 0.115 | 0.128 | 0.135 | 0.136 |

All 5 types of the evaluated humanized antibodies generally showed higher reactivity than the chimeric parent antibody, and among them, the antibody of the H17L4 combination showed the highest reactivity.

3-3-3. Melting Temperature Analysis

In particular, the melting temperatures of the humanized antibodies H17L1 and H17L4 exhibiting stable physical properties were compared with the parent antibody (chimeric antibody; see Example 1.3) to evaluate the stability.

Protein thermal shift dye (Lifetechnologies, #4466038) was added to the antibody sample to prepare a reaction sample, and the temperature was continuously raised from 25° C. to 95° C. to induce denaturation of the antibody sample. Antibody denaturation was confirmed by irradiating the reaction solution with a wavelength of 580 nm and measuring the wavelength of 623 nm emitted from the protein thermal shift dye, and the melting temperature was analyzed with ViiA™ 7 software. The obtained results are shown in Table 9 below and in FIGS. 7a (chimeric parent antibody), 7b (H17L1) and 7c (H17L4):

TABLE 9

|  | Melting temperature 1 | Melting temperature 2 |
|---|---|---|
| Chimeric | 67.26° C. | 71.47° C. |
| H17L1 | 67.14° C. | 82.33° C. |
| H17L4 | 66.91° C. | 82.57° C. |

Figure 7A:
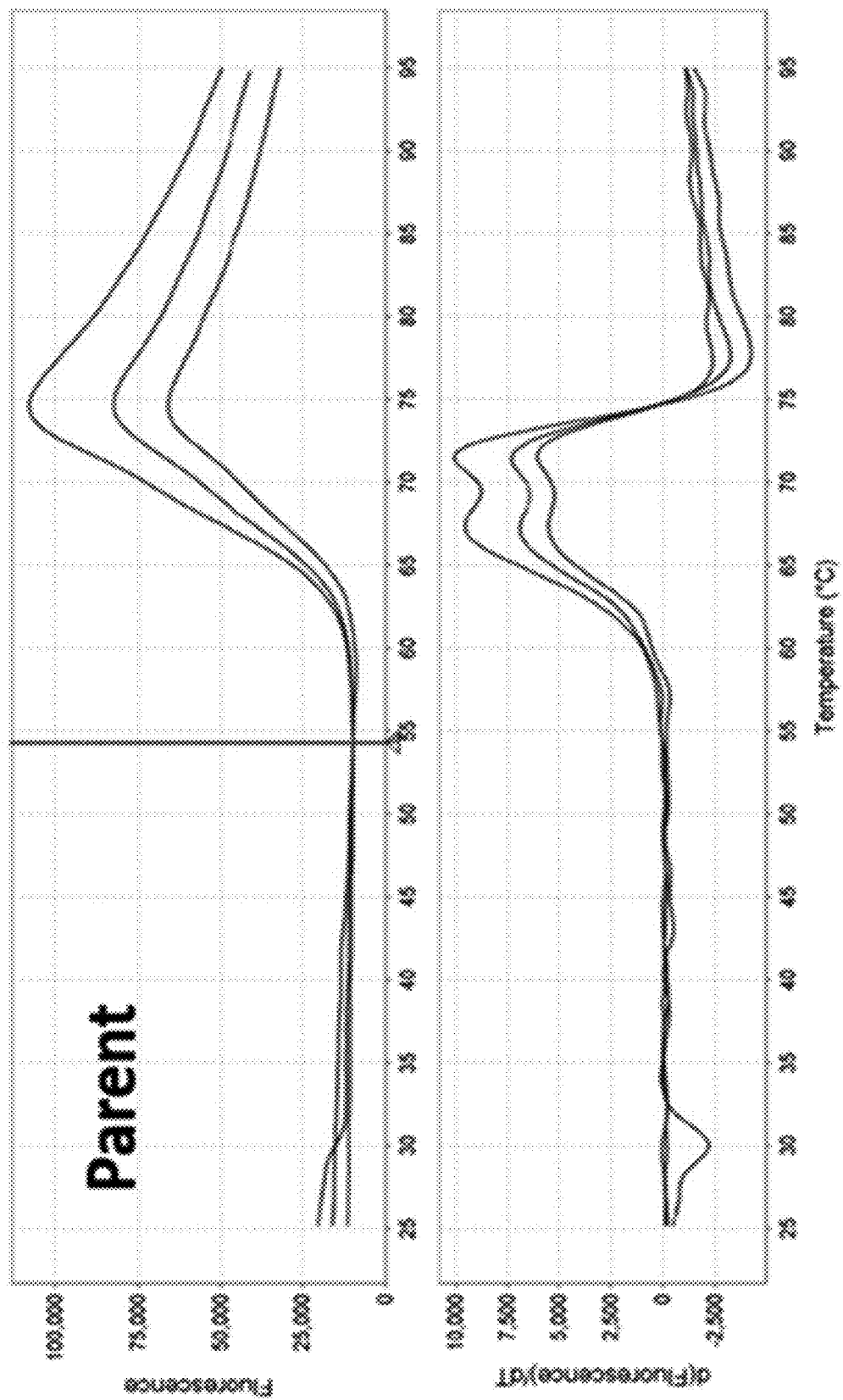
FIG. 7a to 7c are graphs showing the melting point of the anti-ICAM-1 antibody obtained according to one example (7a: chimeric antibody, 7b: H17L1, 7c: H17L4).
Figure 7B:
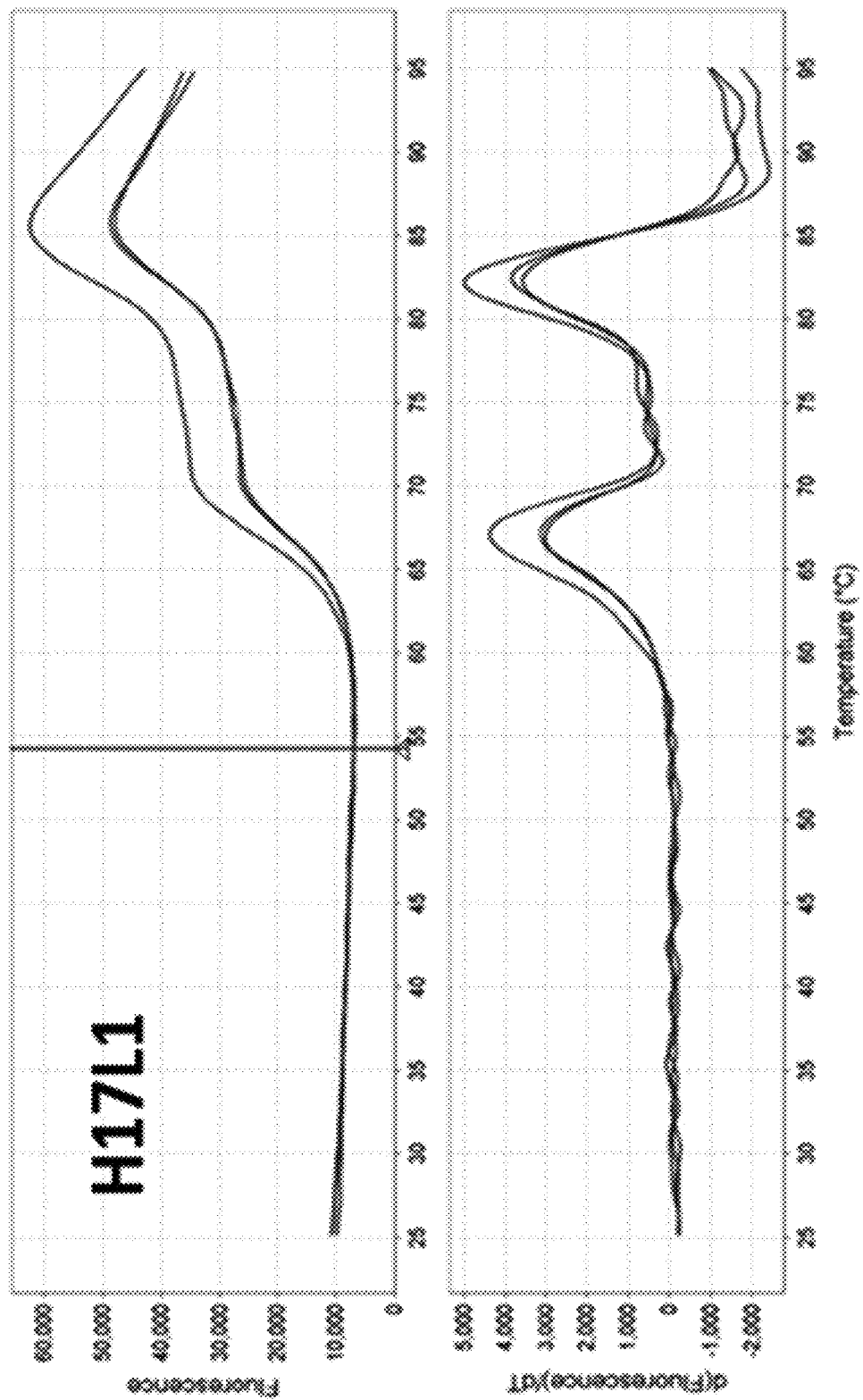
Figure 7C:
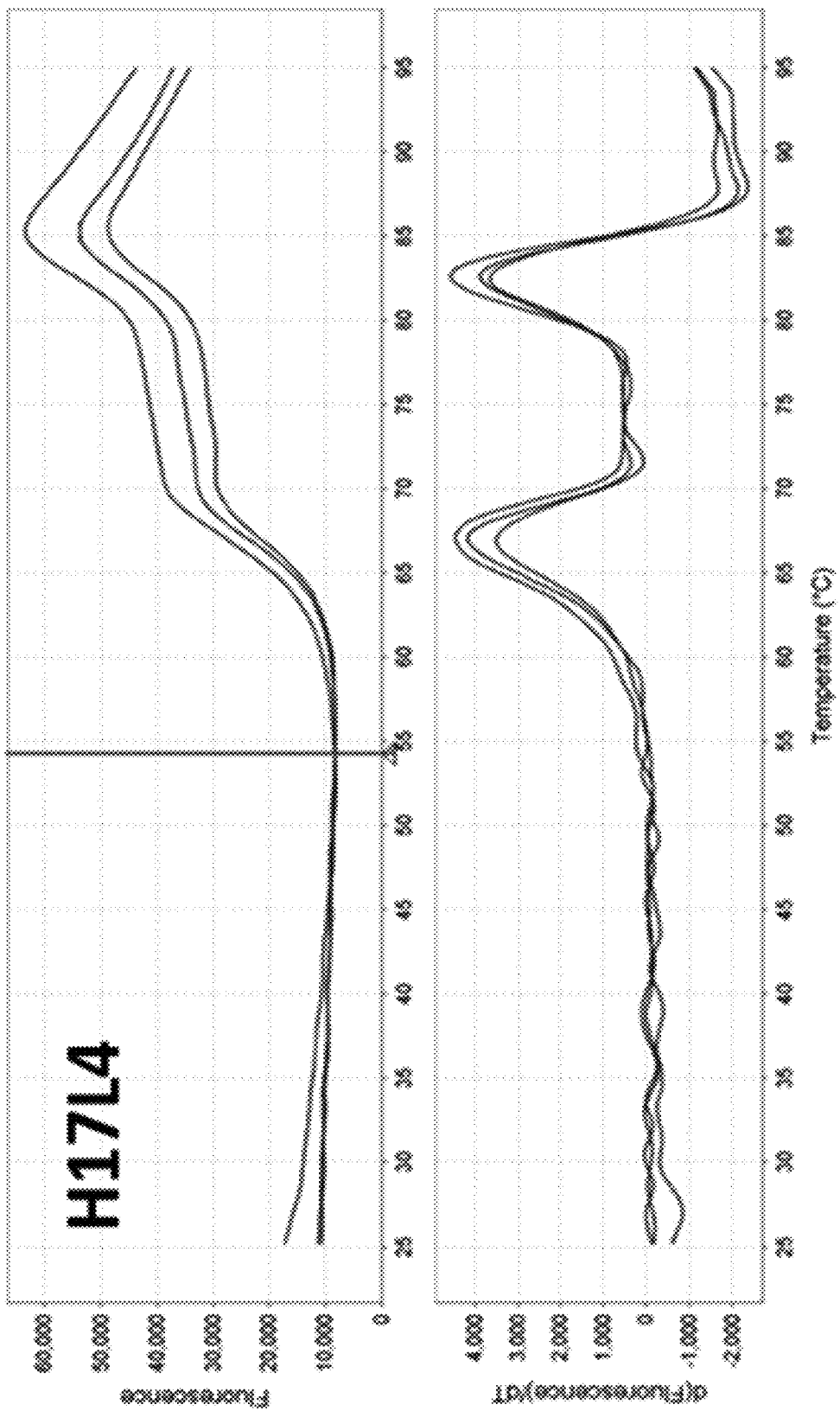

As shown in Table 9 and FIGS. 7a to 7c, two melting temperatures were identified in each antibody sample. Melting temperature 1 was similarly measured at about 67° C. for all three antibodies including the chimeric parental antibody, but melting temperature 2 was 10° C. or more in the two humanized antibodies compared to the chimeric parental antibody. This means that 2 types of humanized antibodies have strong resistance to heat denaturation compared to the chimeric parent antibody.

3-3-4. Affinity Measurement

The Octet system (ForteBio) was used to compare the affinity of the H17L1 and H17L4 humanized antibodies to the antigen with the parent antibody. Each of three antibodies was attached to the amine reactive Bio-sensor AR2G (ForteBio), and 5 different concentrations of ICAM-1 antigen solution were added to induce antigen/antibody reactions to occur. Using the antigen/antibody reaction results, the binding constant (Kon) and the dissociation constant (Koff) were measured, and the affinity (KD) was calculated, and the results are shown in Table 10 and FIG. 8:

TABLE 10

|  | Kon(1/Ms) | Koff(1/s) | Rmax(nm) | KD(M) | Full $X^2$ | Full $R^2$ |
|---|---|---|---|---|---|---|
| Chimeric | $1.65 \times 10^5$ | $1.69 \times 10^{-3}$ | 0.3511 | $1.03 \times 10^{-8}$ | 0.0635 | 0.9869 |
| H17L1 | $2.49 \times 10^5$ | $8.53 \times 10^{-4}$ | 0.4283 | $3.43 \times 10^{-9}$ | 0.0487 | 0.9927 |
| H17L4 | $2.56 \times 10^5$ | $9.29 \times 10^{-4}$ | 0.4282 | $3.62 \times 10^{-9}$ | 0.1555 | 0.9702 |

Figure 8:
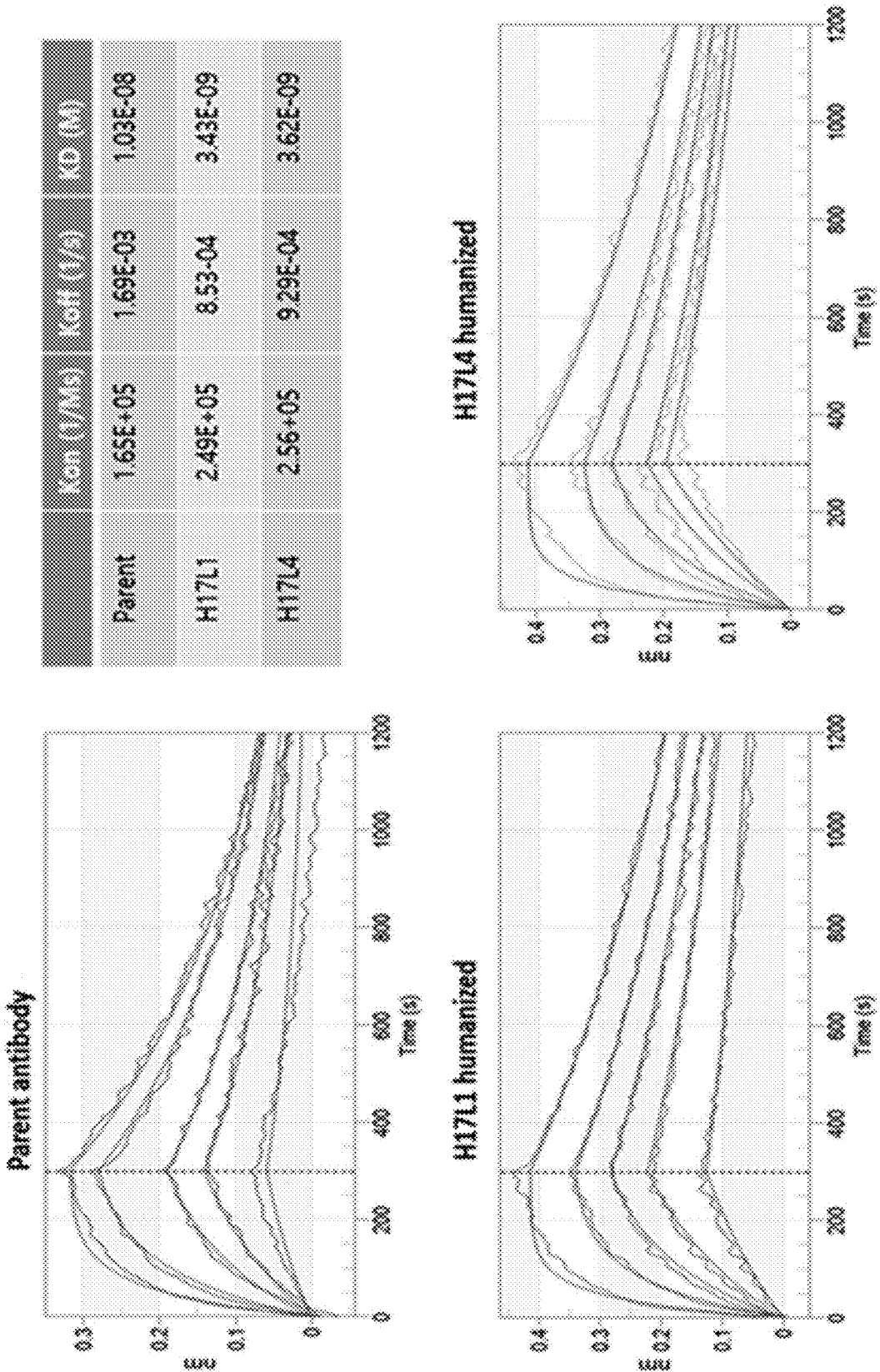
FIG. 8 is a graph showing the affinity (KD) by measuring the binding constant (Kon) and the dissociation constant (Koff) of the anti-ICAM-1 antibody obtained according to one example.

As shown in Table 10 and FIG. 8, the affinity (KD) of the chimeric parent antibody was measured as $1.03 \times 10^{-8}$ M, and the H17L1 and H17L4 humanized antibodies were $3.43 \times 10^{-9}$ and $3.62 \times 10^{-9}$ M, respectively. It was possible to confirm the improved affinity in the humanized antibody.

<Example 4> Immunomodulatory Efficacy Test in Peripheral Blood (In Vitro)

4-1. Isolation of Peripheral Blood Mononuclear Cell and Measurement of IFNg Changes In order to confirm the immunomodulatory efficacy of the antibodies provided herein, peripheral blood mononuclear cells were treated with the DNP007 antibody (H17L4 antibody) prepared in Example 3, and the amount of secretion of IFN-gamma, a representative proinflammatory cytokine, was measured. Blood was collected from normal volunteers, and peripheral blood mononuclear cells were isolated with Ficoll-Paque Plus (GE healthcare, #17144002). The isolated peripheral blood mononuclear cells were suspended in RPMI medium supplemented with 10% FBS, and GM-CSF (Creagene) and IL-4 (Creagene) were added at a concentration of 100 ng/ml, respectively, so that dendritic cells could differentiate from monocytes. DNP007 antibody was added to peripheral blood mononuclear cells at a concentration of 10.0 ug/ml.

In order to confirm the efficacy of DNP007 antibody on the dendritic progenitor cell monocyte, the isolated peripheral blood mononuclear cells were cultured in a culture dish for 2 hours to induce adhesion to the culture dish, and then the adherent cells and suspended cells were divided, respectively, GM-CSF and IL-4 were added at a concentration of 100 ng/ml, respectively, and DNP007 antibody (10.0 ug/ml) was added together.

On the 6th day of culture, peripheral blood mononuclear cells, adherent cells, and suspension cells were washed, respectively, and Lipopolysaccharides (LPS, Sigma-Aldrich, #L2630) were added at 5.0 ug/ml and cultured. The cultured solution was taken the next day and the concentration of IFN-gamma secreted by the Human IFN gamma Uncoated ELISA kit (Invitrogen, #88-7316-77) was measured.

In the sample group treated with the DNP007 antibody under all conditions of peripheral blood mononuclear cells, adherent cells, and suspended cells, the amount of INF-gamma secretion was markedly reduced (Table 11). These results were understood as a phenomenon that appears when the DNP007 antibody suppresses the mechanism of immune cell activation by LPS.

TABLE 11

| | Treatment | IFN-gamma (pg/ml) | Relative change (%) |
|---|---|---|---|
| Whole PBMC | (—) | 559.7 | 100% |
| | DNP007 (10.0 ug/ml) | 166.9 | 29.8% |
| Adherent PBMC | (—) | 612.7 | 100% |
| | DNP007 (10.0 ug/ml) | 425.9 | 69.5% |
| Suspended PBMC | (—) | 513.9 | 100% |
| | DNP007 (10.0 ug/ml) | 130.0 | 25.3% |

4-2. Analysis of the Effect of DNP007 Antibody on Peripheral Blood Mononuclear Cells—Gene Expression Profile Analysis (Transcriptome Analysis by RNA Sequencing)

To determine whether the immune response regulation of DNP007 is only due to dendritic cells or contact with immune cells including dendritic cells and T cells, human peripheral blood mononuclear cells were isolated and divided into 5 kinds of peripheral blood groups, and 100 ng/ml GM-CSF and 100 ng/ml IL-4 were added. And cells were obtained by culturing for 6 days under conditions with or without the addition of 10 ug/ml of DNP007 antibody. For induction into mature dendritic cells, the cells were washed on the 6th day of culture and treated with 5 ug/ml LPS (Sigma-Aldrich) for one day to obtain cells for each group, and total RNA was isolated and gene expression profiles were analyzed.

(1) Whole PBMC: Human peripheral blood mononuclear cells were isolated from healthy volunteer blood by performing concentration gradient centrifugation with Ficoll-Paque (GE Healthcare).
(2) CD14+ monocyte-derived dendritic cells: CD14+ monocytes were isolated from human peripheral blood mononuclear cells separated by concentration gradient centrifugation of healthy volunteer blood with Ficoll-Paque (GE Healthcare), using magnetic separation (using of magnetic beads).
(3) CD14 deplete PBMC: The CD14+ monocytes of (2) were separated by magnetic separation (using magnetic beads) and the remaining peripheral blood population was used.
(4) Attached PBMC: Human peripheral blood mononuclear cells isolated by performing concentration gradient centrifugation with Ficoll-Paque (GE Healthcare) from healthy volunteers are attached to the cells in a 37° C., 5% $CO_2$ incubator for 2 hours in RPMI medium supplemented with 10% FBS, and then the supernatant (including suspension cells) was removed and only adherent cells were separated.
(5) The upper layer of suspension cells removed from the experiment in (4) was used.

Figure 9:
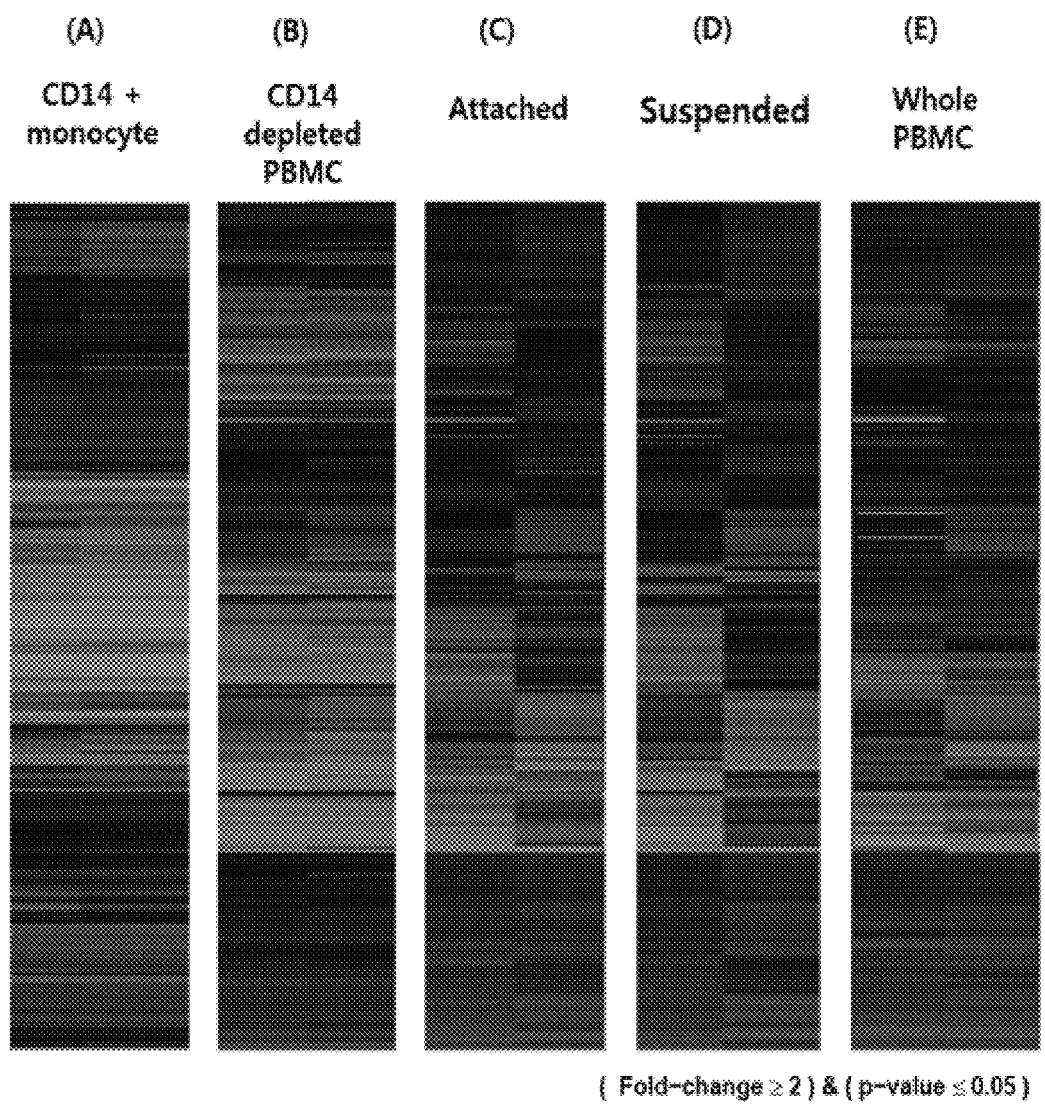
FIG. 9 is a heat map graph showing changes in gene expression profiles by administration of a humanized antibody obtained according to one example under various peripheral blood conditions.

The results are shown in FIG. 9. As shown in FIG. 9, dendritic cells differentiated from CD14+ monocytes alone (A) and peripheral blood populations without CD14+ monocytes (B) showed a gene expression profile similar to that of the control group not treated with DNP007. On the other hand, in the condition (C,D,E) in which several other immune cells are present together, rather than the condition in which CD14+ derived dendritic cells exist alone, when DNP007 was added, the gene expression profile was significantly different from that of the control group not treated with DNP007.

Figure 10:
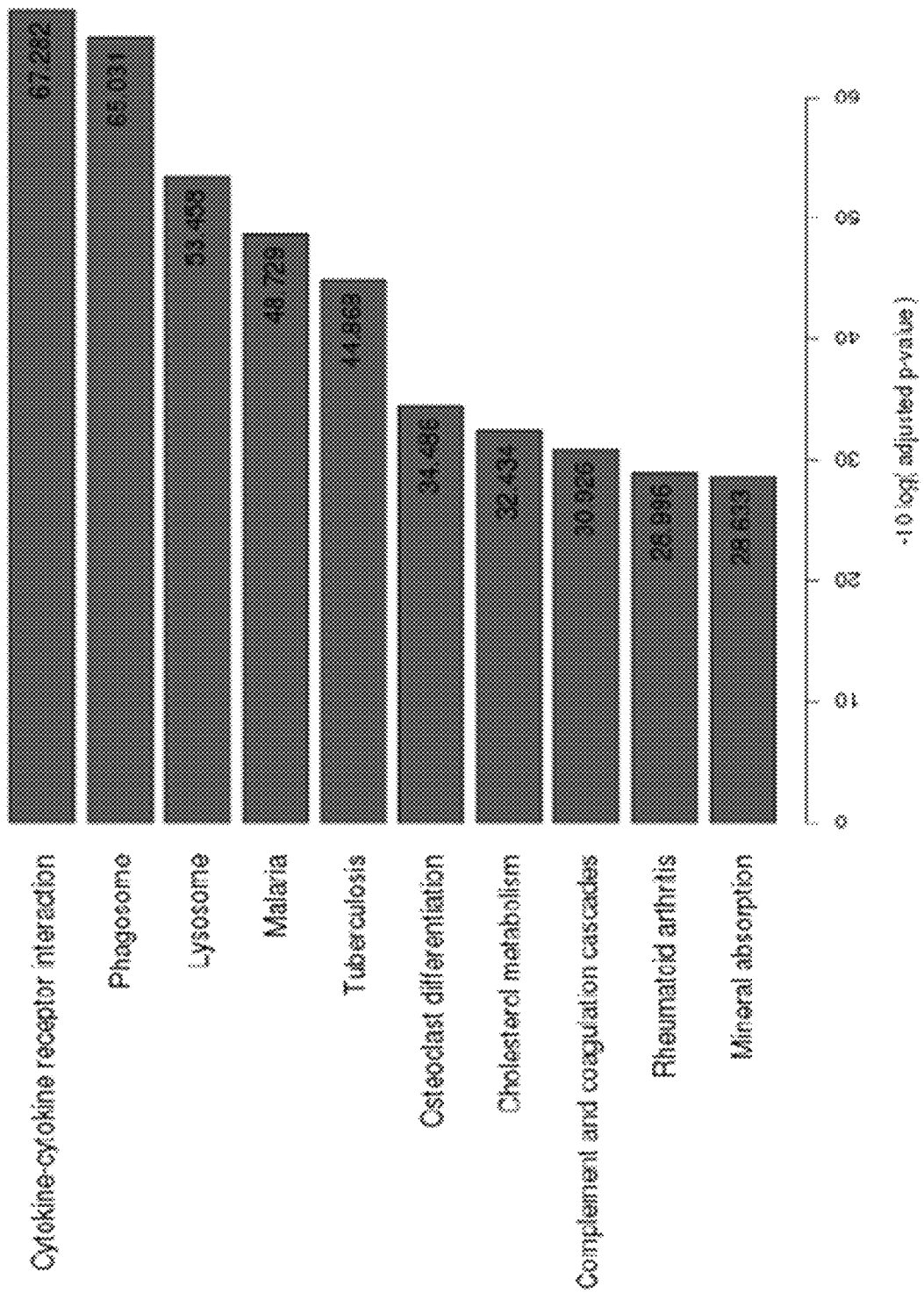
FIG. 10 is a graph showing changes in the gene expression profile obtained by administration of the humanized antibody DNP007 obtained according to one example under various peripheral blood conditions by analyzing the KEGG pathway (−10 log (adjusted p-value)).
Figure 11:
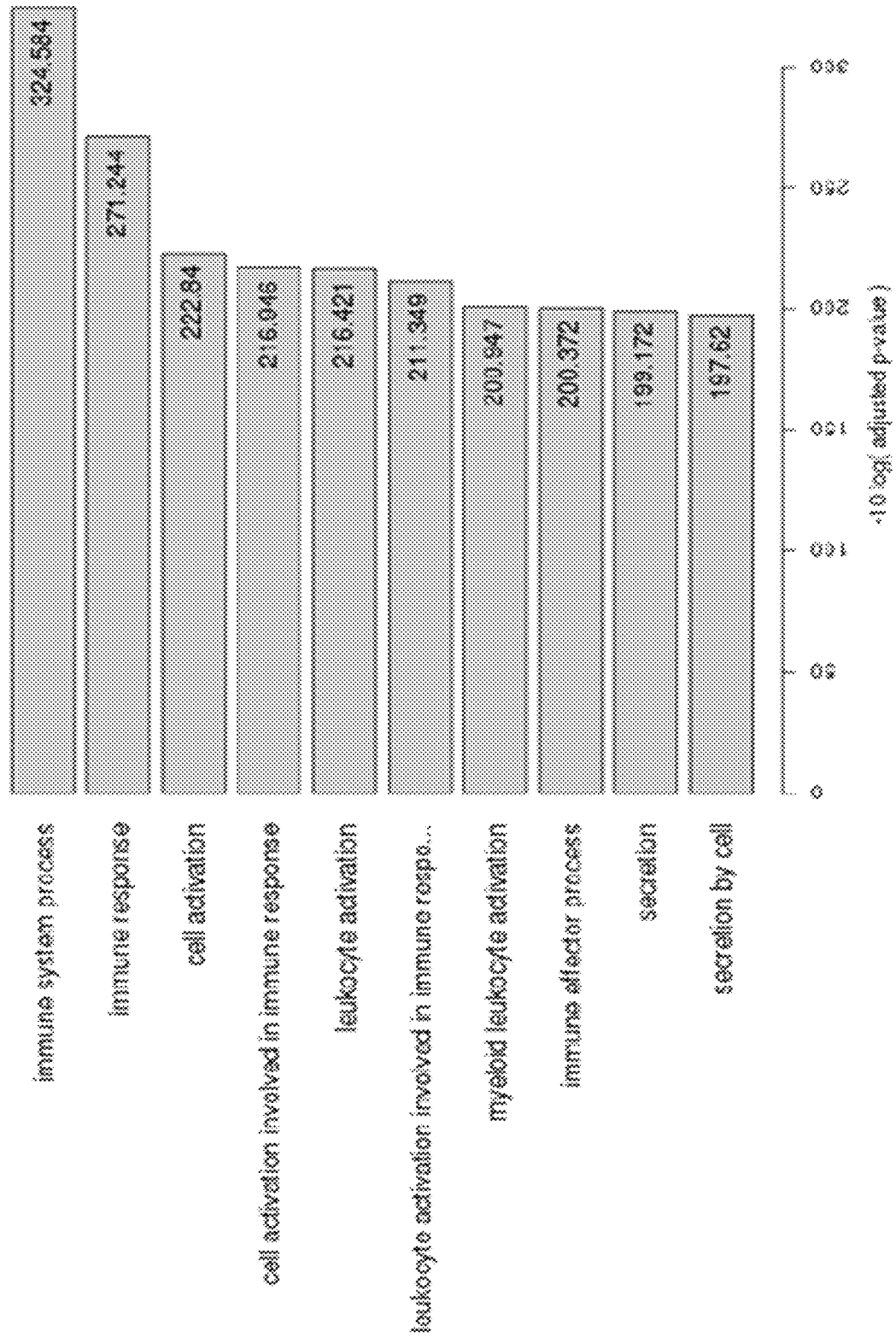
FIG. 11 is a graph showing changes in the gene expression profile obtained by administration of the humanized antibody DNP007 obtained according to one example under various peripheral blood conditions by analyzing the GO Biological process (−10 log (adjusted p-value)).
Figure 12A:
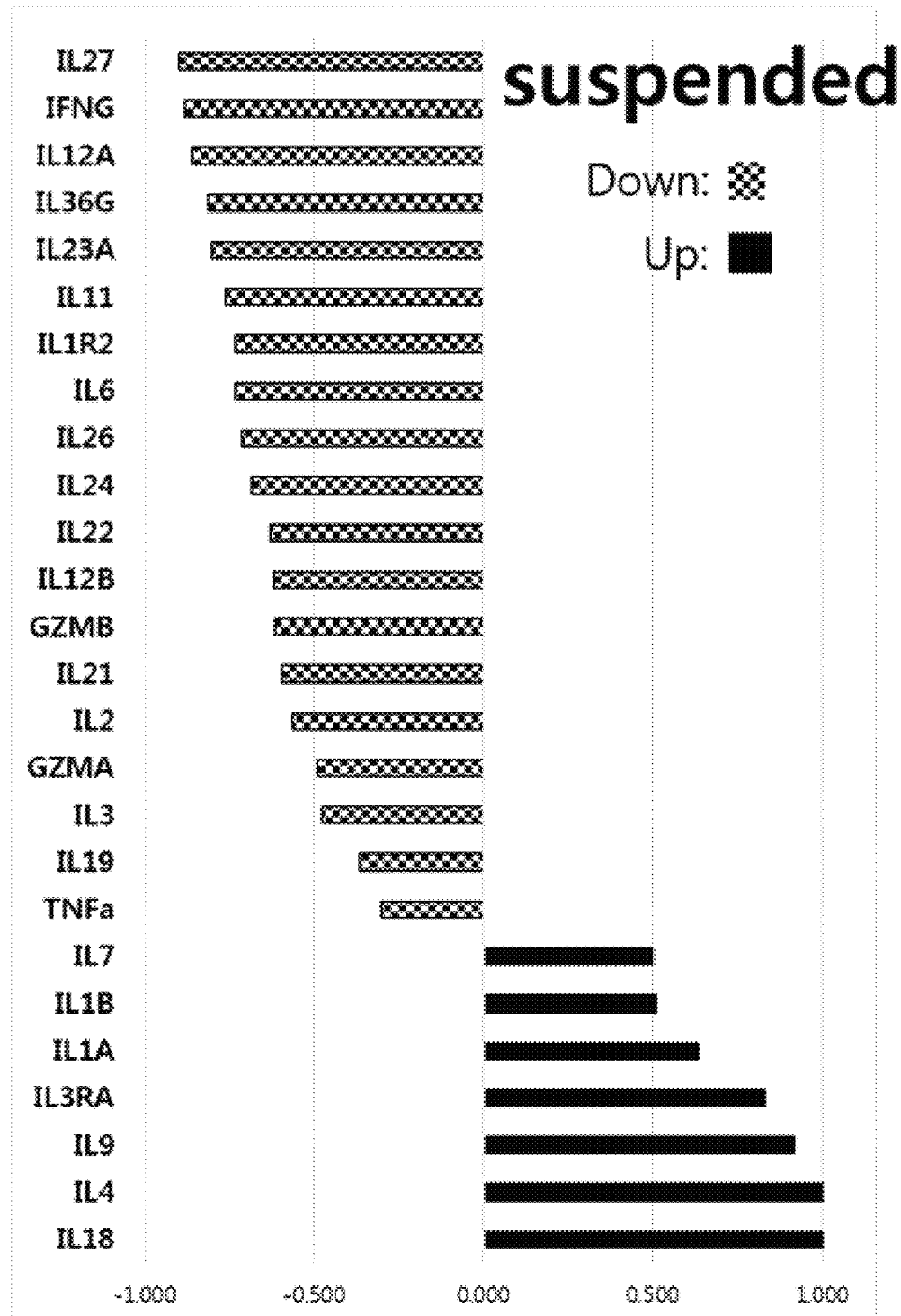
FIGS. 12a and 12b are graphs showing changes in the gene expression profile obtained by administration of the humanized antibody DNP007 obtained according to one example under various peripheral blood conditions by analyzing the increase and decrease of cytokine genes.
Figure 12B:
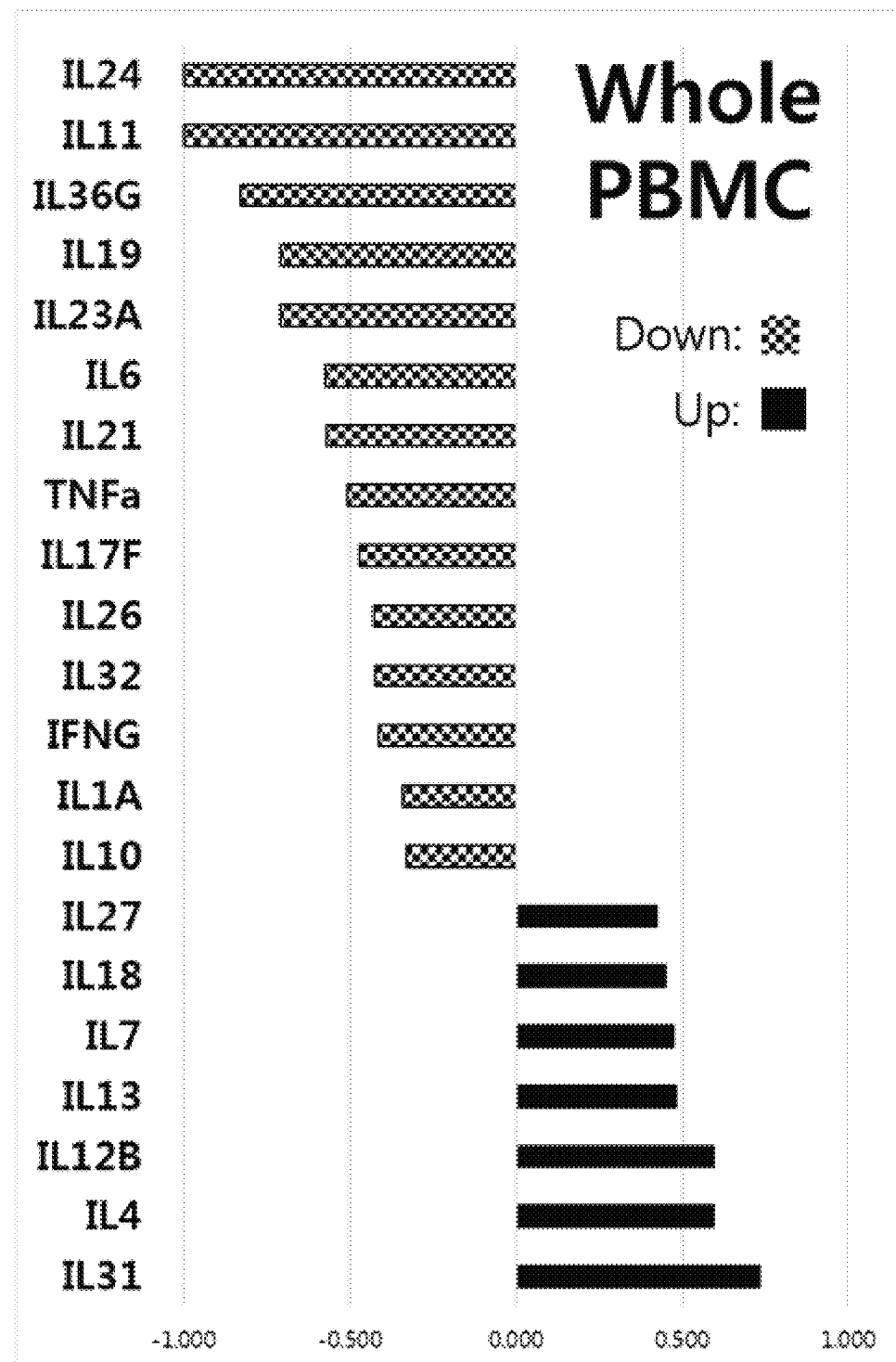

In addition, as a result of analyzing the KEGG pathway & GO Biological process by dividing genes up and down twice or more compared to the control group not treated with DNP007 into gene groups with similar functions in these total gene expression profiles, the gene expression profiles changed by DNP007 were mostly genes involved in regulating immune responses including inflammatory responses (FIGS. 10 and 11). A schematic diagram of a part for cytokines among genes having a clear pattern of change is shown in FIGS. 12a and 12b. As a result of gene expression analysis of the upper layer of suspension cells and whole peripheral blood mononuclear cell (whole PBMC) samples excluding adherent cells in peripheral blood, as shown in FIGS. 12a and 12b, it was found that gene expression of cytokines, which are targets of representative autoimmune diseases such as IL6, IL17, IL23, and IL36, was suppressed by treatment with the DNP007 antibody.

Through these results, the ICAM-1 antibody DNP007 proposed in the present specification does not affect only dendritic cells, but acts on the contact process or cross-reaction between dendritic cells and other immune cells, through this, it can be seen that the expression of various immune response genes is regulated, resulting in an immunosuppressive response.

4-3. Analysis of the Effect of DNP007 Antibody on Peripheral Blood Mononuclear Cells—Cytokine Analysis When preparing the 4-2 experiment set above, in order to confirm whether the gene expression change showed a correlation with the actual protein expression change, in the 4-2 experiment, the supernatant was separated and the actual cytokines were quantitatively analyzed.

IFNgamma, IL1 beta, IL-6, IL-10, IL-12 (p70), IL-17, IL-27 were analyzed using Human Luminex Screening assay (LXSAH, R&D) kit, and TGF-beta was analyzed using a TGF-beta premixed assay kit (TGTBMAG-64K-03; Merck Millipore).

Figure 13:
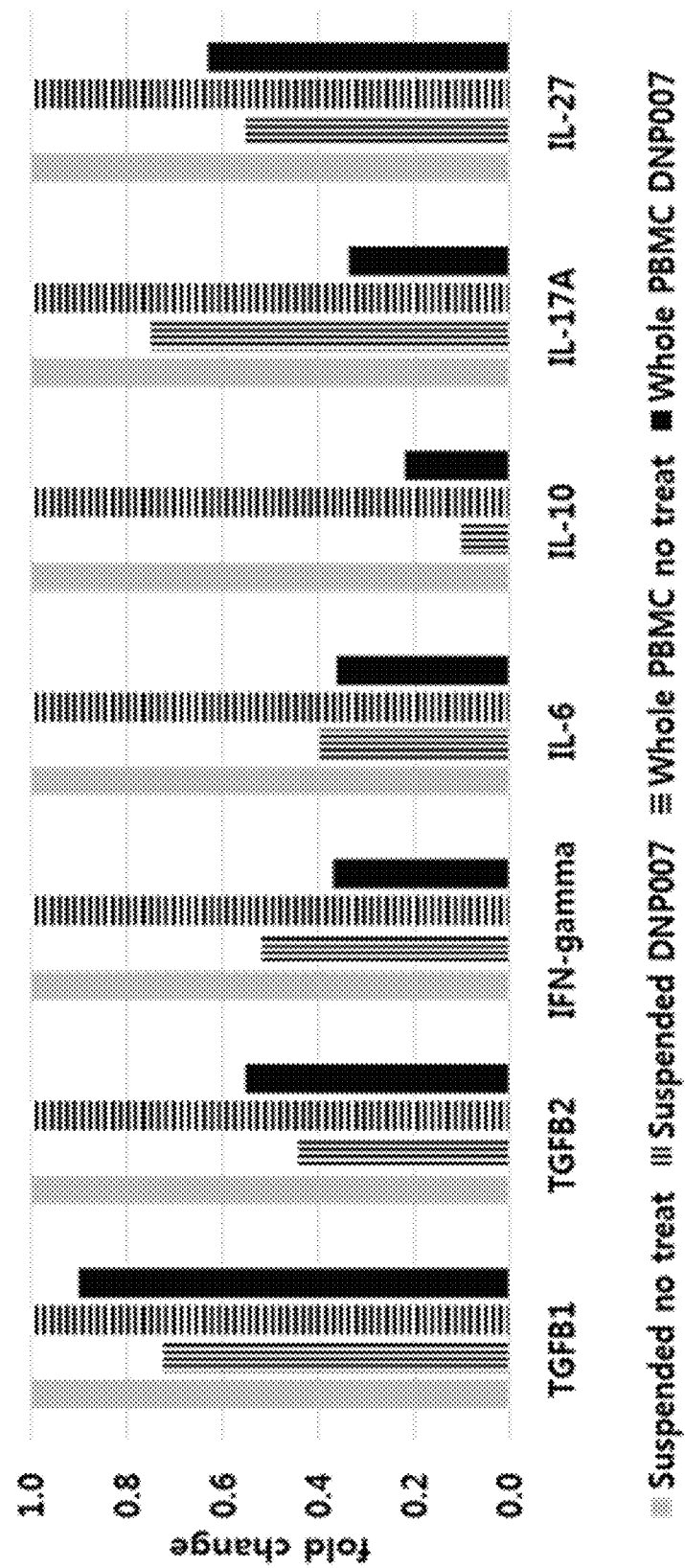
FIG. 13 is a graph showing changes in cytokines obtained by administration of the humanized antibody DNP007 obtained according to one example under various peripheral blood conditions by analyzing the changed increase and decrease in the protein level.

All of the cytokines analyzed as shown in FIG. 13 showed a reduction in actual protein expression of 40 to 80% level by administration of the DNP007 antibody. This is a result consistent with the gene expression profile result of Example 4-2, and it can be said that the immunosuppressive response by the DNP007 antibody was reconfirmed.

In addition, even when the immune activation was induced by LPS treatment under conditions of co-culture with T cells of the same person after separating into peripheral blood of normal humans and differentiating into dendritic cells, the sample administered with the DNP007 antibody showed remarkable inhibition of expression of immune cytokines at the protein level as shown in FIG. 14.

Example 5. Effect Test of Antibody on Dendritic Cells

5-1. Semi-Matured Dendritic Cells Induction Activity Test in Peripheral Blood Mononuclear Cells In this example, the effect of the antibody provided herein on the differentiation and maturation of dendritic cells was confirmed. More specifically, after attaching CD14 microbead (Miltenyi Biotec, 130-050-201) to peripheral blood prepared by collecting blood from normal volunteers, human peripheral blood mononuclear cell was separated using a cell collection device (Miltenyi Biotec. Cat. 000403).

10% FBS containing RPMI culture solution treated with GM-CSF (Creagene) and IL-4 (Creagene) at a concentration of 100 ng/ml, respectively, was added thereto to induce differentiation into immature dendritic cells (immature DCs) for 5 days. On the 5th day of culture, 5 ug/ml of LPS (Lipopolysaccharides, Sigma-Aldrich, #L2630) was added, and the dendritic cells were stimulated for 24 hours to differentiate into mature dendritic cells (mature DC). Antibody DNP007 (H17L4 antibody) and control antibody (hIgG) provided herein were added at a concentration of 5.0 ug/mL on days 0 and 3 of the induction process of dendritic cell differentiation. On the 6th day of differentiation, the expression level of CD80 (Invitrogen, Catalog #11-0809-42), CD86 (BD, Catalog #555657), CD40 (BD, Catalog #555588), CD54 (BD, Catalog #347977) and HLA-DR (BioLegend, Catalog #307616) (Above, in parentheses are antibodies against the factor), a maturation surface factor of dendritic cells, was confirmed and compared using a flow cytometer.

Figure 15:
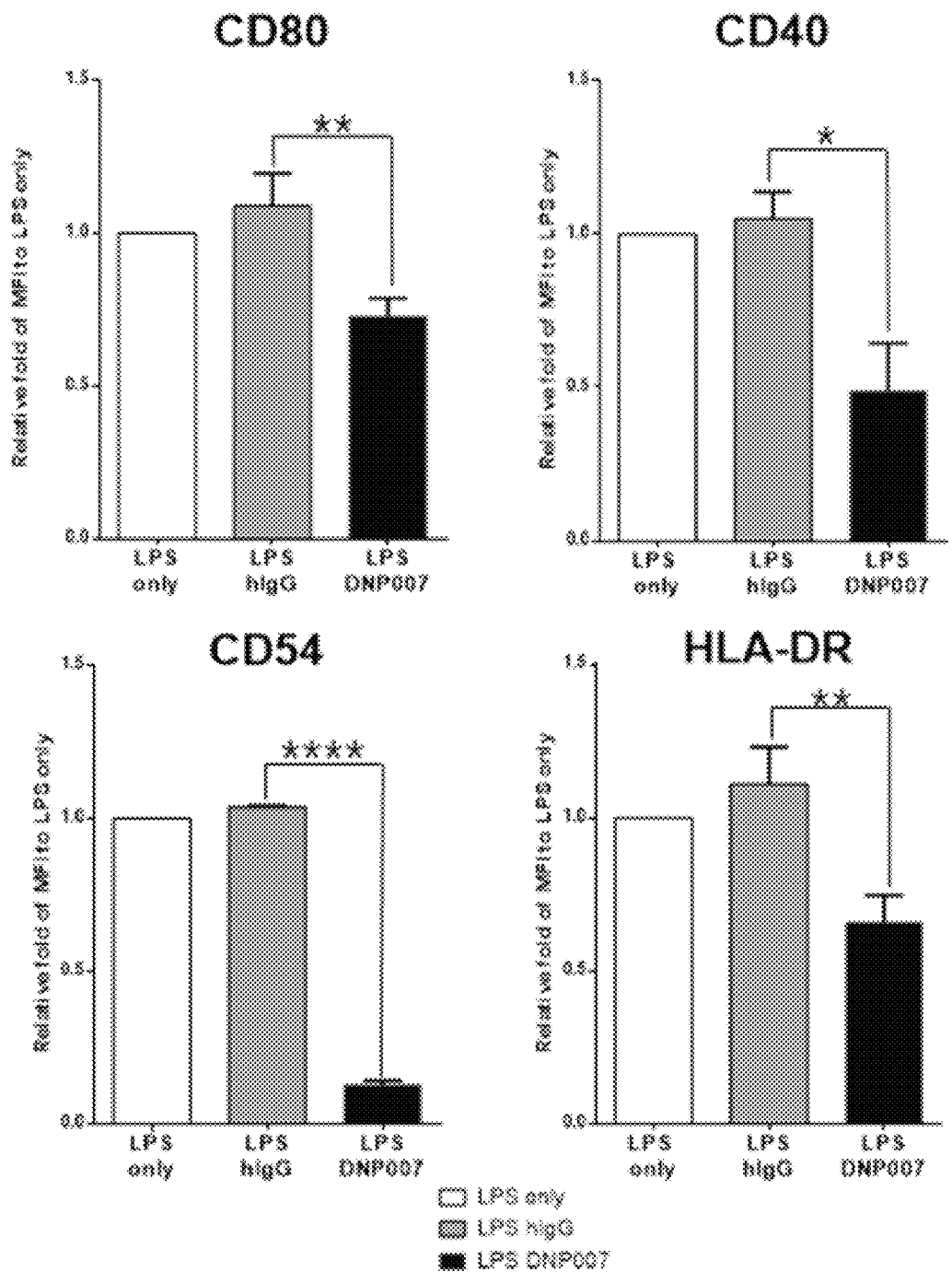
FIG. 15 is a graph showing the expression level of maturation cofactors in dendritic cells treated with the humanized antibody DNP007 obtained according to one example.

The obtained expression level (Mean of Fluorescent Intensity, MFI) of each factor was converted into a relative value for the group treated with only LPS, and is shown in FIG. 15.

As shown in FIG. 15, in the case of dendritic cells treated with a control antibody (hIgG), the expression of cofactors such as CD80, CD54, CD40, and HLA-DR was all increased by LPS stimulation, it was confirmed that the expression of these cofactors was significantly reduced in the group treated with the test antibody DNP007 and LPS. These results show that the antibodies provided herein above limit the maturation of dendritic cells by antigen stimulation and induce an immune suppression environment.

5-2. Proinflammatory Cytokine Secretion Test in Dendritic Cells

In order to confirm whether the antibody provided herein affects the differentiation and maturation stages of dendritic cells, human peripheral blood mononuclear cells isolated from peripheral blood were cultured with GM-CSF and IL-4 for 5 days to differentiate into dendritic cells, and then stimulating factors such as LPS were added and cultured for 24 hours to induce maturation, the amount of proinflammatory cytokine in the culture solution was analyzed to measure the maturity of dendritic cells.

More specifically, after attaching a CD14 microbead (Miltenyi Biotec, 130-050-201) to human peripheral blood, human peripheral blood mononuclear cells were isolated using a cell collection device (Miltenyi Biotec. Cat. 000403). 10% FBS containing RPMI culture solution treated with GM-CSF and IL-4 at a concentration of 100 ng/ml was added thereto to induce differentiation into immature DCs for 5 days. On the 5th day of culture, 5 ug/ml of LPS was added and the dendritic cells were stimulated for 24 hours to induce differentiation into mature dendritic cells (mature DC). Antibody DNP007 (H17L4 antibody) and control antibody (hIgG) provided herein were added at concentrations of 0.1 to 10.0 ug/mL, respectively, on days 0 and 3 of the induction process of dendritic cell differentiation. On day 6 of differentiation, the amount of proinflammatory cytokine (IL-6 and TNF-a) in the cultured solution was analyzed using an ELISA technique.

Figure 16:
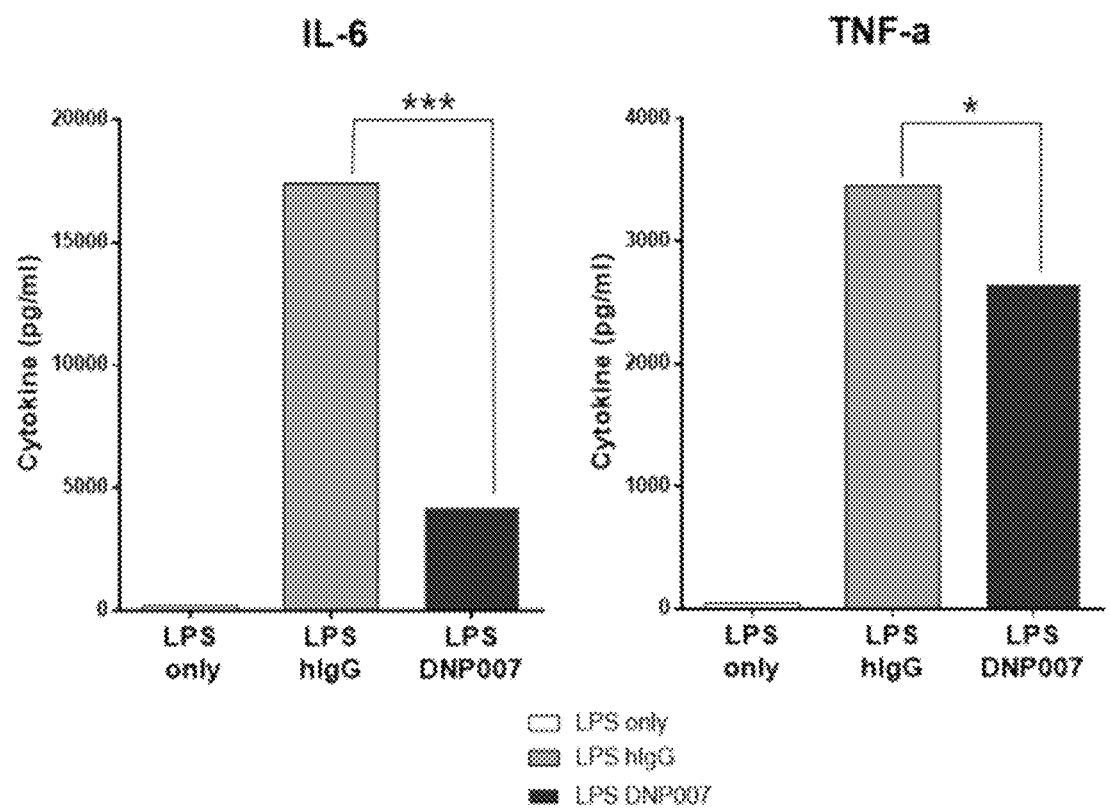
FIG. 16 is a graph showing the degree of secretion of inflammatory cytokines in dendritic cells treated with the humanized antibody DNP007 obtained according to one example.

FIG. 16 shows the results obtained above. As shown in FIG. 16, in mature dendritic cells treated with the control antibody, the secretion of IL-6 and TNF-α, which are representative proinflammatory cytokines, is significantly increased due to LPS stimulation, whereas in dendritic cells treated with the test antibody DNP007 the ability to secrete proinflammatory cytokines was significantly reduced. The maturation of dendritic cells refers to the process by which dendritic cells acquire the ability as antigen-presenting cells, and mature dendritic cells function to induce the activity of antigen-specific T cells. Due to the treatment of the antibodies provided herein, the secretion of the proinflammatory cytokines IL-6 and TNF-α, which is an important measure of dendritic cell maturity, was significantly inhibited, and through this, it was confirmed that the antibody provided herein has a function of inhibiting the maturation of dendritic cells.

5-3. Dendritic Cell Apoptosis Test

In order to determine whether the antibody provided herein affects apoptosis in the differentiation step of dendritic cells, the degree of death of dendritic cells differentiated and matured for 6 days according to the antibody treatment was measured. The degree of apoptosis was confirmed through flow cytometry after 7AAD staining.

More specifically, after attaching a CD14 microbead (Miltenyi Biotec, 130-050-201) to human peripheral blood, human peripheral blood mononuclear cells were isolated using a cell collection device (Miltenyi Biotec. Cat. 000403). 10% FBS containing RPMI culture solution treated with GM-CSF and IL-4 at a concentration of 100 ng/ml, respectively, was added to induce differentiation into immature DCs for 5 days. On the 5th day of culture, 5 ug/ml of LPS was added and the dendritic cells were stimulated for 24 hours to differentiate mature dendritic cells. Antibody DNP007 (H17L4 antibody) provided herein and control antibody (hIgG) were added twice at a concentration of 5.0 ug/mL on days 0 and 3 of the induction process of dendritic cell differentiation. On the 6th day after induction of differentiation, mature dendritic cells (mature DCs) were stained with 7AAD (7-Amino-Actinomycin D, BD, 51-68981E 5 ul/test) and analyzed using a flow cytometer.

Figure 17:
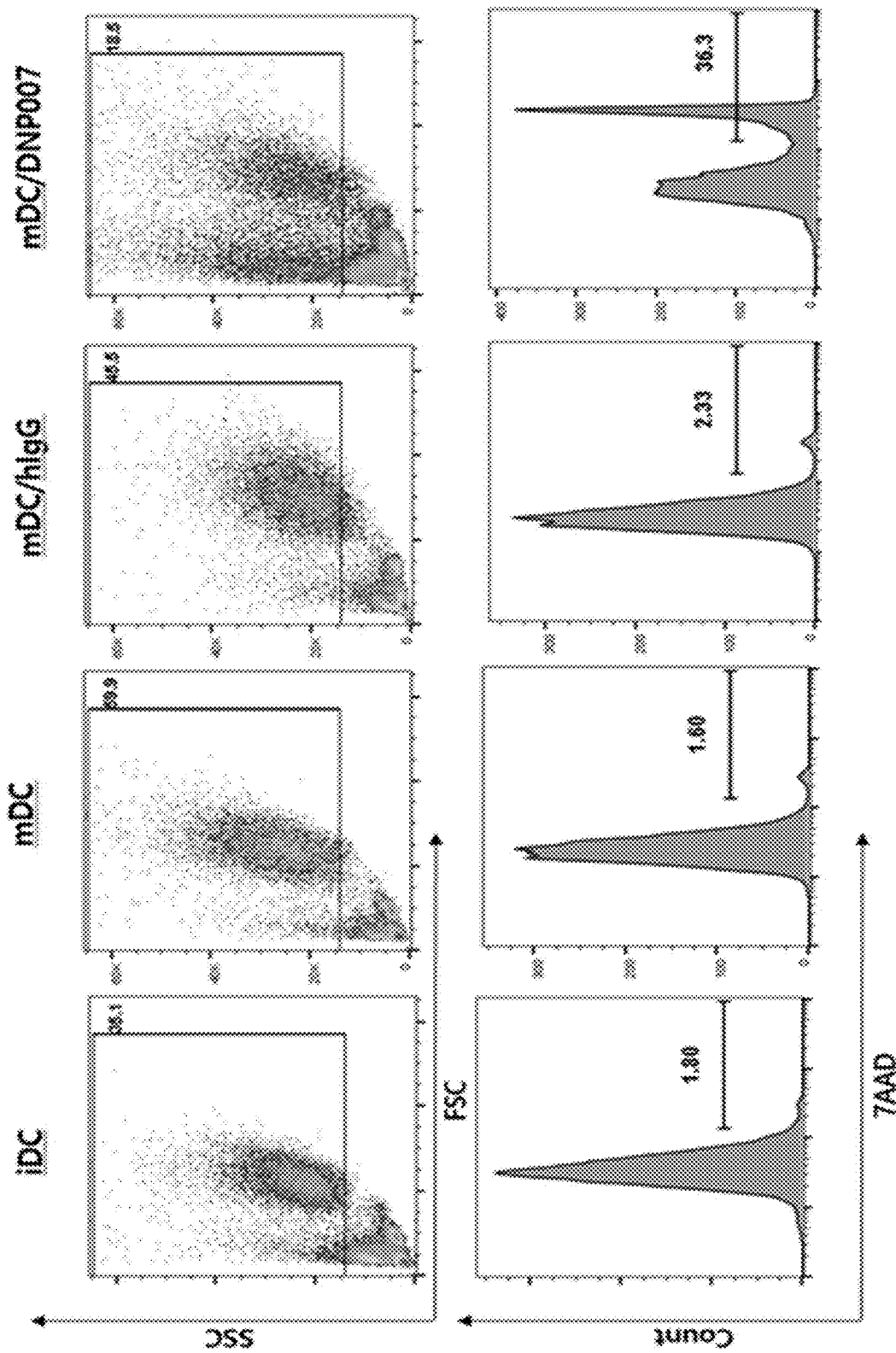
FIG. 17 is a graph showing the degree of apoptosis of dendritic cells treated with the humanized antibody DNP007 obtained according to one example.

The results obtained above are shown in FIG. 17. As shown in FIG. 17, as a result of confirming the degree of apoptosis of dendritic cells that have undergone differentiation and maturation, the control antibody-treated group showed apoptosis of 2.33%, whereas the apoptosis rate of dendritic cells treated with the test antibody DNP007 was 36.3%, it showed a higher apoptosis effect than the control group.

The cytotoxic effect of dendritic cells by the test antibody can be evaluated as due to apoptosis.

5-4. Induction Test of Immune Tolerogenic Dendritic Cells (Tolerogenic DC)

In order to confirm whether the antibody provided herein induces tolerogenic dendritic cells, expression of tolerogenic dendritic cell markers was confirmed by flow cytometry in semi-mature dendritic cells that had undergone differentiation and maturation for 6 days.

More specifically, antibody DNP007 (H17L4 antibody) provided herein and control antibody (hIgG) were added to semi-mature dendritic cells that have undergone differentiation and maturation from human peripheral blood mononuclear cells for 6 days in the same manner as in Examples 5-2 or 5-3 twice at a concentration of 5.0 ug/mL on days 0 and 3 of the induction process of dendritic cell differentiation, and the expression of tolerogenic dendritic cell markers was confirmed by flow cytometry on the 6th day after the differentiation induction.

Cell surface expression factors PDL1 (Invitrogen, Catalog #17-5983-42), PDL2 (Miltenyi biotec, Catalog #130-098-528), and Adenosin Receptor A2b (Novus, Catalog #NBP2-41312PE) (Above, parentheses are antibodies against the factor) was stained by treating the antibody at an appropriate concentration and reacting for 20 minutes in refrigerator. 2 ml of flow cytometry buffer (0.5% BSA, 0.01% NaN3 in 1×PBS) was added, centrifuged at 2200 rpm for 3 minutes, and the supernatant was removed, washed and analyzed.

Cell fluid substances, IDO (Indoleamine 2,3-Dioxygenase; Invitrogen, Catalog #12-9477-42), TGF-β (R&D systems, Catalog #IC240P), IL-10 (Miltenyi biotec, Catalog #130-112-729) (Above, parentheses are antibodies against the factor) were stained according to the intracellular antigen staining method kit manufacturer's manual. 100 ul of IC Fixation buffer (Invitrogen, Catalog #00-8222-49) was added to the cell pellet, the light was blocked at room temperature, and reacted for 30 minutes to fix the cells. 2 mL of 1× Permeabilization buffer (Invitrogen, Catalog #00-8333-56) was added, centrifuged at 600 g for 5 minutes, and the supernatant was removed. An appropriate concentration of each antibody was added to 100 ul of 1× Permeabilization Buffer, treated on the remaining cell pellet, and allowed to react for 30 minutes after blocking light at room temperature. 1× Permeabilization buffer 2 mL was added, centrifuged at 600 g for 5 minutes, washed, and flow cytometry buffer 2 mL was added each, followed by centrifugation to perform additional washing. Cells were fixed by adding 1% paraformaldehyde, and the expression levels of each antigen were analyzed using a flow cytometer.

Figure 18A:
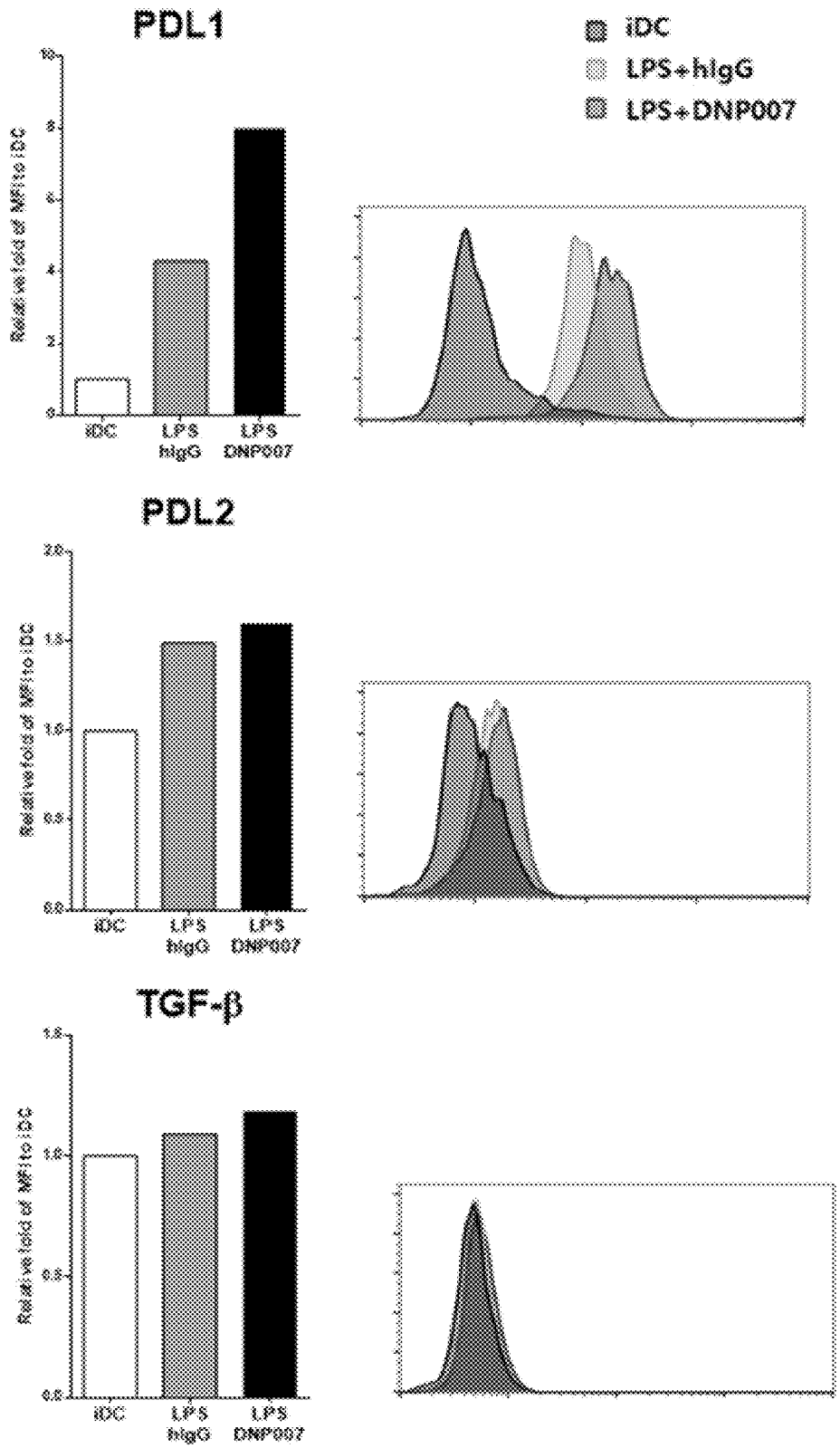
FIGS. 18a and 18b are graphs showing the expression levels of dendritic cell surface factors treated with the humanized antibody DNP007 obtained according to one example, and show whether or not tolerogenic dendritic cells are induced.
Figure 18B:
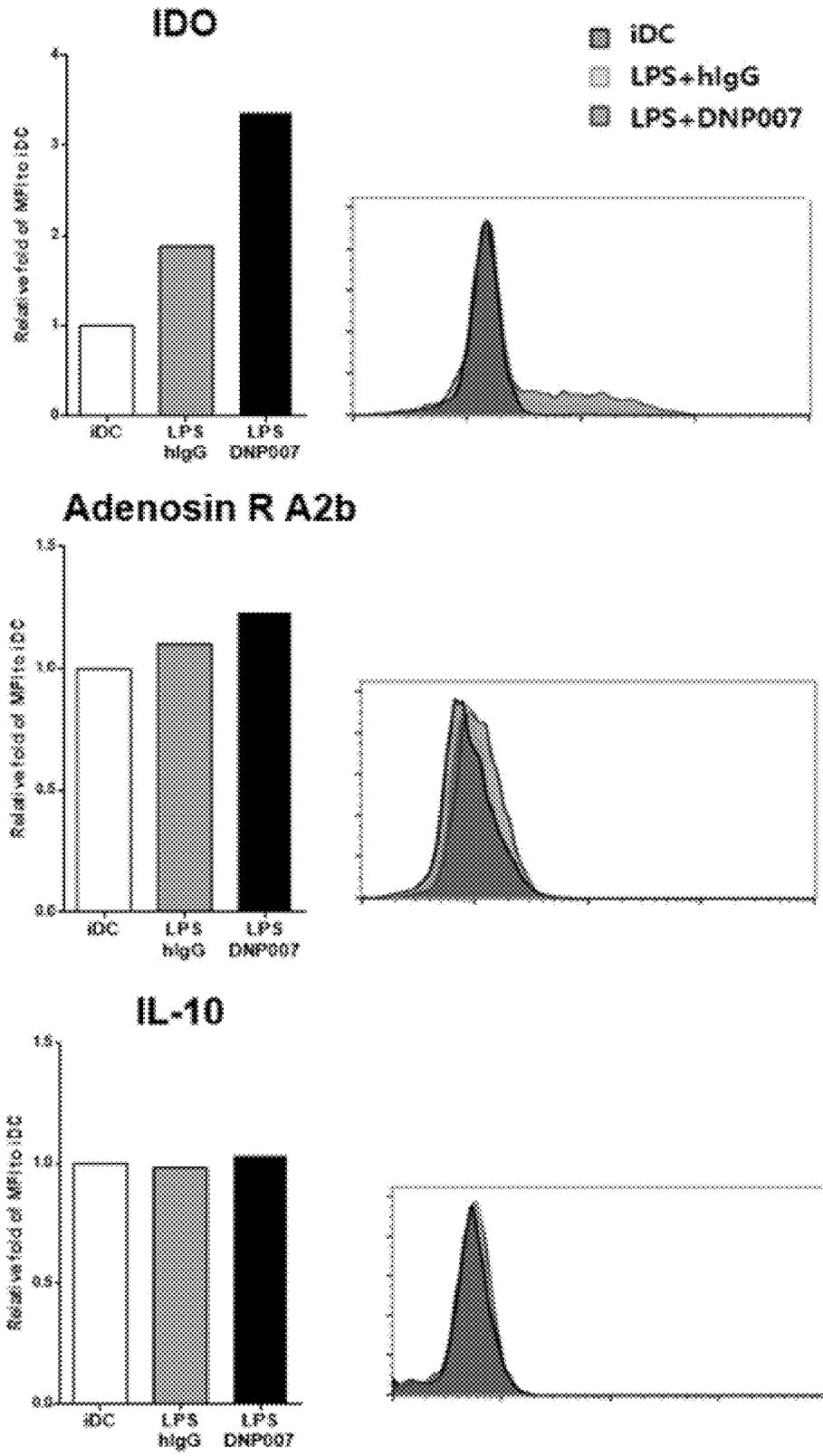

The obtained results are shown in FIGS. 18a and 18b. As shown in FIGS. 18a and 18b, the dendritic cells treated with the test antibody DNP007 showed a significant increase in the expression of IDO, a representative factor of immune tolerance, compared to the control antibody-treated dendritic cells (control), and increase in the expression levels of PDL1, PDL2 and adenosine R A2b, known as other immunosuppressive factors compared to the control group too.

As such, it was confirmed that the expression of some factors related to IDO and immune tolerance was increased through analysis of the dendritic cells treated with the antibodies provided herein. In particular, IDO expressed on dendritic cells is known to inhibit the proliferation of T cells and play an important role in immune tolerance. Thus, an increase in IDO expression by the antibodies provided herein suggests a high possibility of inducing immune tolerance.

5-5. IDO Expression Test in Dendritic Cells

In order to determine whether the inhibition of dendritic cell maturation by the antibodies provided herein is by which of the two known maturation pathways, LPS and CD40L were used to induce maturation of dendritic cells. Expression of IDO, a tolerogenic dendritic cell marker, was confirmed by flow cytometry in semi-mature dendritic cells that had undergone differentiation and maturation for 6 days.

More specifically, stimulation by LPS known as the Canonical pathway was tested under the same conditions as in Examples 5-2 or 5-3 by preparing semi-mature dendritic cells that had undergone differentiation and maturation for 6 days.

In the stimulation test by CD40L, known as the non-canonical pathway, immature dendritic cells differentiated for 5 days by adding 10% FBS containing RPMI culture solution treated with GM-CSF and IL-4 at a concentration of 100 ng/ml, respectively, were used. On the 5th day of culture, 1 ug/ml of CD40L (Enzo, ALX-522-110) was added to 10% FBS containing RPMI treated with GM-CSF and IL-4 at a concentration of 100 ng/ml and stimulated for 48 hours, to induce mature dendritic cells (mature DCs). Antibody DNP007 (H17L4 antibody) provided herein and control antibody (hIgG) were treated twice at a concentration of 5.0 ug/mL on days 0 and 3 during the induction process of dendritic cell differentiation, and CD40L was treated in an amount of 5.0 ug/mL on day 5.

On the 7th day of induction of differentiation, mature dendritic cells (Mature DC) were stained with the above-mentioned staining intracellular antigens and analyzed using a flow cytometer.

The obtained results are shown in FIGS. 19a (Canonical pathway) and 19b (Non-canonical pathway). As shown in FIGS. 19a and 19b, test antibody DNP007 induced a decrease in the expression of IDO in cells during the process of maturation of dendritic cells by CD40L, whereas the maturation of dendritic cells by LPS showed a large difference in IDO expression between individuals. As the maturation pathway of dendritic cells, there are canonical pathways induced by LPS and TNF-α stimulation and non-canonical pathways induced by CD40L. The above results show that the antibodies provided herein affect both dendritic cell maturation pathways, specifically limiting maturation by CD40L and inducing differentiation into tolerogenic dendritic cells.

5-6. T Cell Immune Suppression Test by Water-Soluble Substances

To confirm whether the factor affecting the T cells of dendritic cells whose maturation is inhibited by the treatment of the antibodies provided herein is due to intercellular conjugation or mediators secreted from cells, dendritic cells and T cells were cultured in separate conditions, and the inhibition ability of T cells activity was confirmed.

More specifically, human T cells isolated using a cell collection device after attaching CD3 microbeads (Miltenyi, 130-050-201) to human peripheral blood, and mature dendritic cells (Mature DC) obtained under the same conditions as in Examples 5-1 to 5-5, were cultured in separate conditions to confirm the inhibition ability of T cells activity. In the lower chamber of the plate made to pass through the culture medium, 1 ug/ml of anti-CD3 antibody (BD, 557052) and 1 ug/ml of anti-CD28 antibody (BD, 555725) were coated, and autologous T cells isolated from peripheral blood were put. At this time, autologous T cells were subjected to CFSE labeling as a condition to confirm proliferation. Dendritic cells differentiated by treatment with antibody DNP007 (H17L4 antibody) provided herein were placed in the upper chamber. And the two cells were cultured for 4 days while sharing the culture medium in each chamber. The number of dendritic cells and autologous T cells was treated at a ratio of 1:10.

Figure 20:
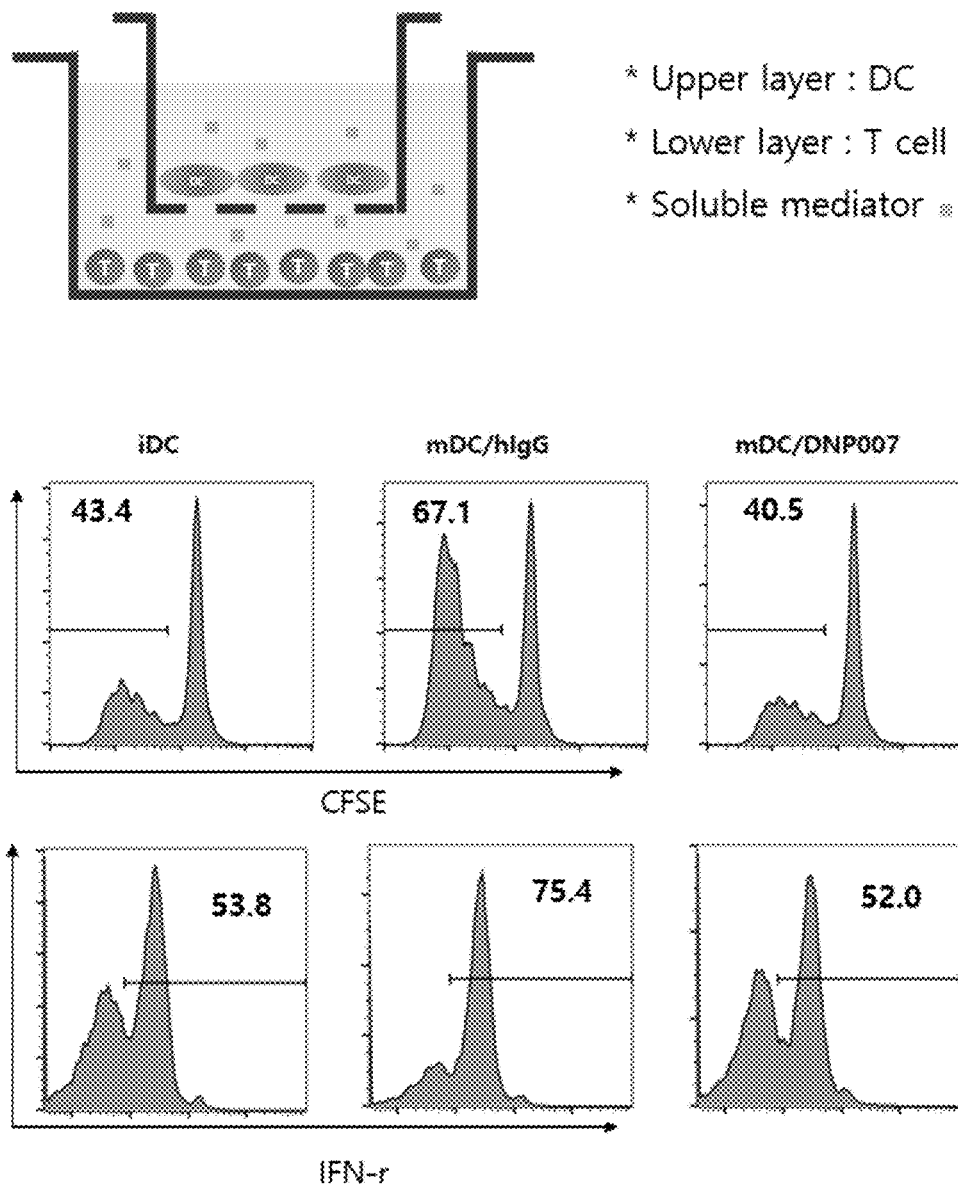
FIG. 20 is a graph showing the level of production of interferon gamma (IFN-r), an inflammatory cytokine and degree of proliferation of T cells cultured with dendritic cells treated with humanized antibody DNP007 obtained according to one example.

The obtained results are shown in FIG. 20. As shown in FIG. 20, in the absence of direct contact between the two cells, the proliferation of T cells was inhibited by the test antibody-treated dendritic cells, and the production of interferon gamma (IFN-r), a proinflammatory cytokine, was reduced. The above results show that the antibody-treated dendritic cells provided herein can inhibit the activity and proliferation of T cells through material exchange with T cells, and indicate that the substance secreted from dendritic cells acts as a mediator to inhibit the activity of T cells, and induces immune tolerance.

5-7. T Cell Immune Suppression Test by Antibody-Treated Dendritic Cells

In order to evaluate the ability to inhibit T cell activity of dendritic cells whose maturation was inhibited by treatment with the antibodies provided herein, the activity and proliferation of T cells were confirmed under conditions in which dendritic cells and T cells were cultured together. First, the maturation of dendritic cells was induced using LPS, TNF-a, and CD40L, which are stimulators of two known maturation pathways, and the proliferation of T cells and the expression level of intracellular proinflammatory cytokines were measured. More specifically, the maturation of dendritic cells was induced using two known maturation pathways (Canonical pathway: LPS, and TNF-alpha/Non-canonical pathway: CD40L). Stimulation with LPS and CD40L was carried out in the same manner as in Example 5-5. And stimulation with TNF-alpha was performed by treating 10% FBS containing RPMI treated with GM-CSF and IL-4 at a concentration of 100 ng/ml, respectively, with 13 ng/ml of TNF-a, 10 ng/ml of IL-1β, and 350 ng/ml of PGE2 on day 5 in the state of being induced to immature dendritic cells and giving stimulation for 48 hours to differentiate into mature DCs. Antibody DNP007 (H17L4 antibody) provided herein and control antibody (hIgG) were treated twice at a concentration of 5.0 ug/ml on days 0 and 3 during the induction process of dendritic cell differentiation.

In order to induce T cell activity, autologous T cells and mature dendritic cells differentiated in the same manner as above were added to a plate coated with 1 ug/ml of anti-CD3 antibody at a ratio of 1:10. After 3 days, the expression level of intracellular inflammatory cytokines and the proliferation of T cells were measured. At this time, similarly, CFSE labeling was performed to confirm the proliferation of T cells.

Figure 21:
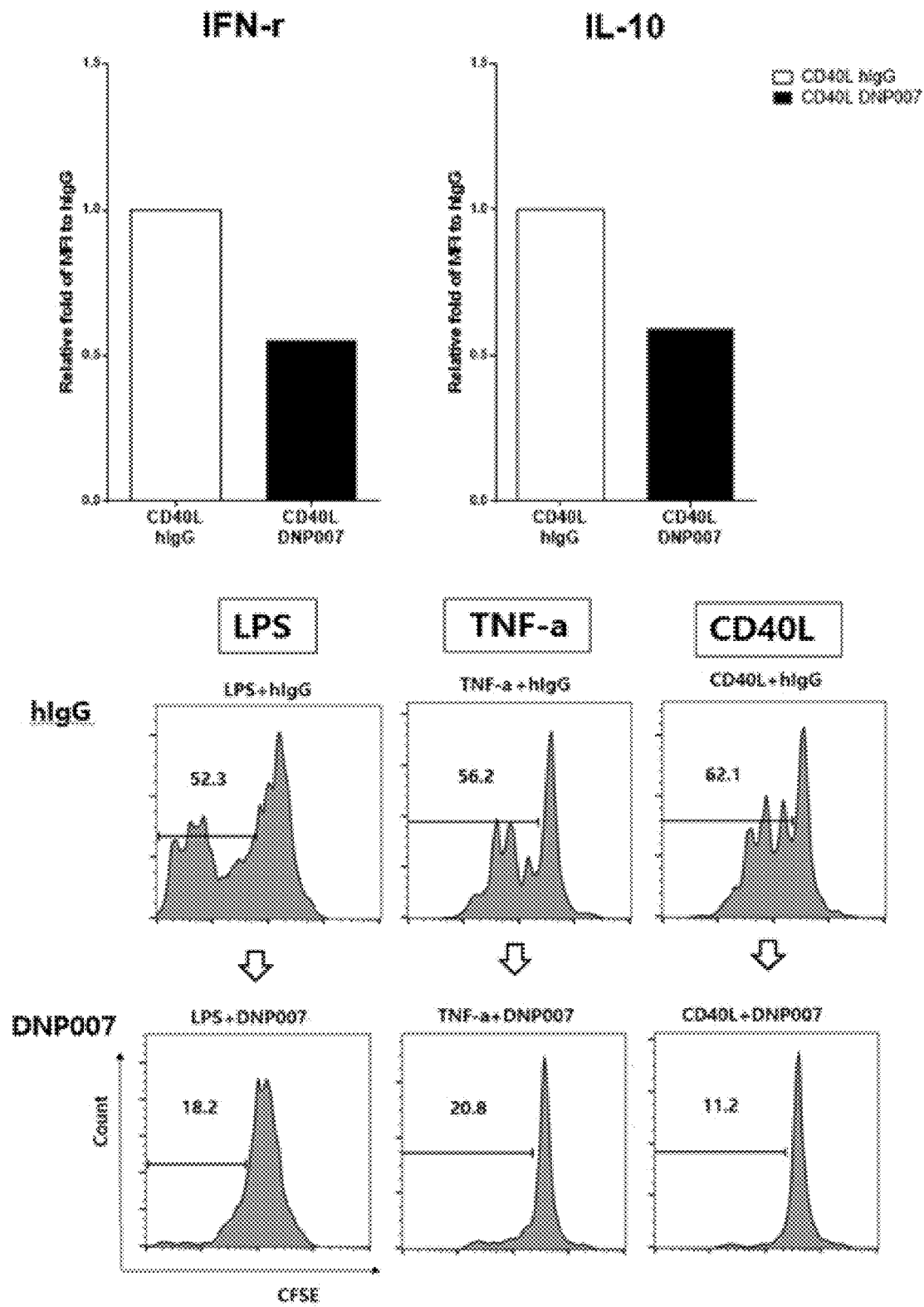
FIG. 21 shows the degree of T cell proliferation according to various dendritic cell maturation pathways (LPS stimulation, TNF-a stimulation, and CD40L stimulation) and the degree of production of interferon gamma (IFN-r), an inflammatory cytokine, of T cells cultured with dendritic cells treated with humanized antibody DNP007 obtained according to one example.

The obtained results are shown in FIG. 21. As shown in FIG. 21, T cells cultured with the control antibody-treated dendritic cells showed active cell proliferation and highly expressed IFN-γ and IL-10, which are representative of proinflammatory cytokines. In contrast, T cells treated with dendritic cells with restricted maturation by treatment with test antibody DNP007 inhibited proliferation despite stimulation by the anti-CD3 antibody and markedly reduced proinflammatory cytokine secretion.

These results indicate that the antibodies provided herein affect both the maturation pathways of dendritic cells (the canonical pathway induced by LPS and TNF-α stimulation and the non-canonical pathway induced by CD40L), and T cells sensitized by dendritic cells whose maturation is inhibited limit proliferation and expression of proinflammatory cytokines. That is, the semi-mature dendritic cells induced by the antibodies provided herein inhibit the activity and proliferation of T cells.

Example 6. Effect of Antibody on the Treatment of Immune-Related Diseases (In Vivo)

6-1. Rheumatoid Arthritis Treatment Effect Test

Figure 22A:
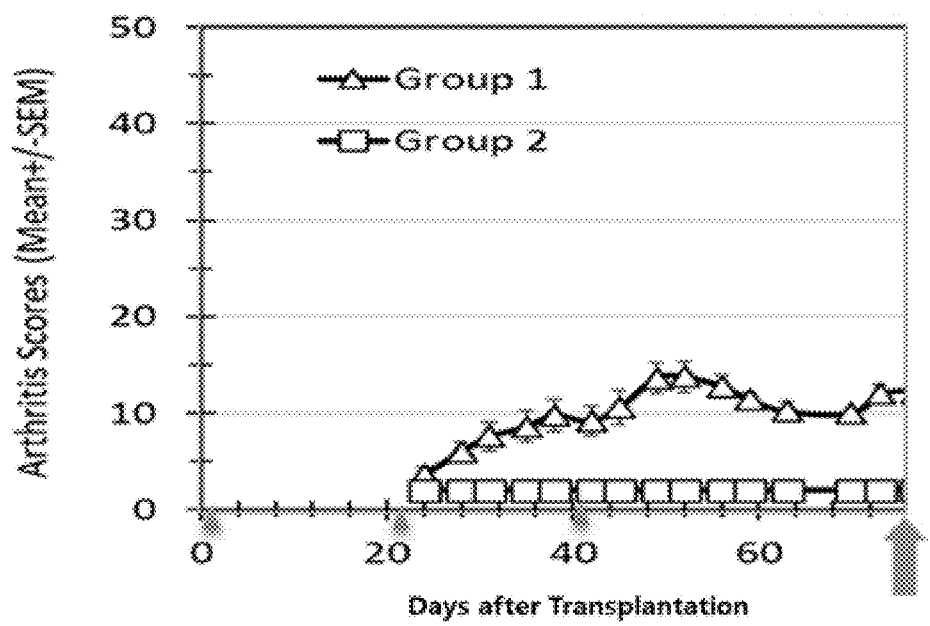
FIGS. 22a to 22c are results of confirming the therapeutic effect of rheumatoid arthritis of the humanized antibody DNP007 obtained according to one example in an animal model of rheumatoid arthritis.

In order to confirm whether the antibody provided herein is effective for rheumatoid arthritis, a mild and moderate rheumatoid arthritis model was prepared as follows: On the first day, 4 mg of Type II Bovine collagen (Chodrex inc, Cat. #: 20021) was prepared with CFA (Sigma Cat. #: F5881) in an amount of 0.5 ml+0.5 ml in a 1:1 volume ratio, divided into 10 places of 0.1 ml each, and injected into the epidermis of primate animals (Cynomolgus Macaques (*Macaca fascicularis*), sex: female, age: 2.5-5 years, weight: 2-6 kg, source: PrimGen). On the 21st and 45th days, the injection was carried out in the same way, except that the second and third injection was replaced with IFA (Sigma, Cat. #: F5506) instead of CFA. The control group was injected with PBS in the same manner. The RA score, which measures the incidence of arthritis, was semi-quantitatively scored on the degree of swelling or red color change in each joint of the animal (FIG. 22a). The antibody DNP007 (H17L4 antibody) provided herein was administered at 8 mg/kg twice a week from the 70th day after the first collagen treatment, and the Arthritis score of 64 joints was measured according to the evaluation criteria. In addition, Bovine collagen-specific antibodies were tested from the plasma of the administered animals. The change of the Bovine collagen specific antibody was measured using the ELISA kit (Cat. #: 2052T) of Chondrex.

Figure 22B:
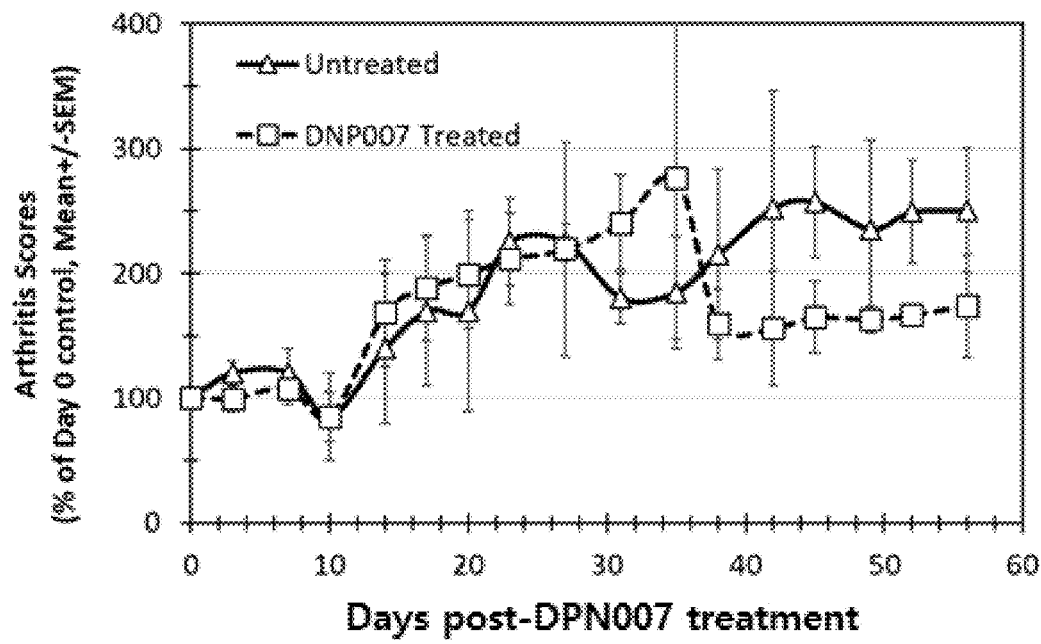
Figure 22C:
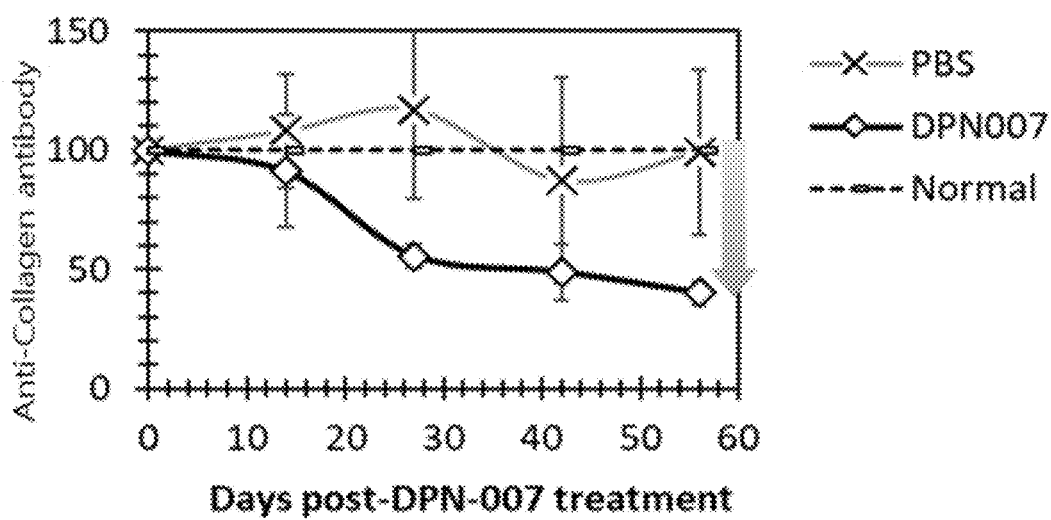

The obtained results are shown in FIGS. 22b and 22c. As a result, the Arthritics score decreased in the group (n=3)

administered with the test antibody DNP007 compared to the non-administered group (n=2) (FIG. 22b), and the anti-collagen antibody, a direct immunological factor of the disease, was also significantly reduced (FIG. 22c). These results show that the antibodies provided herein are effective in the treatment of rheumatoid arthritis.

6-2. Graft Versus Host Disease Treatment Effect Test

Graft-versus-host disease (GVHD) is one of the side effects of transplanted patients (recipients) when allogeneic organs (e.g., bone marrow) are transplanted and a phenomenon that occurs when NK cells or T cells of donor attack the recipient's organs. In order to confirm whether the antibody provided herein is effective in inhibiting graft versus host disease during allogeneic bone marrow transplantation, peripheral blood mononuclear cell (PBMC) were added to NOD-SCID mice, and the reconstitution and survival rate of T cells were compared with those of the control group.

More specifically, the graft-versus-host disease (GVHD) model was established by irradiating NSG (NOD.Cg-Prkdcscid Il2rgtm1Wjl/SzJ) female mice with 1.6 Gy and then injecting human PBMCs. Human PBMC were obtained by centrifugation in a Leucosep™ tube (Greiner bio-one, 227290) using Ficoll (GE Healthcare, 17544202) and separating the middle white layer. The isolated human PBMC was administered intraperitoneally at $1 \times 10^7$ cells/200 μL per mouse.

A test group was prepared by administering the antibody DNP007 (H17L4 antibody) provided herein at a dose of 10 mg/kg twice a week for a total of 12 times for 6 weeks, and a positive control was prepared by administering CTLA-4-Ig (Bio X cell, BE0099) at a dose of 10 mg/kg twice a week for a total of 12 times for 6 weeks. G1 (n=3) is a negative control group without PBMC administration, and G2 (n=7) is a negative control group in which GVHD is induced and PBS is administered as a vehicle. In addition, G3 (n=7) is a positive control group administered with CTLA-4-Ig, and G4 (n=7) is a test group administered with test antibody DNP007. Measurement of GVHD induction and treatment effect was recorded by scoring five clinical criteria (weight loss, posture, activity, fur, skin).

Figure 23A:
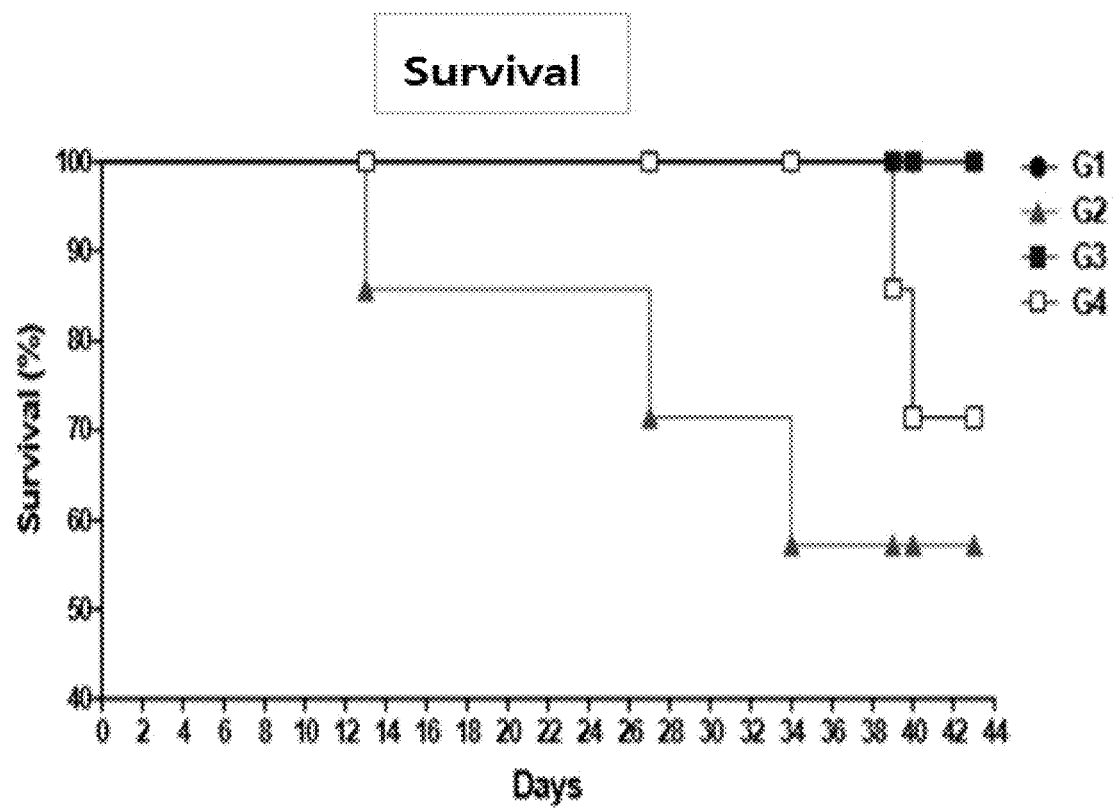
FIGS. 23a and 23b are the results of confirming the graft-versus-host disease inhibitory effect of the humanized antibody DNP007 obtained according to one example in the graft-versus-host disease animal model.
Figure 23B:
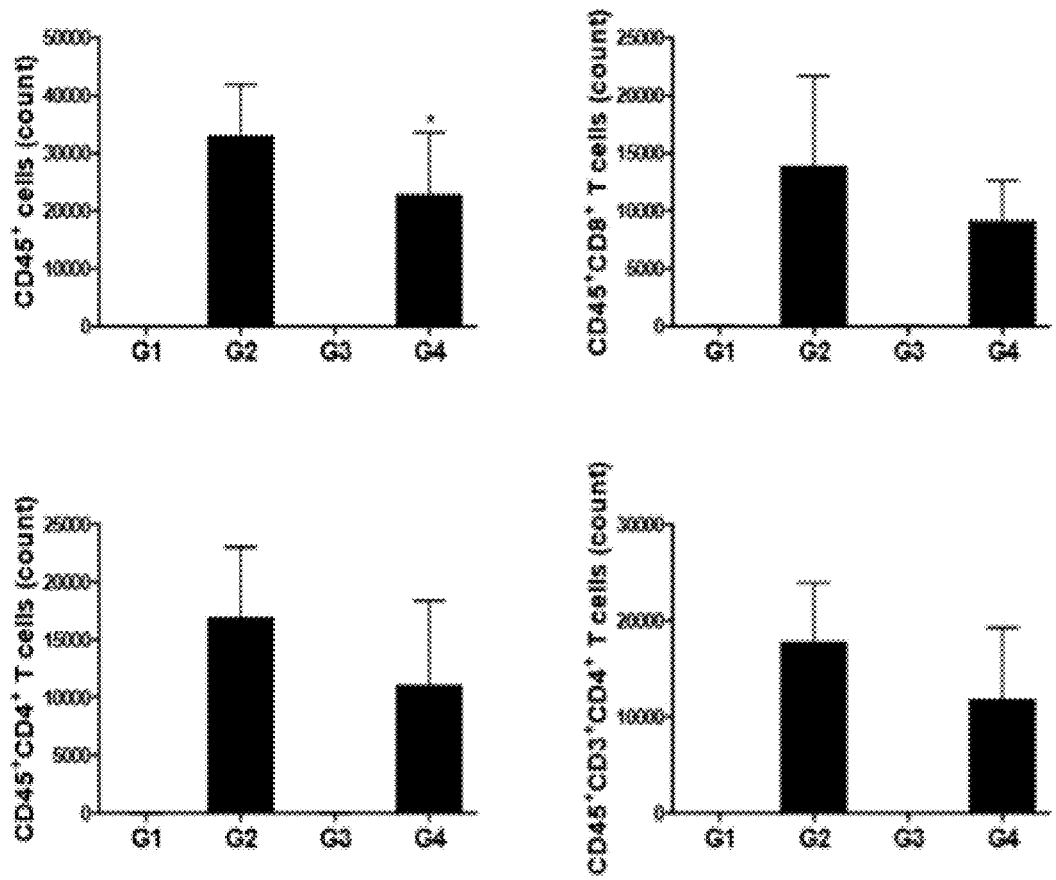

The obtained results are shown in FIGS. 23a and 23b. As a result, it was confirmed that the test group (G4) to which the antibody provided herein was administered had a significantly improved survival rate than that of the negative control group G2 (FIG. 23a), and it was confirmed that re-establishment of human T cells was normally performed well (FIG. 23b). These results show that the antibody provided herein has an effect of preventing graft versus host disease that occurs during allogeneic bone marrow transplantation and enabling re-establishment of normal donor T cells.

---

The invention claimed is:

1. An anti-ICAM-1 antibody or an antigen-binding fragment thereof, comprising the following complementarity determining regions (CDRs):
   CDR-H1 comprising the amino acid sequence of SEQ ID NO: 1,
   CDR-H2 comprising the amino acid sequence of SEQ ID NO: 2,
   CDR-H3 comprising the amino acid sequence of SEQ ID NO: 3,
   CDR-L1 comprising the amino acid sequence of SEQ ID NO: 4,
   CDR-L2 comprising the amino acid sequence of SEQ ID NO: 5, and
   CDR-L3 comprising the amino acid sequence of SEQ ID NO: 6,
   wherein the anti-ICAM-1 antibody or an antigen-binding fragment thereof comprises
   a heavy chain variable region comprising the amino acid sequence of SEQ ID NOs: 27; and
   a light chain variable region comprising the amino acid sequence of SEQ ID NOs: 35 or 38.

2. The anti-ICAM-1 antibody or the antigen-binding fragment thereof according to claim 1, wherein the anti-ICAM-1 antibody is a humanized antibody.

3. The anti-ICAM-1 antibody or the antigen-binding fragment thereof according to claim 1, wherein the antigen-binding fragment is scFv, (scFv) 2, Fab, Fab', or F (ab') 2 of the anti-ICAM-1 antibody.

4. A method of treatment of immune cell mediated disease, comprising administering a pharmaceutically effective amount of the anti-ICAM-1 antibody or the antigen-binding fragment thereof according to claim 1 to a subject in need of treatment of the immune cell mediated disease,
   wherein the immune cell mediated disease is rheumatoid arthritis or graft versus host disease.

5. A nucleic acid molecule encoding
   the amino acid sequence of SEQ ID NO: 27; and
   the amino acid sequence of SEQ ID NOs: 35 or 38.

6. A recombinant vector comprising the nucleic acid molecule of claim 5.

7. A recombinant cell comprising the recombinant vector of claim 6.

8. A method for producing an anti-ICAM-1 antibody or an antigen-binding fragment thereof, comprising a step of culturing the recombinant cell of claim 7.

9. A method for detecting ICAM-1, comprising contacting a biological sample with the anti-ICAM-1 antibody or the antigen-binding fragment thereof of claim 1.

10. A pharmaceutical composition comprising the anti-ICAM-1 antibody or the antigen-binding fragment thereof according to claim 1.

* * * * *

SEQUENCE LISTING

```
<160> NUMBER OF SEQ ID NOS: 107

<210> SEQ ID NO 1
<211> LENGTH: 8
<212> TYPE: PRT
<213> ORGANISM: Artificial Sequence
<220> FEATURE:
<223> OTHER INFORMATION: Synthetic (VH-CDR1)

<400> SEQUENCE: 1

Gly Tyr Thr Phe Thr Asp Tyr Ala
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic (VH-CDR2)

<400> SEQUENCE: 2

Ile Ser Thr Tyr Ser Gly Asn Thr
1               5

<210> SEQ ID NO 3
<211> LENGTH: 13
<212> TYPE: PRT
<213> ORGANISM: Artificial Sequence
<220> FEATURE:
<223> OTHER INFORMATION: Synthetic (VH-CDR3)

<400> SEQUENCE: 3

Ala Arg Ser Leu Tyr Phe Gly Ser Ser Gly Phe Asp Tyr
1               5                   10

<210> SEQ ID NO 4
<211> LENGTH: 11
```

```
<212> TYPE: PRT
<213> ORGANISM: Artificial Sequence
<220> FEATURE:
<223> OTHER INFORMATION: Synthetic (VL-CDR1)

<400> SEQUENCE: 4

Gln Thr Leu Val Tyr Arg Asn Gly Asn Thr Tyr
1               5                   10

<210> SEQ ID NO 5
<211> LENGTH: 3
<212> TYPE: PRT
<213> ORGANISM: Artificial Sequence
<220> FEATURE:
<223> OTHER INFORMATION: Synthetic (VL-CDR2)

<400> SEQUENCE: 5

Lys Val Ser
1

<210> SEQ ID NO 6
<211> LENGTH: 9
<212> TYPE: PRT
<213> ORGANISM: Artificial Sequence
<220> FEATURE:
<223> OTHER INFORMATION: Synthetic (VL-CDR3)

<400> SEQUENCE: 6

Ser Gln Asn Thr His Phe Pro Tyr Thr
1               5

<210> SEQ ID NO 7
<211> LENGTH: 120
<212> TYPE: PRT
<213> ORGANISM: Artificial Sequence
<220> FEATURE:
<223> OTHER INFORMATION: Synthetic (Chimeric VH)

<400> SEQUENCE: 7

Gln Val Gln Leu Gln Gln Ser Gly Ala Glu Leu Val Arg Pro Gly Val
1               5                   10                  15

Ser Val Lys Ile Ser Cys Lys Gly Ser Gly Tyr Thr Phe Thr Asp Tyr
            20                  25                  30

Ala Leu His Trp Val Lys Gln Ser His Ala Lys Ser Leu Glu Trp Ile
        35                  40                  45

Gly Val Ile Ser Thr Tyr Ser Gly Asn Thr Asp Tyr Asn Gln Lys Phe
    50                  55                  60

Arg Gly Lys Ala Thr Met Thr Val Asp Lys Ser Ser Thr Thr Ala Tyr
65                  70                  75                  80

Leu Glu Leu Ala Arg Leu Thr Ser Glu Asp Ser Ala Ile His Tyr Cys
                85                  90                  95

Ala Arg Ser Leu Tyr Phe Gly Ser Ser Gly Phe Asp Tyr Trp Gly Gln
            100                 105                 110

Gly Thr Ala Leu Thr Val Ser Ser
        115                 120

<210> SEQ ID NO 8
<211> LENGTH: 111
<212> TYPE: PRT
<213> ORGANISM: Artificial Sequence
<220> FEATURE:
<223> OTHER INFORMATION: Synthetic (Chimeric VL )

<400> SEQUENCE: 8
```

```
Asp Val Val Leu Thr Gln Thr Pro Leu Ser Leu Pro Val Asn Leu Gly
1               5                   10                  15

Asp Gln Ala Ser Ile Ser Cys Arg Ser Ser Gln Thr Leu Val Tyr Arg
                20                  25                  30

Asn Gly Asn Thr Tyr Leu His Trp Tyr Leu Gln Lys Ala Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Asn
                85                  90                  95

Thr His Phe Pro Tyr Thr Phe Gly Gly Gly Thr Lys Ile Lys Arg
            100                 105                 110
```

<210> SEQ ID NO 9
<211> LENGTH: 363
<212> TYPE: DNA
<213> ORGANISM: Artificial Sequence
<220> FEATURE:
<223> OTHER INFORMATION: Synthetic (Chimeric VH coding nucleic acid
      sequence)

<400> SEQUENCE: 9

```
caggtgcagc tgcagcagag cggcgcggaa ctggtgcgcc cgggcgtgag cgtgaaaatt    60
agctgcaaag gcagcggcta cctttacc gattatgcgc tgcattgggt gaaacagagc     120
catgcgaaaa gcctggaatg gattggcgtg attagcacct atagcggcaa caccgattat    180
aaccagaaat tcgcggcaa agcgaccatg accgtggata aaagcagcac caccgcgtat    240
ctggaactgg cgcgcctgac cagcgaagat agcgcgattc attattgcgc gcgcagcctg    300
tattttggca gcagcggctt tgattattgg ggccagggca ccgcgctgac cgtgagcagc    360
taa                                                                  363
```

<210> SEQ ID NO 10
<211> LENGTH: 333
<212> TYPE: DNA
<213> ORGANISM: Artificial Sequence
<220> FEATURE:
<223> OTHER INFORMATION: Synthetic (Chimeric VL coding nucleic acid
      sequence)

<400> SEQUENCE: 10

```
gatgtggtgc tgacccagac cccgctgagc ctgccggtga acctgggcga tcaggcgagc    60
attagctgcc gcagcagcca gaccctggtg tatcgcaacg gcaacaccta tctgcattgg    120
tatctgcaga aagcgggcca gagcccgaaa ctgctgattt ataaagtgag caaccgcttt    180
agcggcgtgc cggatcgctt tagcggcagc ggcagcggca ccgatttac cctgaaaatt    240 agccgcgtgg aagcggaaga tctgggcgtg tattttgca gccagaacac ccattttccg    300 tataccttg gcggcggcac caaaattaaa cgc                                  333
```

<210> SEQ ID NO 11
<211> LENGTH: 120
<212> TYPE: PRT
<213> ORGANISM: Artificial Sequence
<220> FEATURE:
<223> OTHER INFORMATION: Synthetic (VH1)

<400> SEQUENCE: 11

Gln Val Gln Leu Val Gln Ser Gly Ala Glu Val Lys Lys Pro Gly Ala
1               5                   10                  15

Ser Val Lys Ile Ser Cys Lys Gly Ser Gly Tyr Thr Phe Thr Asp Tyr
            20                  25                  30

Ala Leu His Trp Val Arg Gln Ala Pro Gly Gln Arg Leu Glu Trp Ile
        35                  40                  45

Gly Val Ile Ser Thr Tyr Ser Gly Asn Thr Asp Tyr Asn Gln Lys Phe
    50                  55                  60

Arg Gly Arg Ala Thr Ile Thr Arg Asp Thr Ser Ala Ser Thr Ala Tyr
65              70                  75                  80

Met Glu Leu Ser Ser Leu Arg Ser Glu Asp Thr Ala Val Tyr Tyr Cys
            85                  90                  95

Ala Arg Ser Leu Tyr Phe Gly Ser Gly Phe Asp Tyr Trp Gly Gln
            100                 105                 110

Gly Thr Ala Leu Thr Val Ser Ser
        115                 120

<210> SEQ ID NO 12
<211> LENGTH: 120
<212> TYPE: PRT
<213> ORGANISM: Artificial Sequence
<220> FEATURE:
<223> OTHER INFORMATION: Synthetic (VH2)

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
            20                  25                  30

Ala Leu His Trp Val Arg Gln Ala Pro Gly Gln Arg Leu Glu Trp Met
        35                  40                  45

Gly Val Ile Ser Thr Tyr Ser Gly Asn Thr Asp Tyr Asn Gln Lys Phe
    50                  55                  60

Arg Gly Arg Val Thr Met Thr Val Asp Thr Ser Ala Ser Thr Ala Tyr
65              70                  75                  80

Met Glu Leu Ser Ser Leu Arg Ser Glu Asp Thr Ala Val His Tyr Cys
            85                  90                  95

Ala Arg Ser Leu Tyr Phe Gly Ser Gly Phe Asp Tyr Trp Gly Gln
            100                 105                 110

Gly Thr Ala Leu Thr Val Ser Ser
        115                 120

<210> SEQ ID NO 13
<211> LENGTH: 120
<212> TYPE: PRT
<213> ORGANISM: Artificial Sequence
<220> FEATURE:
<223> OTHER INFORMATION: Synthetic (VH3)

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ala Leu His Trp Val Arg Gln Ala Pro Gly Gln Arg Leu Glu Trp Met
        35                  40                  45

Gly Val Ile Ser Thr Tyr Ser Gly Asn Thr Asp Tyr Asn Gln Lys Phe

```
                    50                  55                  60
Arg Gly Arg Ala Thr Ile Thr Arg Asp Lys Ser Ala Ser Thr Ala Tyr
 65                  70                  75                  80

Leu Glu Leu Ser Ser Leu Arg Ser Glu Asp Thr Ala Val His Tyr Cys
                    85                  90                  95

Ala Arg Ser Leu Tyr Phe Gly Ser Ser Gly Phe Asp Tyr Trp Gly Gln
                100                 105                 110

Gly Thr Ala Leu Thr Val Ser Ser
            115                 120

<210> SEQ ID NO 14
<211> LENGTH: 120
<212> TYPE: PRT
<213> ORGANISM: Artificial Sequence
<220> FEATURE:
<223> OTHER INFORMATION: Synthetic (VH4)

<400> SEQUENCE: 14

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
                20                  25                  30

Ala Leu His Trp Val Arg Gln Ala Pro Gly Gln Arg Leu Glu Trp Ile
            35                  40                  45

Gly Val Ile Ser Thr Tyr Ser Gly Asn Thr Asp Tyr Asn Gln Lys Phe
        50                  55                  60

Arg Gly Arg Val Thr Met Thr Arg Asp Thr Ser Ala Thr Thr Ala Tyr
 65                  70                  75                  80

Leu Glu Leu Ser Ser Leu Arg Ser Glu Asp Thr Ala Val Tyr Tyr Cys
                    85                  90                  95

Ala Arg Ser Leu Tyr Phe Gly Ser Ser Gly Phe Asp Tyr Trp Gly Gln
                100                 105                 110

Gly Thr Ala Leu Thr Val Ser Ser
            115                 120

<210> SEQ ID NO 15
<211> LENGTH: 120
<212> TYPE: PRT
<213> ORGANISM: Artificial Sequence
<220> FEATURE:
<223> OTHER INFORMATION: Synthetic (VH5)

<400> SEQUENCE: 15

Gln Val Gln Leu Val Gln Ser Gly Ala Glu Val Lys Lys Pro Gly Ala
 1               5                  10                  15

Ser Val Lys Ile Ser Cys Lys Ala Ser Gly Tyr Thr Phe Thr Asp Tyr
                20                  25                  30

Ala Leu His Trp Val Arg Gln Ala Pro Gly Gln Arg Leu Glu Trp Met
            35                  40                  45

Gly Val Ile Ser Thr Tyr Ser Gly Asn Thr Asp Tyr Asn Gln Lys Phe
        50                  55                  60

Arg Gly Arg Val Thr Ile Thr Val Asp Lys Ser Ala Thr Thr Ala Tyr
 65                  70                  75                  80

Met Glu Leu Ser Ser Leu Arg Ser Glu Asp Thr Ala Val Tyr Tyr Cys
                    85                  90                  95

Ala Arg Ser Leu Tyr Phe Gly Ser Ser Gly Phe Asp Tyr Trp Gly Gln
                100                 105                 110
```

Gly Thr Ala Leu Thr Val Ser Ser
        115                 120

<210> SEQ ID NO 16
<211> LENGTH: 120
<212> TYPE: PRT
<213> ORGANISM: Artificial Sequence
<220> FEATURE:
<223> OTHER INFORMATION: Synthetic (VH6)

<400> SEQUENCE: 16

Gln Val Gln Leu Val Gln Ser Gly Ala Glu Val Val Lys Pro Gly Ala
1               5                   10                  15

Ser Val Lys Val Ser Cys Lys Gly Ser Gly Tyr Thr Phe Thr Asp Tyr
            20                  25                  30

Ala Leu His Trp Val Arg Gln Ala Pro Gly Gln Arg Leu Glu Trp Ile
        35                  40                  45

Gly Val Ile Ser Thr Tyr Ser Gly Asn Thr Lys Tyr Ser Gln Lys Phe
    50                  55                  60

Gln Gly Lys Ala Thr Ile Thr Arg Asp Lys Ser Ala Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Ser Leu Tyr Phe Gly Ser Ser Gly Phe Asp Tyr Trp Gly Gln
            100                 105                 110

Gly Thr Ala Leu Thr Val Ser Ser
        115                 120

<210> SEQ ID NO 17
<211> LENGTH: 120
<212> TYPE: PRT
<213> ORGANISM: Artificial Sequence
<220> FEATURE:
<223> OTHER INFORMATION: Synthetic (VH7)

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
            20                  25                  30

Ala Leu His Trp Val Lys Gln Ala Pro Gly Gln Arg Leu Glu Trp Met
        35                  40                  45

Gly Val Ile Ser Thr Tyr Ser Gly Asn Thr Lys Tyr Ser Gln Lys Phe
    50                  55                  60

Gln Gly Arg Ala Thr Met Thr Arg Asp Thr Ser Ala Thr Thr Ala Tyr
65                  70                  75                  80

Met Glu Leu Ser Ser Leu Arg Ser Glu Asp Thr Ala Ile His Tyr Cys
                85                  90                  95

Ala Arg Ser Leu Tyr Phe Gly Ser Ser Gly Phe Asp Tyr Trp Gly Gln
            100                 105                 110

Gly Thr Ala Leu Thr Val Ser Ser
        115                 120

<210> SEQ ID NO 18
<211> LENGTH: 120
<212> TYPE: PRT
<213> ORGANISM: Artificial Sequence
<220> FEATURE:
<223> OTHER INFORMATION: Synthetic (VH8)

```
<400> SEQUENCE: 18

Gln Val Gln Leu Gln Gln Ser Gly Ala Glu Val Lys Lys Pro Gly Ala
1               5                   10                  15

Ser Val Lys Ile Ser Cys Lys Gly Ser Gly Tyr Thr Phe Thr Asp Tyr
            20                  25                  30

Ala Leu His Trp Val Arg Gln Ala Pro Gly Gln Ser Leu Glu Trp Met
        35                  40                  45

Gly Val Ile Ser Thr Tyr Ser Gly Asn Thr Lys Tyr Ser Gln Lys Phe
    50                  55                  60

Gln Gly Arg Ala Thr Met Thr Arg Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Leu Tyr Phe Gly Ser Ser Gly Phe Asp Tyr Trp Gly Gln
            100                 105                 110

Gly Thr Ala Leu Thr Val Ser Ser
        115                 120

<210> SEQ ID NO 19
<211> LENGTH: 120
<212> TYPE: PRT
<213> ORGANISM: Artificial Sequence
<220> FEATURE:
<223> OTHER INFORMATION: Synthetic (VH9)

<400> SEQUENCE: 19

Gln Val Gln Leu Gln Gln Ser Gly Ala Glu Val Val Lys Pro Gly Ala
1               5                   10                  15

Ser Val Lys Val Ser Cys Lys Ala Ser Gly Tyr Thr Phe Thr Asp Tyr
            20                  25                  30

Ala Leu His Trp Val Arg Gln Ala Pro Gly Gln Ser Leu Glu Trp Met
        35                  40                  45

Gly Val Ile Ser Thr Tyr Ser Gly Asn Thr Lys Tyr Ser Gln Lys Phe
    50                  55                  60

Gln Gly Lys Val Thr Ile Thr Val Asp Thr Ser Ala Thr Thr Ala Tyr
65                  70                  75                  80

Met Glu Leu Ser Ser Leu Arg Ser Glu Asp Thr Ala Val His Tyr Cys
                85                  90                  95

Ala Arg Ser Leu Tyr Phe Gly Ser Ser Gly Phe Asp Tyr Trp Gly Gln
            100                 105                 110

Gly Thr Ala Leu Thr Val Ser Ser
        115                 120

<210> SEQ ID NO 20
<211> LENGTH: 120
<212> TYPE: PRT
<213> ORGANISM: Artificial Sequence
<220> FEATURE:
<223> OTHER INFORMATION: Synthetic (VH10)

<400> SEQUENCE: 20

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Asp Tyr
            20                  25                  30

Ala Leu His Trp Val Lys Gln Ala Pro Gly Gln Ser Leu Glu Trp Met
        35                  40                  45
```

Gly Val Ile Ser Thr Tyr Ser Gly Asn Thr Lys Tyr Ser Gln Lys Phe
            50                  55                  60

Gln Gly Arg Val Thr Ile Thr Val Asp Thr Ser Ala Ser Thr Ala Tyr
65                  70                  75                  80

Leu Glu Leu Ser Ser Leu Arg Ser Glu Asp Thr Ala Ile Tyr Tyr Cys
                85                  90                  95

Ala Arg Ser Leu Tyr Phe Gly Ser Ser Gly Phe Asp Tyr Trp Gly Gln
            100                 105                 110

Gly Thr Ala Leu Thr Val Ser Ser
            115                 120

<210> SEQ ID NO 21
<211> LENGTH: 120
<212> TYPE: PRT
<213> ORGANISM: Artificial Sequence
<220> FEATURE:
<223> OTHER INFORMATION: Synthetic (VH11)

<400> SEQUENCE: 21

Gln Val Gln Leu Gln Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Ala Leu His Trp Val Arg Gln Ala Pro Gly Gln Arg Leu Glu Trp Ile
        35                  40                  45

Gly Val Ile Ser Thr Tyr Ser Gly Asn Thr Lys Tyr Ser Gln Lys Phe
            50                  55                  60

Gln Gly Lys Val Thr Ile Thr Arg Asp Thr Ser Ala Ser Thr Ala Tyr
65                  70                  75                  80

Leu Glu Leu Ser Ser Leu Arg Ser Glu Asp Thr Ala Ile His Tyr Cys
                85                  90                  95

Ala Arg Ser Leu Tyr Phe Gly Ser Ser Gly Phe Asp Tyr Trp Gly Gln
            100                 105                 110

Gly Thr Ala Leu Thr Val Ser Ser
            115                 120

<210> SEQ ID NO 22
<211> LENGTH: 120
<212> TYPE: PRT
<213> ORGANISM: Artificial Sequence
<220> FEATURE:
<223> OTHER INFORMATION: Synthetic (VH12)

<400> SEQUENCE: 22

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ala Leu His Trp Val Lys Gln Ala Pro Gly Gln Arg Leu Glu Trp Ile
        35                  40                  45

Gly Val Ile Ser Thr Tyr Ser Gly Asn Thr Lys Tyr Ser Gln Lys Phe
            50                  55                  60

Gln Gly Arg Val Thr Met Thr Val Asp Lys Ser Ala Thr Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Leu Tyr Phe Gly Ser Ser Gly Phe Asp Tyr Trp Gly Gln
            100                 105                 110

```
Gly Thr Ala Leu Thr Val Ser Ser
        115                 120

<210> SEQ ID NO 23
<211> LENGTH: 120
<212> TYPE: PRT
<213> ORGANISM: Artificial Sequence
<220> FEATURE:
<223> OTHER INFORMATION: Synthetic (VH13)

<400> SEQUENCE: 23

Gln Val Gln Leu Val Gln Ser Gly Ala Glu Val Lys Lys Pro Gly Ala
1               5                   10                  15

Ser Val Lys Ile Ser Cys Lys Gly Ser Gly Tyr Thr Phe Thr Asp Tyr
            20                  25                  30

Ala Leu His Trp Val Arg Gln Ala Pro Gly Gln Arg Leu Glu Trp Met
        35                  40                  45

Gly Val Ile Ser Thr Tyr Ser Gly Asn Thr Asp Tyr Asn Gln Lys Phe
    50                  55                  60

Arg Gly Arg Val Thr Ile Thr Arg Asp Lys Ser Ala Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Ser Leu Tyr Phe Gly Ser Gly Phe Asp Tyr Trp Gly Gln
            100                 105                 110

Gly Thr Ala Leu Thr Val Ser Ser
        115                 120

<210> SEQ ID NO 24
<211> LENGTH: 120
<212> TYPE: PRT
<213> ORGANISM: Artificial Sequence
<220> FEATURE:
<223> OTHER INFORMATION: Synthetic (VH14)

<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
            20                  25                  30

Ala Leu His Trp Val Arg Gln Ala Pro Gly Gln Arg Leu Glu Trp Met
        35                  40                  45

Gly Val Ile Ser Thr Tyr Ser Gly Asn Thr Asp Tyr Asn Gln Lys Phe
    50                  55                  60

Arg Gly Arg Val Thr Ile Thr Val Asp Thr Ser Ala Thr Thr Ala Tyr
65                  70                  75                  80

Met Glu Leu Ser Ser Leu Arg Ser Glu Asp Thr Ala Val His Tyr Cys
                85                  90                  95

Ala Arg Ser Leu Tyr Phe Gly Ser Gly Phe Asp Tyr Trp Gly Gln
            100                 105                 110

Gly Thr Ala Leu Thr Val Ser Ser
        115                 120

<210> SEQ ID NO 25
<211> LENGTH: 120
<212> TYPE: PRT
<213> ORGANISM: Artificial Sequence
<220> FEATURE:
<223> OTHER INFORMATION: Synthetic (VH15)
```

<400> SEQUENCE: 25

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
            20                  25                  30

Ala Leu His Trp Val Arg Gln Ala Pro Gly Gln Arg Leu Glu Trp Ile
        35                  40                  45

Gly Val Ile Ser Thr Tyr Ser Gly Asn Thr Asp Tyr Asn Gln Lys Phe
    50                  55                  60

Arg Gly Arg Val Thr Met Thr Arg Asp Thr Ser Ala Ser Thr Ala Tyr
65                  70                  75                  80

Met Glu Leu Ser Ser Leu Arg Ser Glu Asp Thr Ala Val His Tyr Cys
                85                  90                  95

Ala Arg Ser Leu Tyr Phe Gly Ser Ser Gly Phe Asp Tyr Trp Gly Gln
            100                 105                 110

Gly Thr Ala Leu Thr Val Ser Ser
            115                 120

<210> SEQ ID NO 26
<211> LENGTH: 120
<212> TYPE: PRT
<213> ORGANISM: Artificial Sequence
<220> FEATURE:
<223> OTHER INFORMATION: Synthetic (VH16)

<400> SEQUENCE: 26

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
            20                  25                  30

Ala Leu His Trp Val Arg Gln Ala Pro Gly Gln Arg Leu Glu Trp Met
        35                  40                  45

Gly Val Ile Ser Thr Tyr Ser Gly Asn Thr Asp Tyr Asn Gln Lys Phe
    50                  55                  60

Arg Gly Arg Ala Thr Met Thr Arg Asp Thr Ser Ala Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Ser Leu Tyr Phe Gly Ser Ser Gly Phe Asp Tyr Trp Gly Gln
            100                 105                 110

Gly Thr Ala Leu Thr Val Ser Ser
            115                 120

<210> SEQ ID NO 27
<211> LENGTH: 120
<212> TYPE: PRT
<213> ORGANISM: Artificial Sequence
<220> FEATURE:
<223> OTHER INFORMATION: Synthetic (VH17)

<400> SEQUENCE: 27

Gln Val Gln Leu Val Gln Ser Gly Ala Glu Val Lys Lys Pro Gly Ala
1               5                   10                  15

Ser Val Lys Ile Ser Cys Lys Gly Ser Gly Tyr Thr Phe Thr Asp Tyr
            20                  25                  30

Ala Leu His Trp Val Arg Gln Ala Pro Gly Gln Arg Leu Glu Trp Met
        35                  40                  45

Gly Val Ile Ser Thr Tyr Ser Gly Asn Thr Asp Tyr Asn Gln Lys Phe
            50                  55                  60

Arg Gly Arg Ala Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                    85                  90                  95

Ala Arg Ser Leu Tyr Phe Gly Ser Ser Gly Phe Asp Tyr Trp Gly Gln
                100                 105                 110

Gly Thr Ala Leu Thr Val Ser Ser
            115                 120

<210> SEQ ID NO 28
<211> LENGTH: 120
<212> TYPE: PRT
<213> ORGANISM: Artificial Sequence
<220> FEATURE:
<223> OTHER INFORMATION: Synthetic (VH18)

<400> SEQUENCE: 28

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
                20                  25                  30

Ala Leu His Trp Val Arg Gln Ala Pro Gly Gln Arg Leu Glu Trp Ile
            35                  40                  45

Gly Val Ile Ser Thr Tyr Ser Gly Asn Thr Asp Tyr Asn Gln Lys Phe
            50                  55                  60

Arg Gly Arg Val Thr Ile Thr Arg Asp Lys Ser Ala Thr Thr Ala Tyr
65                  70                  75                  80

Met Glu Leu Ser Ser Leu Arg Ser Glu Asp Thr Ala Val Tyr Tyr Cys
                    85                  90                  95

Ala Arg Ser Leu Tyr Phe Gly Ser Ser Gly Phe Asp Tyr Trp Gly Gln
                100                 105                 110

Gly Thr Ala Leu Thr Val Ser Ser
            115                 120

<210> SEQ ID NO 29
<211> LENGTH: 120
<212> TYPE: PRT
<213> ORGANISM: Artificial Sequence
<220> FEATURE:
<223> OTHER INFORMATION: Synthetic (VH19)

<400> SEQUENCE: 29

Gln Val Gln Leu Val Gln Ser Gly Ala Glu Val Lys Lys Pro Gly Ala
1               5                   10                  15

Ser Val Lys Ile Ser Cys Lys Gly Ser Gly Tyr Thr Phe Thr Asp Tyr
                20                  25                  30

Ala Leu His Trp Val Arg Gln Ala Pro Gly Gln Arg Leu Glu Trp Ile
            35                  40                  45

Gly Val Ile Ser Thr Tyr Ser Gly Asn Thr Lys Tyr Ser Gln Lys Phe
            50                  55                  60

Gln Gly Arg Ala Thr Ile Thr Val Asp Thr Ser Ala Thr Thr Ala Tyr
65                  70                  75                  80

Leu Glu Leu Ser Ser Leu Arg Ser Glu Asp Thr Ala Val Tyr Tyr Cys
                    85                  90                  95

Ala Arg Ser Leu Tyr Phe Gly Ser Ser Gly Phe Asp Tyr Trp Gly Gln

Gly Thr Ala Leu Thr Val Ser Ser
        115                 120

<210> SEQ ID NO 30
<211> LENGTH: 120
<212> TYPE: PRT
<213> ORGANISM: Artificial Sequence
<220> FEATURE:
<223> OTHER INFORMATION: Synthetic (VH20)

<400> SEQUENCE: 30

Gln Val Gln Leu Val Gln Ser Gly Ala Glu Val Lys Lys Pro Gly Ala
1               5                   10                  15

Ser Val Lys Ile Ser Cys Lys Gly Ser Gly Tyr Thr Phe Thr Asp Tyr
            20                  25                  30

Ala Leu His Trp Val Arg Gln Ala Pro Gly Gln Arg Leu Glu Trp Ile
        35                  40                  45

Gly Val Ile Ser Thr Tyr Ser Gly Asn Thr Lys Tyr Ser Gln Lys Phe
    50                  55                  60

Gln Gly Arg Ala Thr Met Thr Arg Asp Thr Ser Ala Ser Thr Ala Tyr
65                  70                  75                  80

Leu Glu Leu Ser Ser Leu Arg Ser Glu Asp Thr Ala Val His Tyr Cys
                85                  90                  95

Ala Arg Ser Leu Tyr Phe Gly Ser Ser Gly Phe Asp Tyr Trp Gly Gln
            100                 105                 110

Gly Thr Ala Leu Thr Val Ser Ser
        115                 120

<210> SEQ ID NO 31
<211> LENGTH: 120
<212> TYPE: PRT
<213> ORGANISM: Artificial Sequence
<220> FEATURE:
<223> OTHER INFORMATION: Synthetic (VH21)

<400> SEQUENCE: 31

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
            20                  25                  30

Ala Leu His Trp Val Arg Gln Ala Pro Gly Gln Arg Leu Glu Trp Ile
        35                  40                  45

Gly Val Ile Ser Thr Tyr Ser Gly Asn Thr Lys Tyr Ser Gln Lys Phe
    50                  55                  60

Gln Gly Arg Val Thr Met Thr Val Asp Lys Ser Ala Thr Thr Ala Tyr
65                  70                  75                  80

Leu Glu Leu Ser Ser Leu Arg Ser Glu Asp Thr Ala Val Tyr Tyr Cys
                85                  90                  95

Ala Arg Ser Leu Tyr Phe Gly Ser Ser Gly Phe Asp Tyr Trp Gly Gln
            100                 105                 110

Gly Thr Ala Leu Thr Val Ser Ser
        115                 120

<210> SEQ ID NO 32
<211> LENGTH: 120
<212> TYPE: PRT
<213> ORGANISM: Artificial Sequence
<220> FEATURE:

<223> OTHER INFORMATION: Synthetic (VH22)

<400> SEQUENCE: 32

Gln Val Gln Leu Val Gln Ser Gly Ala Glu Val Lys Lys Pro Gly Ala
1               5                   10                  15

Ser Val Lys Ile Ser Cys Lys Gly Ser Gly Tyr Thr Phe Thr Asp Tyr
            20                  25                  30

Ala Leu His Trp Val Arg Gln Ala Pro Gly Gln Arg Leu Glu Trp Met
        35                  40                  45

Gly Val Ile Ser Thr Tyr Ser Gly Asn Thr Lys Tyr Ser Gln Lys Phe
    50                  55                  60

Gln Gly Arg Ala Thr Met Thr Arg Asp Lys Ser Ala Thr Thr Ala Tyr
65                  70                  75                  80

Met Glu Leu Ser Ser Leu Arg Ser Glu Asp Thr Ala Val His Tyr Cys
                85                  90                  95

Ala Arg Ser Leu Tyr Phe Gly Ser Ser Gly Phe Asp Tyr Trp Gly Gln
            100                 105                 110

Gly Thr Ala Leu Thr Val Ser Ser
            115                 120

<210> SEQ ID NO 33
<211> LENGTH: 120
<212> TYPE: PRT
<213> ORGANISM: Artificial Sequence
<220> FEATURE:
<223> OTHER INFORMATION: Synthetic (VH23)

<400> SEQUENCE: 33

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
            20                  25                  30

Ala Leu His Trp Val Arg Gln Ala Pro Gly Gln Arg Leu Glu Trp Met
        35                  40                  45

Gly Val Ile Ser Thr Tyr Ser Gly Asn Thr Lys Tyr Ser Gln Lys Phe
    50                  55                  60

Gln Gly Arg Ala Thr Met Thr Val Asp Lys Ser Ala Ser Thr Ala Tyr
65                  70                  75                  80

Leu Glu Leu Ser Ser Leu Arg Ser Glu Asp Thr Ala Val His Tyr Cys
                85                  90                  95

Ala Arg Ser Leu Tyr Phe Gly Ser Ser Gly Phe Asp Tyr Trp Gly Gln
            100                 105                 110

Gly Thr Ala Leu Thr Val Ser Ser
            115                 120

<210> SEQ ID NO 34
<211> LENGTH: 120
<212> TYPE: PRT
<213> ORGANISM: Artificial Sequence
<220> FEATURE:
<223> OTHER INFORMATION: Synthetic (VH24)

<400> SEQUENCE: 34

Gln Val Gln Leu Val Gln Ser Gly Ala Glu Val Lys Lys Pro Gly Ala
1               5                   10                  15

Ser Val Lys Ile Ser Cys Lys Gly Ser Gly Tyr Thr Phe Thr Asp Tyr
            20                  25                  30

Ala Leu His Trp Val Arg Gln Ala Pro Gly Gln Arg Leu Glu Trp Ile

```
            35                  40                  45
Gly Val Ile Ser Thr Tyr Ser Gly Asn Thr Lys Tyr Ser Gln Lys Phe
 50                  55                  60

Gln Gly Arg Val Thr Ile Thr Val Asp Lys Ser Ala Thr Thr Ala Tyr
 65                  70                  75                  80

Met Glu Leu Ser Ser Leu Arg Ser Glu Asp Thr Ala Val His Tyr Cys
                 85                  90                  95

Ala Arg Ser Leu Tyr Phe Gly Ser Gly Phe Asp Tyr Trp Gly Gln
                100                 105                 110

Gly Thr Ala Leu Thr Val Ser Ser
        115                 120
```

<210> SEQ ID NO 35
<211> LENGTH: 112
<212> TYPE: PRT
<213> ORGANISM: Artificial Sequence
<220> FEATURE:
<223> OTHER INFORMATION: Synthetic (VL1)

<400> SEQUENCE: 35

```
Asp Val Val Leu Thr Gln Ser Pro Leu Ser Leu Pro Val Thr Leu Gly
 1                   5                  10                  15

Gln Pro Ala Ser Ile Ser Cys Arg Ser Ser Gln Thr Leu Val Tyr Arg
                 20                  25                  30

Asn Gly Asn Thr Tyr Leu His Trp Tyr Gln Gln Arg Pro Gly Gln Ser
             35                  40                  45

Pro Arg Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Phe Cys Ser Gln Asn
                 85                  90                  95

Thr His Phe Pro Tyr Thr Phe Gly Gly Gly Thr Lys Leu Glu Ile Lys
                100                 105                 110
```

<210> SEQ ID NO 36
<211> LENGTH: 112
<212> TYPE: PRT
<213> ORGANISM: Artificial Sequence
<220> FEATURE:
<223> OTHER INFORMATION: Synthetic (VL2)

<400> SEQUENCE: 36

```
Asp Val Val Leu Thr Gln Ser Pro Leu Ser Leu Pro Val Thr Leu Gly
 1                   5                  10                  15

Gln Pro Ala Ser Ile Ser Cys Arg Ser Ser Gln Thr Leu Val Tyr Arg
                 20                  25                  30

Asn Gly Asn Thr Tyr Leu His Trp Tyr Gln Gln Arg Ala Gly Gln Ser
             35                  40                  45

Pro Arg Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Phe Cys Ser Gln Asn
                 85                  90                  95

Thr His Phe Pro Tyr Thr Phe Gly Gly Gly Thr Lys Leu Glu Ile Lys
                100                 105                 110
```

<210> SEQ ID NO 37
<211> LENGTH: 112
<212> TYPE: PRT
<213> ORGANISM: Artificial Sequence
<220> FEATURE:
<223> OTHER INFORMATION: Synthetic (VL3)

<400> SEQUENCE: 37

```
Asp Val Val Leu Thr Gln Thr Pro Leu Ser Ser Pro Val Thr Leu Gly
1               5                   10                  15

Gln Pro Ala Ser Ile Ser Cys Arg Ser Ser Gln Thr Leu Val Tyr Arg
            20                  25                  30

Asn Gly Asn Thr Tyr Leu His Trp Tyr Leu Gln Arg Ala Gly Gln Pro
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Phe Cys Ser Gln Asn
                85                  90                  95

Thr His Phe Pro Tyr Thr Phe Gly Gly Gly Thr Lys Leu Glu Ile Lys
            100                 105                 110
```

<210> SEQ ID NO 38
<211> LENGTH: 112
<212> TYPE: PRT
<213> ORGANISM: Artificial Sequence
<220> FEATURE:
<223> OTHER INFORMATION: Synthetic (VL4)

<400> SEQUENCE: 38

```
Asp Val Val Leu Thr Gln Thr Pro Leu Ser Ser Pro Val Thr Leu Gly
1               5                   10                  15

Gln Pro Ala Ser Ile Ser Cys Arg Ser Ser Gln Thr Leu Val Tyr Arg
            20                  25                  30

Asn Gly Asn Thr Tyr Leu His Trp Tyr Gln Gln Arg Pro Gly Gln Pro
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Phe Cys Ser Gln Asn
                85                  90                  95

Thr His Phe Pro Tyr Thr Phe Gly Gly Gly Thr Lys Leu Glu Ile Lys
            100                 105                 110
```

<210> SEQ ID NO 39
<211> LENGTH: 25
<212> TYPE: PRT
<213> ORGANISM: Artificial Sequence
<220> FEATURE:
<223> OTHER INFORMATION: Synthetic (VH-FR1)

<400> SEQUENCE: 39

```
Gln Val Gln Leu Gln Gln Ser Gly Ala Glu Leu Val Arg Pro Gly Val
1               5                   10                  15

Ser Val Lys Ile Ser Cys Lys Gly Ser
            20                  25
```

```
<210> SEQ ID NO 40
<211> LENGTH: 25
<212> TYPE: PRT
<213> ORGANISM: Artificial Sequence
<220> FEATURE:
<223> OTHER INFORMATION: Synthetic (VH-FR1)

<400> SEQUENCE: 40

Gln Val Gln Leu Val Gln Ser Gly Ala Glu Val Lys Lys Pro Gly Ala
1               5                   10                  15

Ser Val Lys Ile Ser Cys Lys Gly Ser
            20                  25

<210> SEQ ID NO 41
<211> LENGTH: 25
<212> TYPE: PRT
<213> ORGANISM: Artificial Sequence
<220> FEATURE:
<223> OTHER INFORMATION: Synthetic (VH-FR1)

<400> SEQUENCE: 41

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 42
<211> LENGTH: 25
<212> TYPE: PRT
<213> ORGANISM: Artificial Sequence
<220> FEATURE:
<223> OTHER INFORMATION: Synthetic (VH-FR1)

<400> SEQUENCE: 42

Gln Val Gln Leu Val Gln Ser Gly Ala Glu Val Lys Lys Pro Gly Ala
1               5                   10                  15

Ser Val Lys Ile Ser Cys Lys Ala Ser
            20                  25

<210> SEQ ID NO 43
<211> LENGTH: 25
<212> TYPE: PRT
<213> ORGANISM: Artificial Sequence
<220> FEATURE:
<223> OTHER INFORMATION: Synthetic (VH-FR1)

<400> SEQUENCE: 43

Gln Val Gln Leu Val Gln Ser Gly Ala Glu Val Val Lys Pro Gly Ala
1               5                   10                  15

Ser Val Lys Val Ser Cys Lys Gly Ser
            20                  25

<210> SEQ ID NO 44
<211> LENGTH: 25
<212> TYPE: PRT
<213> ORGANISM: Artificial Sequence
<220> FEATURE:
<223> OTHER INFORMATION: Synthetic (VH-FR1)

<400> SEQUENCE: 44

Gln Val Gln Leu Gln Gln Ser Gly Ala Glu Val Lys Lys Pro Gly Ala
1               5                   10                  15

Ser Val Lys Ile Ser Cys Lys Gly Ser
            20                  25
```

<210> SEQ ID NO 45
<211> LENGTH: 25
<212> TYPE: PRT
<213> ORGANISM: Artificial Sequence
<220> FEATURE:
<223> OTHER INFORMATION: Synthetic (VH-FR1)

<400> SEQUENCE: 45

Gln Val Gln Leu Gln Gln Ser Gly Ala Glu Val Val Lys Pro Gly Ala
1               5                   10                  15

Ser Val Lys Val Ser Cys Lys Ala Ser
            20                  25

<210> SEQ ID NO 46
<211> LENGTH: 25
<212> TYPE: PRT
<213> ORGANISM: Artificial Sequence
<220> FEATURE:
<223> OTHER INFORMATION: Synthetic (VH-FR1)

<400> SEQUENCE: 46

Gln Val Gln Leu Val Gln Ser Gly Ala Glu Val Val Lys Pro Gly Ala
1               5                   10                  15

Ser Val Lys Ile Ser Cys Lys Ala Ser
            20                  25

<210> SEQ ID NO 47
<211> LENGTH: 25
<212> TYPE: PRT
<213> ORGANISM: Artificial Sequence
<220> FEATURE:
<223> OTHER INFORMATION: Synthetic (VH-FR1)

<400> SEQUENCE: 47

Gln Val Gln Leu Gln Gln Ser Gly Ala Glu Val Lys Lys Pro Gly Ala
1               5                   10                  15

Ser Val Lys Ile Ser Cys Lys Ala Ser
            20                  25

<210> SEQ ID NO 48
<211> LENGTH: 25
<212> TYPE: PRT
<213> ORGANISM: Artificial Sequence
<220> FEATURE:
<223> OTHER INFORMATION: Synthetic (VH-FR1)

<400> SEQUENCE: 48

Gln Val Gln Leu Gln Gln Ser Gly Ala Glu Val Lys Lys Pro Gly Ala
1               5                   10                  15

Ser Val Lys Val Ser Cys Lys Ala Ser
            20                  25

<210> SEQ ID NO 49
<211> LENGTH: 17
<212> TYPE: PRT
<213> ORGANISM: Artificial Sequence
<220> FEATURE:
<223> OTHER INFORMATION: Synthetic (VH-FR2)

<400> SEQUENCE: 49

Leu His Trp Val Lys Gln Ser His Ala Lys Ser Leu Glu Trp Ile Gly
1               5                   10                  15

Val

<210> SEQ ID NO 50
<211> LENGTH: 17
<212> TYPE: PRT
<213> ORGANISM: Artificial Sequence
<220> FEATURE:
<223> OTHER INFORMATION: Synthetic (VH-FR2)

<400> SEQUENCE: 50

Leu His Trp Val Arg Gln Ala Pro Gly Gln Arg Leu Glu Trp Ile Gly
1               5                   10                  15
Val

<210> SEQ ID NO 51
<211> LENGTH: 17
<212> TYPE: PRT
<213> ORGANISM: Artificial Sequence
<220> FEATURE:
<223> OTHER INFORMATION: Synthetic (VH-FR2)

<400> SEQUENCE: 51

Leu His Trp Val Arg Gln Ala Pro Gly Gln Arg Leu Glu Trp Met Gly
1               5                   10                  15
Val

<210> SEQ ID NO 52
<211> LENGTH: 17
<212> TYPE: PRT
<213> ORGANISM: Artificial Sequence
<220> FEATURE:
<223> OTHER INFORMATION: Synthetic (VH-FR2)

<400> SEQUENCE: 52

Leu His Trp Val Lys Gln Ala Pro Gly Gln Arg Leu Glu Trp Met Gly
1               5                   10                  15
Val

<210> SEQ ID NO 53
<211> LENGTH: 17
<212> TYPE: PRT
<213> ORGANISM: Artificial Sequence
<220> FEATURE:
<223> OTHER INFORMATION: Synthetic (VH-FR2)

<400> SEQUENCE: 53

Leu His Trp Val Arg Gln Ala Pro Gly Gln Ser Leu Glu Trp Met Gly
1               5                   10                  15
Val

<210> SEQ ID NO 54
<211> LENGTH: 17
<212> TYPE: PRT
<213> ORGANISM: Artificial Sequence
<220> FEATURE:
<223> OTHER INFORMATION: Synthetic (VH-FR2)

<400> SEQUENCE: 54

Leu His Trp Val Lys Gln Ala Pro Gly Gln Ser Leu Glu Trp Met Gly
1               5                   10                  15
Val

<210> SEQ ID NO 55
<211> LENGTH: 17
<212> TYPE: PRT

-continued

```
<213> ORGANISM: Artificial Sequence
<220> FEATURE:
<223> OTHER INFORMATION: Synthetic (VH-FR2)

<400> SEQUENCE: 55

Leu His Trp Val Lys Gln Ala Pro Gly Gln Arg Leu Glu Trp Ile Gly
1               5                   10                  15

Val

<210> SEQ ID NO 56
<211> LENGTH: 38
<212> TYPE: PRT
<213> ORGANISM: Artificial Sequence
<220> FEATURE:
<223> OTHER INFORMATION: Synthetic (VH-FR3)

<400> SEQUENCE: 56

Asp Tyr Asn Gln Lys Phe Arg Gly Lys Ala Thr Met Thr Val Asp Lys
1               5                   10                  15

Ser Ser Thr Thr Ala Tyr Leu Glu Leu Ala Arg Leu Thr Ser Glu Asp
            20                  25                  30

Ser Ala Ile His Tyr Cys
        35

<210> SEQ ID NO 57
<211> LENGTH: 38
<212> TYPE: PRT
<213> ORGANISM: Artificial Sequence
<220> FEATURE:
<223> OTHER INFORMATION: Synthetic (VH-FR3)

<400> SEQUENCE: 57

Asp Tyr Asn Gln Lys Phe Arg Gly Arg Ala Thr Ile Thr Arg Asp Thr
1               5                   10                  15

Ser Ala Ser Thr Ala Tyr Met Glu Leu Ser Ser Leu Arg Ser Glu Asp
            20                  25                  30

Thr Ala Val Tyr Tyr Cys
        35

<210> SEQ ID NO 58
<211> LENGTH: 38
<212> TYPE: PRT
<213> ORGANISM: Artificial Sequence
<220> FEATURE:
<223> OTHER INFORMATION: Synthetic (VH-FR3)

<400> SEQUENCE: 58

Asp Tyr Asn Gln Lys Phe Arg Gly Arg Val Thr Met Thr Val Asp Thr
1               5                   10                  15

Ser Ala Ser Thr Ala Tyr Met Glu Leu Ser Ser Leu Arg Ser Glu Asp
            20                  25                  30

Thr Ala Val His Tyr Cys
        35

<210> SEQ ID NO 59
<211> LENGTH: 38
<212> TYPE: PRT
<213> ORGANISM: Artificial Sequence
<220> FEATURE:
<223> OTHER INFORMATION: Synthetic (VH-FR3)

<400> SEQUENCE: 59

Asp Tyr Asn Gln Lys Phe Arg Gly Arg Ala Thr Ile Thr Arg Asp Lys
```

```
1               5                   10                  15
Ser Ala Ser Thr Ala Tyr Leu Glu Leu Ser Ser Leu Arg Ser Glu Asp
            20                  25                  30

Thr Ala Val His Tyr Cys
        35

<210> SEQ ID NO 60
<211> LENGTH: 38
<212> TYPE: PRT
<213> ORGANISM: Artificial Sequence
<220> FEATURE:
<223> OTHER INFORMATION: Synthetic (VH-FR3)

<400> SEQUENCE: 60

Asp Tyr Asn Gln Lys Phe Arg Gly Arg Val Thr Met Thr Arg Asp Thr
1               5                   10                  15

Ser Ala Thr Thr Ala Tyr Leu Glu Leu Ser Ser Leu Arg Ser Glu Asp
            20                  25                  30

Thr Ala Val Tyr Tyr Cys
        35

<210> SEQ ID NO 61
<211> LENGTH: 38
<212> TYPE: PRT
<213> ORGANISM: Artificial Sequence
<220> FEATURE:
<223> OTHER INFORMATION: Synthetic (VH-FR3)

<400> SEQUENCE: 61

Asp Tyr Asn Gln Lys Phe Arg Gly Arg Val Thr Ile Thr Val Asp Lys
1               5                   10                  15

Ser Ala Thr Thr Ala Tyr Met Glu Leu Ser Ser Leu Arg Ser Glu Asp
            20                  25                  30

Thr Ala Val Tyr Tyr Cys
        35

<210> SEQ ID NO 62
<211> LENGTH: 38
<212> TYPE: PRT
<213> ORGANISM: Artificial Sequence
<220> FEATURE:
<223> OTHER INFORMATION: Synthetic (VH-FR3)

<400> SEQUENCE: 62

Lys Tyr Ser Gln Lys Phe Gln Gly Lys Ala Thr Ile Thr Arg Asp Lys
1               5                   10                  15

Ser Ala Ser Thr Ala Tyr Leu Glu Leu Ser Ser Leu Arg Ser Glu Asp
            20                  25                  30

Thr Ala Val Tyr Tyr Cys
        35

<210> SEQ ID NO 63
<211> LENGTH: 38
<212> TYPE: PRT
<213> ORGANISM: Artificial Sequence
<220> FEATURE:
<223> OTHER INFORMATION: Synthetic (VH-FR3)

<400> SEQUENCE: 63

Lys Tyr Ser Gln Lys Phe Gln Gly Arg Ala Thr Met Thr Arg Asp Thr
1               5                   10                  15

Ser Ala Thr Thr Ala Tyr Met Glu Leu Ser Ser Leu Arg Ser Glu Asp
```

-continued

```
                20                  25                  30

Thr Ala Ile His Tyr Cys
        35

<210> SEQ ID NO 64
<211> LENGTH: 38
<212> TYPE: PRT
<213> ORGANISM: Artificial Sequence
<220> FEATURE:
<223> OTHER INFORMATION: Synthetic (VH-FR3)

<400> SEQUENCE: 64

Lys Tyr Ser Gln Lys Phe Gln Gly Arg Ala Thr Met Thr Arg Asp Lys
1               5                   10                  15

Ser Ala Ser Thr Ala Tyr Met Glu Leu Ser Ser Leu Arg Ser Glu Asp
                20                  25                  30

Thr Ala Val Tyr Tyr Cys
        35

<210> SEQ ID NO 65
<211> LENGTH: 38
<212> TYPE: PRT
<213> ORGANISM: Artificial Sequence
<220> FEATURE:
<223> OTHER INFORMATION: Synthetic (VH-FR3)

<400> SEQUENCE: 65

Lys Tyr Ser Gln Lys Phe Gln Gly Lys Val Thr Ile Thr Val Asp Thr
1               5                   10                  15

Ser Ala Thr Thr Ala Tyr Met Glu Leu Ser Ser Leu Arg Ser Glu Asp
                20                  25                  30

Thr Ala Val His Tyr Cys
        35

<210> SEQ ID NO 66
<211> LENGTH: 38
<212> TYPE: PRT
<213> ORGANISM: Artificial Sequence
<220> FEATURE:
<223> OTHER INFORMATION: Synthetic (VH-FR3)

<400> SEQUENCE: 66

Lys Tyr Ser Gln Lys Phe Gln Gly Arg Val Thr Ile Thr Val Asp Thr
1               5                   10                  15

Ser Ala Ser Thr Ala Tyr Leu Glu Leu Ser Ser Leu Arg Ser Glu Asp
                20                  25                  30

Thr Ala Ile Tyr Tyr Cys
        35

<210> SEQ ID NO 67
<211> LENGTH: 38
<212> TYPE: PRT
<213> ORGANISM: Artificial Sequence
<220> FEATURE:
<223> OTHER INFORMATION: Synthetic (VH-FR3)

<400> SEQUENCE: 67

Lys Tyr Ser Gln Lys Phe Gln Gly Lys Val Thr Ile Thr Arg Asp Thr
1               5                   10                  15

Ser Ala Ser Thr Ala Tyr Leu Glu Leu Ser Ser Leu Arg Ser Glu Asp
                20                  25                  30

Thr Ala Ile His Tyr Cys
```

<210> SEQ ID NO 68
<211> LENGTH: 38
<212> TYPE: PRT
<213> ORGANISM: Artificial Sequence
<220> FEATURE:
<223> OTHER INFORMATION: Synthetic (VH-FR3)

<400> SEQUENCE: 68

Lys Tyr Ser Gln Lys Phe Gln Gly Lys Val Thr Ile Thr Arg Asp Thr
1               5                   10                  15

Ser Ala Ser Thr Ala Tyr Leu Glu Leu Ser Ser Leu Arg Ser Glu Asp
            20                  25                  30

Thr Ala Ile His Tyr Cys
        35

<210> SEQ ID NO 69
<211> LENGTH: 38
<212> TYPE: PRT
<213> ORGANISM: Artificial Sequence
<220> FEATURE:
<223> OTHER INFORMATION: Synthetic (VH-FR3)

<400> SEQUENCE: 69

Asp Tyr Asn Gln Lys Phe Arg Gly Arg Val Thr Ile Thr Arg Asp Lys
1               5                   10                  15

Ser Ala Ser Thr Ala Tyr Leu Glu Leu Ser Ser Leu Arg Ser Glu Asp
            20                  25                  30

Thr Ala Val Tyr Tyr Cys
        35

<210> SEQ ID NO 70
<211> LENGTH: 38
<212> TYPE: PRT
<213> ORGANISM: Artificial Sequence
<220> FEATURE:
<223> OTHER INFORMATION: Synthetic (VH-FR3)

<400> SEQUENCE: 70

Asp Tyr Asn Gln Lys Phe Arg Gly Arg Val Thr Ile Thr Val Asp Thr
1               5                   10                  15

Ser Ala Thr Thr Ala Tyr Met Glu Leu Ser Ser Leu Arg Ser Glu Asp
            20                  25                  30

Thr Ala Val His Tyr Cys
        35

<210> SEQ ID NO 71
<211> LENGTH: 38
<212> TYPE: PRT
<213> ORGANISM: Artificial Sequence
<220> FEATURE:
<223> OTHER INFORMATION: Synthetic (VH-FR3)

<400> SEQUENCE: 71

Asp Tyr Asn Gln Lys Phe Arg Gly Arg Val Thr Met Thr Arg Asp Thr
1               5                   10                  15

Ser Ala Ser Thr Ala Tyr Met Glu Leu Ser Ser Leu Arg Ser Glu Asp
            20                  25                  30

Thr Ala Val His Tyr Cys
        35

```
<210> SEQ ID NO 72
<211> LENGTH: 38
<212> TYPE: PRT
<213> ORGANISM: Artificial Sequence
<220> FEATURE:
<223> OTHER INFORMATION: Synthetic (VH-FR3)

<400> SEQUENCE: 72

Asp Tyr Asn Gln Lys Phe Arg Gly Arg Ala Thr Met Thr Arg Asp Thr
1               5                   10                  15

Ser Ala Ser Thr Ala Tyr Leu Glu Leu Ser Ser Leu Arg Ser Glu Asp
            20                  25                  30

Thr Ala Val Tyr Tyr Cys
        35

<210> SEQ ID NO 73
<211> LENGTH: 38
<212> TYPE: PRT
<213> ORGANISM: Artificial Sequence
<220> FEATURE:
<223> OTHER INFORMATION: Synthetic (VH-FR3)

<400> SEQUENCE: 73

Asp Tyr Asn Gln Lys Phe Arg Gly Arg Ala Thr Ile Thr Val Asp Thr
1               5                   10                  15

Ser Ala Ser Thr Ala Tyr Met Glu Leu Ser Ser Leu Arg Ser Glu Asp
            20                  25                  30

Thr Ala Val Tyr Tyr Cys
        35

<210> SEQ ID NO 74
<211> LENGTH: 38
<212> TYPE: PRT
<213> ORGANISM: Artificial Sequence
<220> FEATURE:
<223> OTHER INFORMATION: Synthetic (VH-FR3)

<400> SEQUENCE: 74

Asp Tyr Asn Gln Lys Phe Arg Gly Arg Val Thr Ile Thr Arg Asp Lys
1               5                   10                  15

Ser Ala Thr Thr Ala Tyr Met Glu Leu Ser Ser Leu Arg Ser Glu Asp
            20                  25                  30

Thr Ala Val Tyr Tyr Cys
        35

<210> SEQ ID NO 75
<211> LENGTH: 38
<212> TYPE: PRT
<213> ORGANISM: Artificial Sequence
<220> FEATURE:
<223> OTHER INFORMATION: Synthetic (VH-FR3)

<400> SEQUENCE: 75

Lys Tyr Ser Gln Lys Phe Gln Gly Arg Ala Thr Ile Thr Val Asp Thr
1               5                   10                  15

Ser Ala Thr Thr Ala Tyr Leu Glu Leu Ser Ser Leu Arg Ser Glu Asp
            20                  25                  30

Thr Ala Val Tyr Tyr Cys
        35

<210> SEQ ID NO 76
<211> LENGTH: 38
<212> TYPE: PRT
```

<213> ORGANISM: Artificial Sequence
<220> FEATURE:
<223> OTHER INFORMATION: Synthetic (VH-FR3)

<400> SEQUENCE: 76

Lys Tyr Ser Gln Lys Phe Gln Gly Arg Ala Thr Met Thr Arg Asp Thr
1               5                   10                  15

Ser Ala Ser Thr Ala Tyr Leu Glu Leu Ser Ser Leu Arg Ser Glu Asp
            20                  25                  30

Thr Ala Val His Tyr Cys
        35

<210> SEQ ID NO 77
<211> LENGTH: 38
<212> TYPE: PRT
<213> ORGANISM: Artificial Sequence
<220> FEATURE:
<223> OTHER INFORMATION: Synthetic (VH-FR3)

<400> SEQUENCE: 77

Lys Tyr Ser Gln Lys Phe Gln Gly Arg Val Thr Met Thr Val Asp Lys
1               5                   10                  15

Ser Ala Thr Thr Ala Tyr Leu Glu Leu Ser Ser Leu Arg Ser Glu Asp
            20                  25                  30

Thr Ala Val Tyr Tyr Cys
        35

<210> SEQ ID NO 78
<211> LENGTH: 38
<212> TYPE: PRT
<213> ORGANISM: Artificial Sequence
<220> FEATURE:
<223> OTHER INFORMATION: Synthetic (VH-FR3)

<400> SEQUENCE: 78

Lys Tyr Ser Gln Lys Phe Gln Gly Arg Ala Thr Met Thr Arg Asp Lys
1               5                   10                  15

Ser Ala Thr Thr Ala Tyr Met Glu Leu Ser Ser Leu Arg Ser Glu Asp
            20                  25                  30

Thr Ala Val His Tyr Cys
        35

<210> SEQ ID NO 79
<211> LENGTH: 38
<212> TYPE: PRT
<213> ORGANISM: Artificial Sequence
<220> FEATURE:
<223> OTHER INFORMATION: Synthetic (VH-FR3)

<400> SEQUENCE: 79

Lys Tyr Ser Gln Lys Phe Gln Gly Arg Ala Thr Met Thr Val Asp Lys
1               5                   10                  15

Ser Ala Ser Thr Ala Tyr Leu Glu Leu Ser Ser Leu Arg Ser Glu Asp
            20                  25                  30

Thr Ala Val His Tyr Cys
        35

<210> SEQ ID NO 80
<211> LENGTH: 38
<212> TYPE: PRT
<213> ORGANISM: Artificial Sequence
<220> FEATURE:
<223> OTHER INFORMATION: Synthetic (VH-FR3)

<400> SEQUENCE: 80

Lys Tyr Ser Gln Lys Phe Gln Gly Arg Val Thr Ile Thr Val Asp Lys
1               5                   10                  15

Ser Ala Thr Thr Ala Tyr Met Glu Leu Ser Ser Leu Arg Ser Glu Asp
            20                  25                  30

Thr Ala Val His Tyr Cys
        35

<210> SEQ ID NO 81
<211> LENGTH: 11
<212> TYPE: PRT
<213> ORGANISM: Artificial Sequence
<220> FEATURE:
<223> OTHER INFORMATION: Synthetic (VH-FR4)

<400> SEQUENCE: 81

Trp Gly Gln Gly Thr Ala Leu Thr Val Ser Ser
1               5                   10

<210> SEQ ID NO 82
<211> LENGTH: 26
<212> TYPE: PRT
<213> ORGANISM: Artificial Sequence
<220> FEATURE:
<223> OTHER INFORMATION: Synthetic (VL-FR1)

<400> SEQUENCE: 82

Asp Val Val Leu Thr Gln Thr Pro Leu Ser Leu Pro Val Asn Leu Gly
1               5                   10                  15

Asp Gln Ala Ser Ile Ser Cys Arg Ser Ser
            20                  25

<210> SEQ ID NO 83
<211> LENGTH: 26
<212> TYPE: PRT
<213> ORGANISM: Artificial Sequence
<220> FEATURE:
<223> OTHER INFORMATION: Synthetic (VL-FR1)

<400> SEQUENCE: 83

Asp Val Val Leu Thr Gln Ser Pro Leu Ser Leu Pro Val Thr Leu Gly
1               5                   10                  15

Gln Pro Ala Ser Ile Ser Cys Arg Ser Ser
            20                  25

<210> SEQ ID NO 84
<211> LENGTH: 26
<212> TYPE: PRT
<213> ORGANISM: Artificial Sequence
<220> FEATURE:
<223> OTHER INFORMATION: Synthetic (VL-FR1)

<400> SEQUENCE: 84

Asp Val Val Leu Thr Gln Thr Pro Leu Ser Ser Pro Val Thr Leu Gly
1               5                   10                  15

Gln Pro Ala Ser Ile Ser Cys Arg Ser Ser
            20                  25

<210> SEQ ID NO 85
<211> LENGTH: 17
<212> TYPE: PRT
<213> ORGANISM: Artificial Sequence
<220> FEATURE:

<223> OTHER INFORMATION: Synthetic (VL-FR2)

<400> SEQUENCE: 85

Leu His Trp Tyr Leu Gln Lys Ala Gly Gln Ser Pro Lys Leu Leu Ile
1               5                   10                  15
Tyr

<210> SEQ ID NO 86
<211> LENGTH: 16
<212> TYPE: PRT
<213> ORGANISM: Artificial Sequence
<220> FEATURE:
<223> OTHER INFORMATION: Synthetic (VL-FR2)

<400> SEQUENCE: 86

Leu His Trp Tyr Leu Gln Lys Ala Gly Gln Ser Pro Lys Leu Leu Ile
1               5                   10                  15

<210> SEQ ID NO 87
<211> LENGTH: 17
<212> TYPE: PRT
<213> ORGANISM: Artificial Sequence
<220> FEATURE:
<223> OTHER INFORMATION: Synthetic (VL-FR2)

<400> SEQUENCE: 87

Leu His Trp Tyr Gln Gln Arg Ala Gly Gln Ser Pro Arg Leu Leu Ile
1               5                   10                  15
Tyr

<210> SEQ ID NO 88
<211> LENGTH: 17
<212> TYPE: PRT
<213> ORGANISM: Artificial Sequence
<220> FEATURE:
<223> OTHER INFORMATION: Synthetic (VL-FR2)

<400> SEQUENCE: 88

Leu His Trp Tyr Leu Gln Arg Ala Gly Gln Pro Pro Arg Leu Leu Ile
1               5                   10                  15
Tyr

<210> SEQ ID NO 89
<211> LENGTH: 17
<212> TYPE: PRT
<213> ORGANISM: Artificial Sequence
<220> FEATURE:
<223> OTHER INFORMATION: Synthetic (VL-FR2)

<400> SEQUENCE: 89

Leu His Trp Tyr Gln Gln Arg Pro Gly Gln Pro Pro Arg Leu Leu Ile
1               5                   10                  15
Tyr

<210> SEQ ID NO 90
<211> LENGTH: 36
<212> TYPE: PRT
<213> ORGANISM: Artificial Sequence
<220> FEATURE:
<223> OTHER INFORMATION: Synthetic (VL-FR3)

<400> SEQUENCE: 90

Asn Arg Phe Ser Gly Val Pro Asp Arg Phe Ser Gly Ser Gly Ser Gly
1               5                   10                  15

Thr Asp Phe Thr Leu Lys Ile Ser Arg Val Glu Ala Glu Asp Leu Gly
            20                  25                  30

Val Tyr Phe Cys
        35

<210> SEQ ID NO 91
<211> LENGTH: 36
<212> TYPE: PRT
<213> ORGANISM: Artificial Sequence
<220> FEATURE:
<223> OTHER INFORMATION: Synthetic (VL-FR3)

<400> SEQUENCE: 91

Asn Arg Phe Ser Gly Val Pro Asp Arg Phe Ser Gly Ser Gly Ser Gly
1               5                   10                  15

Thr Asp Phe Thr Leu Lys Ile Ser Arg Val Glu Ala Glu Asp Val Gly
            20                  25                  30

Val Tyr Phe Cys
        35

<210> SEQ ID NO 92
<211> LENGTH: 36
<212> TYPE: PRT
<213> ORGANISM: Artificial Sequence
<220> FEATURE:
<223> OTHER INFORMATION: Synthetic (VL-FR3)

<400> SEQUENCE: 92

Asn Arg Phe Ser Gly Val Pro Asp Arg Phe Ser Gly Ser Gly Ala Gly
1               5                   10                  15

Thr Asp Phe Thr Leu Lys Ile Ser Arg Val Glu Ala Glu Asp Val Gly
            20                  25                  30

Val Tyr Phe Cys
        35

<210> SEQ ID NO 93
<211> LENGTH: 10
<212> TYPE: PRT
<213> ORGANISM: Artificial Sequence
<220> FEATURE:
<223> OTHER INFORMATION: Synthetic (VL-FR4)

<400> SEQUENCE: 93

Phe Gly Gly Gly Thr Lys Ile Lys Arg Gln
1               5                   10

<210> SEQ ID NO 94
<211> LENGTH: 11
<212> TYPE: PRT
<213> ORGANISM: Artificial Sequence
<220> FEATURE:
<223> OTHER INFORMATION: Synthetic (VL-FR4)

<400> SEQUENCE: 94

Phe Gly Gly Gly Thr Lys Leu Glu Ile Lys Arg
1               5                   10

<210> SEQ ID NO 95
<211> LENGTH: 327
<212> TYPE: PRT
<213> ORGANISM: Artificial Sequence
<220> FEATURE:
<223> OTHER INFORMATION: Synthetic (Heavy Chain)

<400> SEQUENCE: 95

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 96
<211> LENGTH: 106
<212> TYPE: PRT
<213> ORGANISM: Artificial Sequence
<220> FEATURE:
<223> OTHER INFORMATION: Synthetic (Light Chain)

<400> SEQUENCE: 96

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr

```
                    20                  25                  30
Pro Arg Glu Ala Lys Val Gln Trp Lys Val Asp Asn Ala Leu Gln Ser
                35                  40                  45

Gly Asn Ser Gln Glu Ser Val Thr Glu Gln Asp Ser Lys Asp Ser Thr
            50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
                100                 105

<210> SEQ ID NO 97
<211> LENGTH: 25
<212> TYPE: PRT
<213> ORGANISM: Artificial Sequence
<220> FEATURE:
<223> OTHER INFORMATION: Synthetic (VH-FR1)
<220> FEATURE:
<221> NAME/KEY: MOD_RES
<222> LOCATION: (5)
<223> OTHER INFORMATION: Xaa is Gln or Val
<220> FEATURE:
<221> NAME/KEY: MOD_RES
<222> LOCATION: (11)
<223> OTHER INFORMATION: Xaa is Leu or Val
<220> FEATURE:
<221> NAME/KEY: MOD_RES
<222> LOCATION: (12)
<223> OTHER INFORMATION: Xaa is Val or Lys
<220> FEATURE:
<221> NAME/KEY: MOD_RES
<222> LOCATION: (13)
<223> OTHER INFORMATION: Xaa is Arg or Lys
<220> FEATURE:
<221> NAME/KEY: MOD_RES
<222> LOCATION: (16)
<223> OTHER INFORMATION: Xaa is Val or Ala
<220> FEATURE:
<221> NAME/KEY: MOD_RES
<222> LOCATION: (20)
<223> OTHER INFORMATION: Xaa is Ile or Val
<220> FEATURE:
<221> NAME/KEY: MOD_RES
<222> LOCATION: (24)
<223> OTHER INFORMATION: Xaa is Gly or Ala

<400> SEQUENCE: 97

Gln Val Gln Leu Xaa Gln Ser Gly Ala Glu Xaa Xaa Xaa Pro Gly Xaa
1               5                   10                  15

Ser Val Lys Xaa Ser Cys Lys Xaa Ser
                20                  25

<210> SEQ ID NO 98
<211> LENGTH: 25
<212> TYPE: PRT
<213> ORGANISM: Artificial Sequence
<220> FEATURE:
<223> OTHER INFORMATION: Synthetic (VH-FR1)
<220> FEATURE:
<221> NAME/KEY: MOD_RES
<222> LOCATION: (5)
<223> OTHER INFORMATION: Xaa is Val or Gln
<220> FEATURE:
<221> NAME/KEY: MOD_RES
<222> LOCATION: (12)
<223> OTHER INFORMATION: Xaa is Lys or Val
<220> FEATURE:
<221> NAME/KEY: MOD_RES
<222> LOCATION: (20)
```

```
<223> OTHER INFORMATION: Xaa is Ile or Val
<220> FEATURE:
<221> NAME/KEY: MOD_RES
<222> LOCATION: (24)
<223> OTHER INFORMATION: Xaa is Gly or Ala

<400> SEQUENCE: 98

Gln Val Gln Leu Xaa Gln Ser Gly Ala Glu Val Xaa Lys Pro Gly Ala
1               5                   10                  15

Ser Val Lys Xaa Ser Cys Lys Xaa Ser
            20                  25

<210> SEQ ID NO 99
<211> LENGTH: 17
<212> TYPE: PRT
<213> ORGANISM: Artificial Sequence
<220> FEATURE:
<223> OTHER INFORMATION: Synthetic (VH-FR2)
<220> FEATURE:
<221> NAME/KEY: MOD_RES
<222> LOCATION: (5)
<223> OTHER INFORMATION: Xaa is Lys or Arg
<220> FEATURE:
<221> NAME/KEY: MOD_RES
<222> LOCATION: (7)
<223> OTHER INFORMATION: Xaa is Ser or Ala
<220> FEATURE:
<221> NAME/KEY: MOD_RES
<222> LOCATION: (8)
<223> OTHER INFORMATION: Xaa is His or Pro
<220> FEATURE:
<221> NAME/KEY: MOD_RES
<222> LOCATION: (9)
<223> OTHER INFORMATION: Xaa is Ala or Gly
<220> FEATURE:
<221> NAME/KEY: MOD_RES
<222> LOCATION: (10)
<223> OTHER INFORMATION: Xaa is Lys or Gln
<220> FEATURE:
<221> NAME/KEY: MOD_RES
<222> LOCATION: (11)
<223> OTHER INFORMATION: Xaa is Ser or Arg
<220> FEATURE:
<221> NAME/KEY: MOD_RES
<222> LOCATION: (15)
<223> OTHER INFORMATION: Xaa is Ile or Met

<400> SEQUENCE: 99

Leu His Trp Val Xaa Gln Xaa Xaa Xaa Xaa Xaa Leu Glu Trp Xaa Gly
1               5                   10                  15

Val

<210> SEQ ID NO 100
<211> LENGTH: 17
<212> TYPE: PRT
<213> ORGANISM: Artificial Sequence
<220> FEATURE:
<223> OTHER INFORMATION: Synthetic (VH-FR2)
<220> FEATURE:
<221> NAME/KEY: MOD_RES
<222> LOCATION: (5)
<223> OTHER INFORMATION: Xaa is Arg or Lys
<220> FEATURE:
<221> NAME/KEY: MOD_RES
<222> LOCATION: (11)
<223> OTHER INFORMATION: Xaa is Arg or Ser
<220> FEATURE:
<221> NAME/KEY: MOD_RES
<222> LOCATION: (15)
<223> OTHER INFORMATION: Xaa is Ile or Met

<400> SEQUENCE: 100
```

```
Leu His Trp Val Xaa Gln Ala Pro Gly Gln Xaa Leu Glu Trp Xaa Gly
1               5                   10                  15

Val
```

```
<210> SEQ ID NO 101
<211> LENGTH: 38
<212> TYPE: PRT
<213> ORGANISM: Artificial Sequence
<220> FEATURE:
<223> OTHER INFORMATION: Synthetic (VH-FR3)
<220> FEATURE:
<221> NAME/KEY: MOD_RES
<222> LOCATION: (1)
<223> OTHER INFORMATION: Xaa is Asp or Lys
<220> FEATURE:
<221> NAME/KEY: MOD_RES
<222> LOCATION: (3)
<223> OTHER INFORMATION: Xaa is Asn or Ser
<220> FEATURE:
<221> NAME/KEY: MOD_RES
<222> LOCATION: (7)
<223> OTHER INFORMATION: Xaa is Arg or Gln
<220> FEATURE:
<221> NAME/KEY: MOD_RES
<222> LOCATION: (9)
<223> OTHER INFORMATION: Xaa is Lys or Arg
<220> FEATURE:
<221> NAME/KEY: MOD_RES
<222> LOCATION: (10)
<223> OTHER INFORMATION: Xaa is Ala or Val
<220> FEATURE:
<221> NAME/KEY: MOD_RES
<222> LOCATION: (12)
<223> OTHER INFORMATION: Xaa is Met or Ile
<220> FEATURE:
<221> NAME/KEY: MOD_RES
<222> LOCATION: (14)
<223> OTHER INFORMATION: Xaa is Val or Arg
<220> FEATURE:
<221> NAME/KEY: MOD_RES
<222> LOCATION: (16)
<223> OTHER INFORMATION: Xaa is Lys or Thr
<220> FEATURE:
<221> NAME/KEY: MOD_RES
<222> LOCATION: (18)
<223> OTHER INFORMATION: Xaa is Ser or Ala
<220> FEATURE:
<221> NAME/KEY: MOD_RES
<222> LOCATION: (19)
<223> OTHER INFORMATION: Xaa is Thr or Ser
<220> FEATURE:
<221> NAME/KEY: MOD_RES
<222> LOCATION: (23)
<223> OTHER INFORMATION: Xaa is Leu or Met
<220> FEATURE:
<221> NAME/KEY: MOD_RES
<222> LOCATION: (26)
<223> OTHER INFORMATION: Xaa is Ala or Ser
<220> FEATURE:
<221> NAME/KEY: MOD_RES
<222> LOCATION: (27)
<223> OTHER INFORMATION: Xaa is Arg or Ser
<220> FEATURE:
<221> NAME/KEY: MOD_RES
<222> LOCATION: (29)
<223> OTHER INFORMATION: Xaa is Thr or Arg
<220> FEATURE:
<221> NAME/KEY: MOD_RES
<222> LOCATION: (33)
<223> OTHER INFORMATION: Xaa is Ser or Thr
<220> FEATURE:
<221> NAME/KEY: MOD_RES
<222> LOCATION: (35)
<223> OTHER INFORMATION: Xaa is Ile or Val
<220> FEATURE:
<221> NAME/KEY: MOD_RES
<222> LOCATION: (36)
```

<223> OTHER INFORMATION: Xaa is His or Tyr

<400> SEQUENCE: 101

Xaa Tyr Xaa Gln Lys Phe Xaa Gly Xaa Xaa Thr Xaa Thr Xaa Asp Xaa
1               5                   10                  15

Ser Xaa Xaa Thr Ala Tyr Xaa Glu Leu Xaa Xaa Leu Xaa Ser Glu Asp
            20                  25                  30

Xaa Ala Xaa Xaa Tyr Cys
        35

<210> SEQ ID NO 102
<211> LENGTH: 38
<212> TYPE: PRT
<213> ORGANISM: Artificial Sequence
<220> FEATURE:
<223> OTHER INFORMATION: Synthetic (VH-FR3)
<220> FEATURE:
<221> NAME/KEY: MOD_RES
<222> LOCATION: (1)
<223> OTHER INFORMATION: Xaa is Asp or Lys
<220> FEATURE:
<221> NAME/KEY: MOD_RES
<222> LOCATION: (3)
<223> OTHER INFORMATION: Xaa is Asn or Ser
<220> FEATURE:
<221> NAME/KEY: MOD_RES
<222> LOCATION: (7)
<223> OTHER INFORMATION: Xaa is Arg or Gln
<220> FEATURE:
<221> NAME/KEY: MOD_RES
<222> LOCATION: (9)
<223> OTHER INFORMATION: Xaa is Arg or Lys
<220> FEATURE:
<221> NAME/KEY: MOD_RES
<222> LOCATION: (10)
<223> OTHER INFORMATION: Xaa is Ala or Val
<220> FEATURE:
<221> NAME/KEY: MOD_RES
<222> LOCATION: (12)
<223> OTHER INFORMATION: Xaa is Ile or Met
<220> FEATURE:
<221> NAME/KEY: MOD_RES
<222> LOCATION: (14)
<223> OTHER INFORMATION: Xaa is Arg or Val
<220> FEATURE:
<221> NAME/KEY: MOD_RES
<222> LOCATION: (16)
<223> OTHER INFORMATION: Xaa is Thr or Lys
<220> FEATURE:
<221> NAME/KEY: MOD_RES
<222> LOCATION: (19)
<223> OTHER INFORMATION: Xaa is Ser or Thr
<220> FEATURE:
<221> NAME/KEY: MOD_RES
<222> LOCATION: (23)
<223> OTHER INFORMATION: Xaa is Met or Leu
<220> FEATURE:
<221> NAME/KEY: MOD_RES
<222> LOCATION: (35)
<223> OTHER INFORMATION: Xaa is Val or Ile
<220> FEATURE:
<221> NAME/KEY: MOD_RES
<222> LOCATION: (36)
<223> OTHER INFORMATION: Xaa is Tyr or His

<400> SEQUENCE: 102

Xaa Tyr Xaa Gln Lys Phe Xaa Gly Xaa Xaa Thr Xaa Thr Xaa Arg Xaa
1               5                   10                  15

Ser Ala Xaa Thr Ala Tyr Xaa Glu Leu Ser Ser Leu Arg Ser Glu Asp
            20                  25                  30

Thr Ala Xaa Xaa Tyr Cys
        35

```
<210> SEQ ID NO 103
<211> LENGTH: 26
<212> TYPE: PRT
<213> ORGANISM: Artificial Sequence
<220> FEATURE:
<223> OTHER INFORMATION: Synthetic (VL-FR1)
<220> FEATURE:
<221> NAME/KEY: MOD_RES
<222> LOCATION: (7)
<223> OTHER INFORMATION: Xaa is Thr or Ser
<220> FEATURE:
<221> NAME/KEY: MOD_RES
<222> LOCATION: (11)
<223> OTHER INFORMATION: Xaa is Leu or Ser
<220> FEATURE:
<221> NAME/KEY: MOD_RES
<222> LOCATION: (14)
<223> OTHER INFORMATION: Xaa is Asn or Thr
<220> FEATURE:
<221> NAME/KEY: MOD_RES
<222> LOCATION: (17)
<223> OTHER INFORMATION: Xaa is Asp or Gln
<220> FEATURE:
<221> NAME/KEY: MOD_RES
<222> LOCATION: (18)
<223> OTHER INFORMATION: Xaa is Gln or Pro

<400> SEQUENCE: 103

Asp Val Val Leu Thr Gln Xaa Pro Leu Ser Xaa Pro Val Xaa Leu Gly
1               5                   10                  15

Xaa Xaa Ala Ser Ile Ser Cys Arg Ser Ser
            20                  25

<210> SEQ ID NO 104
<211> LENGTH: 26
<212> TYPE: PRT
<213> ORGANISM: Artificial Sequence
<220> FEATURE:
<223> OTHER INFORMATION: Synthetic (VL-FR1)
<220> FEATURE:
<221> NAME/KEY: MOD_RES
<222> LOCATION: (7)
<223> OTHER INFORMATION: Xaa is Ser or Thr
<220> FEATURE:
<221> NAME/KEY: MOD_RES
<222> LOCATION: (11)
<223> OTHER INFORMATION: Xaa is Leu or Ser

<400> SEQUENCE: 104

Asp Val Val Leu Thr Gln Xaa Pro Leu Ser Xaa Pro Val Thr Leu Gly
1               5                   10                  15

Gln Pro Ala Ser Ile Ser Cys Arg Ser Ser
            20                  25

<210> SEQ ID NO 105
<211> LENGTH: 17
<212> TYPE: PRT
<213> ORGANISM: Artificial Sequence
<220> FEATURE:
<223> OTHER INFORMATION: Synthetic (VL-FR2)
<220> FEATURE:
<221> NAME/KEY: MOD_RES
<222> LOCATION: (5)
<223> OTHER INFORMATION: Xaa is Leu or Gln
<220> FEATURE:
<221> NAME/KEY: MOD_RES
<222> LOCATION: (7)
<223> OTHER INFORMATION: Xaa is Lys or Arg
<220> FEATURE:
<221> NAME/KEY: MOD_RES
<222> LOCATION: (8)
```

```
<223> OTHER INFORMATION: Xaa is Ala or Pro
<220> FEATURE:
<221> NAME/KEY: MOD_RES
<222> LOCATION: (11)
<223> OTHER INFORMATION: Xaa is Ser or Pro
<220> FEATURE:
<221> NAME/KEY: MOD_RES
<222> LOCATION: (13)
<223> OTHER INFORMATION: Xaa is Lys or Arg
<220> FEATURE:
<221> NAME/KEY: MOD_RES
<222> LOCATION: (17)
<223> OTHER INFORMATION: Xaa is Tyr or absent

<400> SEQUENCE: 105

Leu His Trp Tyr Xaa Gln Xaa Xaa Gly Gln Xaa Pro Xaa Leu Leu Ile
1               5                   10                  15

Xaa

<210> SEQ ID NO 106
<211> LENGTH: 36
<212> TYPE: PRT
<213> ORGANISM: Artificial Sequence
<220> FEATURE:
<223> OTHER INFORMATION: Synthetic (VL-FR3)
<220> FEATURE:
<221> NAME/KEY: MOD_RES
<222> LOCATION: (15)
<223> OTHER INFORMATION: Xaa is Ser or Ala
<220> FEATURE:
<221> NAME/KEY: MOD_RES
<222> LOCATION: (31)
<223> OTHER INFORMATION: Xaa is Leu or Val

<400> SEQUENCE: 106

Asn Arg Phe Ser Gly Val Pro Asp Arg Phe Ser Gly Ser Gly Xaa Gly
1               5                   10                  15

Thr Asp Phe Thr Leu Lys Ile Ser Arg Val Glu Ala Glu Asp Xaa Gly
                20                  25                  30

Val Tyr Phe Cys
            35

<210> SEQ ID NO 107
<211> LENGTH: 11
<212> TYPE: PRT
<213> ORGANISM: Artificial Sequence
<220> FEATURE:
<223> OTHER INFORMATION: Synthetic (VL-FR4)
<220> FEATURE:
<221> NAME/KEY: MOD_RES
<222> LOCATION: (7)
<223> OTHER INFORMATION: Xaa is Ile or Leu
<220> FEATURE:
<221> NAME/KEY: MOD_RES
<222> LOCATION: (8)
<223> OTHER INFORMATION: Xaa is Lys or Glu
<220> FEATURE:
<221> NAME/KEY: MOD_RES
<222> LOCATION: (9)
<223> OTHER INFORMATION: Xaa is Arg or Ile
<220> FEATURE:
<221> NAME/KEY: MOD_RES
<222> LOCATION: (10)
<223> OTHER INFORMATION: Xaa is Gln or Lys
<220> FEATURE:
<221> NAME/KEY: MOD_RES
<222> LOCATION: (11)
<223> OTHER INFORMATION: Xaa is Arg or absent
```

<400> SEQUENCE: 107

```
Phe Gly Gly Gly Thr Lys Xaa Xaa Xaa Xaa Xaa
1               5                   10
```